United States Patent
Wening et al.

(10) Patent No.: US 10,842,750 B2
(45) Date of Patent: Nov. 24, 2020

(54) PROTECTING ORAL OVERDOSE WITH ABUSE DETERRENT IMMEDIATE RELEASE FORMULATIONS

(71) Applicant: GRÜNENTHAL GMBH, Aachen (DE)

(72) Inventors: Klaus Wening, Cologne (DE); Sebastian Schwier, Aachen (DE); Ulrike Bertram, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 15/260,643

(22) Filed: Sep. 9, 2016

(65) Prior Publication Data

US 2017/0071862 A1 Mar. 16, 2017

(30) Foreign Application Priority Data

Sep. 10, 2015 (EP) .................................... 15184634

(51) Int. Cl.
| | |
|---|---|
| *A61K 9/20* | (2006.01) |
| *A61K 31/137* | (2006.01) |
| *A61K 31/167* | (2006.01) |
| *A61K 31/485* | (2006.01) |
| *A61K 9/48* | (2006.01) |
| *A61K 9/16* | (2006.01) |
| *A61K 31/138* | (2006.01) |

(52) U.S. Cl.
CPC .......... *A61K 9/2022* (2013.01); *A61K 9/1641* (2013.01); *A61K 9/2054* (2013.01); *A61K 9/4808* (2013.01); *A61K 31/137* (2013.01); *A61K 31/138* (2013.01); *A61K 31/167* (2013.01); *A61K 31/485* (2013.01); *A61K 9/1694* (2013.01)

(58) Field of Classification Search
CPC .. A61K 9/2022; A61K 31/137; A61K 31/167; A61K 31/485; A61K 9/1641; A61K 9/2054; A61K 9/4808; A61K 9/1694
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A | 4/1972 | Ledergerber |
| 3,806,603 A | 4/1974 | Gaunt et al. |
| 3,865,108 A | 9/1975 | Artop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Bannwarth, Bernard. Drugs, 2012, vol. 72, pp. 1713-1723.*

(Continued)

*Primary Examiner* — Doan T Phan

(74) *Attorney, Agent, or Firm* — Norris McLaughlin, P.A.

(57) ABSTRACT

The invention relates to a pharmaceutical dosage form which is particularly useful for the prevention of an overdose of the pharmacologically active ingredient contained therein after accidental or intentional simultaneous administration of a plurality of the dosage forms containing an overall supratherapeutic dose of the pharmacologically active ingredient.

28 Claims, 16 Drawing Sheets

(56) References Cited

U.S. PATENT DOCUMENTS

| | | |
|---|---|---|
| 4,806,337 A | 9/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | Mc Ginity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Grain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Yer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breitenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,946,146 B2 | 9/2005 | Mulye |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |

(56) References Cited

U.S. PATENT DOCUMENTS

| | | |
|---|---|---|
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Marić et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,675,610 B2 | 6/2017 | Bartholomaeus et al. |
| 9,737,490 B2 | 8/2017 | Barnscheid et al. |
| 9,750,701 B2 | 9/2017 | Jans et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 10,058,548 B2 | 8/2018 | Arkenau-Maric et al. |
| 10,130,591 B2 | 11/2018 | Bartholomäus et al. |
| 10,154,966 B2 | 12/2018 | Barnscheid et al. |
| 10,369,109 B2 | 8/2019 | Bartholomaeus et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney |
| 2003/0158265 A1 | 6/2003 | Radhakrishnan et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0079138 A1 | 4/2005 | Chickering, III et al. |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogmann et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0193782 A1 | 6/2006 | Bartholomeus et al. |
| 2006/0182801 A1 | 8/2006 | Breder et al. |
| 2006/0188447 A1 | 8/2006 | Arkenau-Maric et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0204575 A1 | 9/2006 | Feng et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1 | 3/2007 | Chastain et al. |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |

(56) References Cited

U.S. PATENT DOCUMENTS

| | | |
|---|---|---|
| 2007/0259045 A1 | 11/2007 | Mannion et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyendecker et al. |
| 2008/0152595 A1 | 6/2008 | Emigh et al. |
| 2008/0181932 A1 | 7/2008 | Bortz et al. |
| 2008/0207757 A1 | 8/2008 | Mickle |
| 2008/0220079 A1 | 9/2008 | Chen |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1* | 1/2009 | Arkenau-Maric ... A61K 9/1635 424/465 |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1 | 6/2009 | Richardson et al. |
| 2009/0155357 A1 | 6/2009 | Muhuri |
| 2009/0202634 A1 | 8/2009 | Lans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Dufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0260844 A1 | 10/2010 | Scicinski et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0077238 A1 | 3/2011 | Leech et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0135731 A1 | 6/2011 | Kao et al. |
| 2011/0159100 A1 | 6/2011 | Andersen et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0277319 A1 | 11/2012 | Steigerwald et al. |
| 2012/0321716 A1 | 12/2012 | Vachon et al. |
| 2013/0017262 A1 | 1/2013 | Mullen et al. |
| 2013/0022654 A1 | 1/2013 | Deshmukh et al. |
| 2013/0028970 A1* | 1/2013 | Schwier ............... A61K 9/2081 424/464 |
| 2013/0028972 A1 | 1/2013 | Schwier et al. |
| 2013/0059010 A1 | 3/2013 | Henry et al. |
| 2013/0090349 A1 | 4/2013 | Geißler et al. |
| 2013/0129825 A1 | 5/2013 | Billoet et al. |
| 2013/0129826 A1 | 5/2013 | Geißler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomaus et al. |
| 2013/0280338 A1 | 10/2013 | Wening et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0271848 A1 | 9/2014 | Guido et al. |
| 2014/0275143 A1 | 9/2014 | Devarakonda et al. |
| 2014/0356426 A1* | 12/2014 | Barnscheid ............ A61K 9/146 424/463 |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1* | 4/2015 | Haswani ............... A61K 9/2054 424/465 |
| 2015/0190348 A1 | 7/2015 | Haksar et al. |
| 2015/0313850 A1 | 11/2015 | Krishnamurthy et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0346274 A1 | 12/2016 | Vaka et al. |
| 2016/0361308 A1 | 12/2016 | Bartholomaus et al. |
| 2016/0367549 A1 | 12/2016 | Bartholomaus et al. |

(56) References Cited

U.S. PATENT DOCUMENTS

| | | |
|---|---|---|
| 2017/0027886 A1 | 2/2017 | Bartholomaus et al. |
| 2017/0112766 A1 | 4/2017 | Wening et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | PI0413318 A | 10/2006 |
| BR | PI0413361 A | 10/2006 |
| BR | PI0513300 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2713128 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP0663445 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |

(56) References Cited

FOREIGN PATENT DOCUMENTS

| | | | |
|---|---|---|---|
| EP | 0647448 | A1 | 4/1995 |
| EP | 0654263 | A1 | 5/1995 |
| EP | 0661045 | A1 | 7/1995 |
| EP | 0675710 | A1 | 10/1995 |
| EP | 0682945 | A2 | 11/1995 |
| EP | 0693475 | A1 | 1/1996 |
| EP | 0820693 | A1 | 1/1996 |
| EP | 0696598 | A1 | 2/1996 |
| EP | 0216453 | B1 | 3/1996 |
| EP | 0583726 | B1 | 11/1996 |
| EP | 0756480 | A1 | 2/1997 |
| EP | 0760654 | A1 | 3/1997 |
| EP | 0761211 | A1 | 3/1997 |
| EP | 0780369 | A1 | 6/1997 |
| EP | 0785775 | A1 | 7/1997 |
| EP | 0809488 | A1 | 12/1997 |
| EP | 0820698 | A1 | 1/1998 |
| EP | 0820753 | A2 | 1/1998 |
| EP | 0857062 | A2 | 8/1998 |
| EP | 0864324 | A1 | 9/1998 |
| EP | 0864326 | A2 | 9/1998 |
| EP | 0598606 | B1 | 6/1999 |
| EP | 0675710 | B1 | 8/1999 |
| EP | 0980894 | A1 | 2/2000 |
| EP | 0988106 | A1 | 3/2000 |
| EP | 1014941 | A1 | 7/2000 |
| EP | 1070504 | A1 | 1/2001 |
| EP | 1127871 | A1 | 8/2001 |
| EP | 1138321 | A2 | 10/2001 |
| EP | 1152026 | A1 | 11/2001 |
| EP | 1138321 | A3 | 1/2002 |
| EP | 1166776 | A2 | 1/2002 |
| EP | 1166776 | B1 | 1/2002 |
| EP | 1201233 | A1 | 5/2002 |
| EP | 0661045 | B1 | 7/2002 |
| EP | 1250045 | A2 | 10/2002 |
| EP | 1251120 | A1 | 10/2002 |
| EP | 1293127 | A2 | 3/2003 |
| EP | 1293195 | A1 | 3/2003 |
| EP | 1293196 | A2 | 3/2003 |
| EP | 1127871 | B1 | 9/2003 |
| EP | 1201233 | B1 | 12/2004 |
| EP | 1251120 | B1 | 12/2004 |
| EP | 1492506 | B1 | 1/2005 |
| EP | 1502592 | A1 | 2/2005 |
| EP | 1658055 | A1 | 2/2005 |
| EP | 1515702 | B1 | 3/2005 |
| EP | 1527775 | A1 | 4/2005 |
| EP | 1558221 | A1 | 8/2005 |
| EP | 1558257 | A1 | 8/2005 |
| EP | 1560585 | B1 | 8/2005 |
| EP | 1611880 | A2 | 1/2006 |
| EP | 1658054 | B1 | 5/2006 |
| EP | 1740161 | A2 | 1/2007 |
| EP | 1138321131 | | 1/2007 |
| EP | 1658055 | B1 | 3/2007 |
| EP | 1765303 | A1 | 3/2007 |
| EP | 1786403 | A1 | 5/2007 |
| EP | 1558221 | B1 | 6/2007 |
| EP | 1813276 | A1 | 8/2007 |
| EP | 1842533 | A2 | 10/2007 |
| EP | 1845955 | A1 | 10/2007 |
| EP | 1845956 | A1 | 10/2007 |
| EP | 1859789 | A1 | 11/2007 |
| EP | 1980245 | A1 | 10/2008 |
| EP | 1897545 | A1 | 12/2008 |
| EP | 2131830 | A2 | 12/2009 |
| EP | 2246063 | A1 | 11/2010 |
| EP | 2249811 | A1 | 11/2010 |
| EP | 2273983 | A1 | 1/2011 |
| EP | 2402004 | A2 | 1/2012 |
| ES | 2336571 | T3 | 12/2004 |
| ES | 2260042 | T3 | 11/2006 |
| ES | 2285497 | T3 | 11/2007 |
| ES | 2288621 | T3 | 1/2008 |
| ES | 2289542 | T3 | 2/2008 |
| ES | 2315505 | T3 | 4/2009 |
| GB | 1147210 | A | 4/1969 |
| GB | 1567727 | A | 5/1980 |
| GB | 2047095 | A | 11/1980 |
| GB | 2057878 | A | 4/1981 |
| GB | 2238478 | A | 6/1991 |
| HR | 20070456 | T3 | 6/2007 |
| HR | 20070272 | T3 | 11/2007 |
| JP | S36-022895 | | 11/1961 |
| JP | S55162714 | A | 12/1980 |
| JP | S5659708 | A | 5/1981 |
| JP | 556169622 | A | 12/1981 |
| JP | S62240061 | A | 10/1987 |
| JP | H0249719 | A | 2/1990 |
| JP | 03-501737 | A | 4/1991 |
| JP | H0517566 | A | 1/1993 |
| JP | H06507645 | A | 9/1994 |
| JP | 08053331 | A | 2/1996 |
| JP | 8-505076 | A | 6/1996 |
| JP | H09508410 | A | 8/1997 |
| JP | H1057450 | A | 3/1998 |
| JP | H10251149 | A | 9/1998 |
| JP | 2000513333 | A | 10/2000 |
| JP | 2002524150 | A | 8/2002 |
| JP | 2002-275175 | | 9/2002 |
| JP | 2003113119 | A | 4/2003 |
| JP | 2003125706 | A | 5/2003 |
| JP | 2003526598 | A | 9/2003 |
| JP | 2004143071 | A | 5/2004 |
| JP | 2004530676 | A | 10/2004 |
| JP | 2005506965 | A | 3/2005 |
| JP | 2005515152 | A | 5/2005 |
| JP | 2005534664 | A | 11/2005 |
| JP | 2006506374 | A | 2/2006 |
| JP | 1254634 | B | 5/2006 |
| JP | 2007501201 | A | 1/2007 |
| JP | 2007501202 | A | 1/2007 |
| JP | 2007513147 | A | 5/2007 |
| JP | 2007533692 | A | 11/2007 |
| JP | 2008024603 | A | 2/2008 |
| JP | 2008504327 | A | 2/2008 |
| JP | 2008528654 | A | 7/2008 |
| JP | 2009523833 | A | 6/2009 |
| JP | 2009524626 | A | 7/2009 |
| JP | 2009531453 | A | 9/2009 |
| JP | 2009536927 | A | 10/2009 |
| JP | 2009537456 | A | 10/2009 |
| JP | 2010505949 | A | 2/2010 |
| JP | 2010527285 | A | 8/2010 |
| JP | 2010534204 | A | 11/2010 |
| JP | 2011504455 | A | 2/2011 |
| JP | 2011506493 | A | 3/2011 |
| JP | 2011510034 | A | 3/2011 |
| JP | WO 2011/059074 | A1 | 5/2011 |
| JP | 2012515735 | A | 7/2012 |
| JP | 2012528845 | A | 11/2012 |
| JP | 2013523804 | A | 6/2013 |
| JP | 2013155124 | A | 8/2013 |
| JP | 2013536810 | A | 9/2013 |
| JP | 2014505736 | A | 3/2014 |
| JP | 2014-524925 | A | 9/2014 |
| JP | 2014528437 | A | 10/2014 |
| JP | 6085307 | B2 | 2/2017 |
| JP | 2013523780 | A | 6/2017 |
| KR | 1020060069832 | A | 6/2006 |
| KR | 20070039041 | A | 4/2007 |
| KR | 20070111510 | A | 11/2007 |
| KR | 20090085312 | A | 8/2009 |
| KR | 20100111303 | A | 10/2010 |
| KR | 20110016921 | A | 2/2011 |
| MX | 2007000008 | A | 3/2007 |
| MX | 2007000009 | A | 3/2007 |
| MX | 2007009393 | A | 8/2007 |
| MX | 2010008138 | A | 8/2010 |
| MX | 2010012039 | A | 11/2010 |
| NO | 20061054 | A | 3/2006 |
| NO | 20070578 | A | 1/2007 |
| NO | 20074412 | A | 11/2007 |

(56) References Cited

FOREIGN PATENT DOCUMENTS

| | | | |
|---|---|---|---|
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A1 | 9/1999 |
| WO | WO 1999/047481 A1 | 9/1999 |
| WO | WO 00/15261 * | 3/2000 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 8/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 5/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/013479 A1 | 12/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A1 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/002553 A2 | 1/2005 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 B1 | 1/2006 |
| WO | WO 2006/002886 A1 | 1/2006 |
| WO | WO 2006/002884 B1 | 3/2006 |
| WO | WO 2006/024881 A2 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |

(56) References Cited

FOREIGN PATENT DOCUMENTS

| | | |
|---|---|---|
| WO | WO 2007/131357 A1 | 11/2007 |
| WO | WO 2007/138466 A2 | 12/2007 |
| WO | WO 2007/149438 A2 | 12/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069941 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083894 A1 | 7/2010 |
| WO | WO 2010/088911 A1 | 8/2010 |
| WO | WO 2010/083843 A1 | 9/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009604 A1 | 1/2011 |
| WO | WO 2011/009603 A1 | 2/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 4/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050639 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/158810 A1 | 10/2013 |
| WO | WO 2013/167735 A1 | 11/2013 |
| WO | WO 2013/025449 A1 | 3/2014 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/023675 A2 | 2/2015 |
| WO | WO 2015/048597 A1 | 4/2015 |
| WO | WO 2015/103379 A1 | 7/2015 |
| WO | WO 2015/120201 A1 | 8/2015 |
| WO | WO 2017/178658 A1 | 10/2017 |

OTHER PUBLICATIONS

Fitzpatrick, John. "The Influence of Superdisintegrants on Immediate Release," Pharmaceutical Technology Europe 2011; 23(6):3 pages. (Year: 2011).*
Claffey et al. Chem. Res. Toxicol. 2001, 14: 1339-1344. (Year: 2001).*
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
USP Expert Council, US Pharmacopoeia, Chapter 1092, 2007, 1-15.
2.9 Methoden der pharmazeutischen Technologie, European Pharmacopeia, 143-144, 1997. (Full English translation attached).
Albertini, B. "New spray congealing atomizer for the microencapsulation of highly concentrated solid and liquid substances" European Journal of Pharmaceutics and Biopharmaceutics 69 (2008) 348-357.
Alekseeva et al, Chemical-Pharmaceutical Journal, vol. 41, No. 9, 2007, 49-52. (Full translation attached.).
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90,1993.
Application of a modelling system in the formulation of extended release hydrophilic matrices, Reprinted from Pharmaceutical Technology Europe, Jul. 2006.
Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J.OrgChem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide)' in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug., 1987, vol. 102, No. 4, p. 426-429.
Bingwen et al, 2008, p. 367. (full translation attached).

(56) References Cited

OTHER PUBLICATIONS

Block, Lawrence. Medicated Applications. Chapter 88. In Remington's Pharmaceutical Sciences, 17th Ed, 1985.
Borquist et al., "Simulation of the release from a multiparticulate system validated by single pellet and dose release experiements," J. Controlled Release, 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic elivery of 5-aminosalicylic acid, European Journal of Pharmaceutics and Biotharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).
Cuesov, Drug Production Technology, Khar'kov, 1999, pp. 351-352. (Full translation attached.).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis et al, Effects of Excipients on Swelling and Drug Release from Compressed Matrices, in Drug Development and Industrial Pharmacy 23(1):107-112, Jan. 1997, Abstract.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, dated Sep. 24, 2012.
European Search Report and Opinion Application No. 14176277.3-1460, dated Dec. 15, 2014.
European Search Report and Opinion, Application No. 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.8-1219, dated Jun. 26, 2012.

(56) References Cited

OTHER PUBLICATIONS

European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric aterials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, Nl, vol. 86, No. 2, Apr. 5, 2011, pp. 275-284.
Guidance for Industry—Bioavailability and Bioequivalence—Studies for Orally Administered Drug Products—General Considerations , FDA, BP, Announced in the Federal Register: vol. 68, No. 53/Mar. 19, 2003.
Guidance for Industry—Statistical Approaches to Establishing Bioequivalence , FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(0), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 in Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.

(56) References Cited

OTHER PUBLICATIONS

Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 in Remington's Pharmaceutical Sciences, 17th Ed, 1985.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents ony).
Longer et al. Sustained-Release Drug Delivery Systems. Chapter 92. pp. 1611-1661 in Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review, vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).

Miller "To crush or not to crush? What to consider before giving medications to a patent with a tube or who has trouble swallowing", Nursing, pp. 50-52, Feb. 2000.
Mises à0 jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from Internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene-oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)"Journal of Controlled Release 58, pp. 87-95, 1999.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.

(56) References Cited

OTHER PUBLICATIONS

PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Oct. 1991, 8(10), S-192.
Pharm. Research, Official Journal of the American Association of Pharmaceutical Scientists, Sep. 1989, 6(9), S-98.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release. 2000, vol. 67, pp. 67-78.
Pinto, Joao F. et al. "Evaluation of the Potential Use of Poly(ethylene oxide) as Tablet-and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msdssearch.dow.com/PublishedLiteratureDOWCOM/dh_0031/0901b80380031a4a.pdf?filepath=/326-00001.pdf&fromPage=GetDoc).
POLYOX WSR-303, retrieved Mar. 10, 2014 from URL http://www.dow.com/dowwolff/en/industrial_solutions/polymers/polyethylne.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al, Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.
Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 in Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomerc 3-Dialkylaminopropanols and O-Derivatives, J.f. prakt. Chemie, 323:5, 793-800 (1981).

(56) References Cited

OTHER PUBLICATIONS

Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Tennant, "Simultaneous Use of Stimulants and Opioids," 2011 [online] retrieved on Jul 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.

Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. Pages 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and the Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart-N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart-N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. I 14-Dihydroxydihydromorphinone," J. Am. Chem. Soc. 77, pp. 5891-5892, Nov. 20, 1955.
West, Anthony R., Solid state chemistry and its applications, Wiley, New York, 1988, pp. 358 and 365.
Wikipedia-Dextromethorphan Aug. 12, 2013 (and attached related English-language entry dated Dec. 11, 2013).
Woodburn, K.R. et al., Vascular complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.

(56) References Cited

OTHER PUBLICATIONS

Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract only) (Jul. 24, 1986).
Yeh et al., Stability of Morphine in Aqueous Solution III: Kinetics of Morphine Degradation in Aqueous solution, Wiley Subscription Services, Inc., Journal of Pharmaceutical Sciences, 50(1): 35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Decision of the United States District Court for the Southern District of New York, in in re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in in re Oxycontin Antitrust Litigation, *Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacal. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerto.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, in (2000).
CROWLEY0000001-CROWLEY0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts At Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).
Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).

(56) References Cited

OTHER PUBLICATIONS

Larhib, H. et al., "Compressing polyethyelene glycols: the effect of compression pressure and speed," Int'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. Al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
Polyox Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version 16—Sep. 10; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph.D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compresses Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide in Rubber-Like State." Journal of Physical Chemistry, 1961. 65(3): 534-538.
Zacny, J. et al. Drug & Alcohol Dependence (2003) 69:215-232.
Hang, F., "Hot-Melt Extrusion as a Novel Technology to Prepare Sustained-Release Dosage Forms," Dissertation University of Texas at Austin, Dec. 1999.
Furu et al. "use of ADHD drugs in the Nordic countries: a population-based corriparison study," Acta Psychiatrica Scandinavia, May 2010.
PCT International Search Report and Written Opinion for PCT Application No. PCT/EP2017/070396 dated Sep. 8, 2917.
M. Xu et al., "Evaluation of the coat quality of sustained release pellets by individual pellet dissolution methodology," Int. J. Pharm. 478 (2015) 318-827.
Extended European Search Report for Application No. EP 16183922.0-1460, dated Oct. 31, 2016.
Fathima, N. et al. "Drug-excipient interaction and its importance in dosage form development," Journal of Applied Pharmaceutical Science 01 (06); 2011, pp. 66-71.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035.
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Koziolek, M. et al., "Development of a bio-relevant dissolution test device simulating mechanical aspects present in the fed stomach," European Journal of Pharmaceutical Sciences 57 (2014) 250-256.
Remington, Chapter 45, pp. 996-1035. (Full Translation Attached).
COMPAP 90 technical data sheet Mar. 2014; 1 page.
Extended Europrean Search Report for Application No. EP 161821244-1455, dated Jan. 17, 2017.
Turkington, R., "Amphetamines," in Chemicals used for illegal Purposes. A Guide for first Responders to Identify Explosives, Recreational Drugs, and Poisons, 2010, p. 247.
U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.
King, Remington's Pharmaceutical Sciences 17th ed., Chapter 78, p. 1418-1419 (1985).
Pharma Tips ([online] retrieved on Mar. 22, 2018 from http://ww.pharmatips.in/Articles/Pharmaceutics/Tablet/Co-Processed-Directly-Compressed-Adjutants.aspx May, 2011: 10 pages).
De Brabander C., et al., "Development and evaluation of sustained release mini-matrices prepared via hot melt extrusion," Journal of Controlled Release 89 (2003), 235-247.
Goodman and Gilman, 1985, 7th edition, chapter 29, 674-715.
Quadros, E. et al., "Evaluation of a novel colonic delivery device in vivo," STP Pharma Sci. 5, 77-82 (1995).
Wooten, Marvin R. et al., Intracerebral Hemorrhage and Vasculitis Related to Ephedrine Abuse, 13 Annals of Neurology 337 (1983).
Theeuwes, Felix et al., Osmotic Systems for Colon-Targeted Drug Delivery in Colonic Drug Absorption and Metabolism (Peter R. Bieck ed., 1993).

(56) References Cited

OTHER PUBLICATIONS

European Pharmacopoeia 3.0, 2.9.8 "Resistance to Crushing of Tablets", 1997, p. 135.
Nickerson, B., Sample Preparation of Pharmaceutical Dosage Forms, Springer, New York (2011); Chapter 1, pp. 3-48.
PCT International Search Report and Written Opinion for PCT Application No. PCT/EP2016/052046 dated Apr. 12, 2016.
Sigma-Aldrich entry for CAS No. 9010-88-2; www.sigmaaldrich.com/catalog/product/aldrich/182249?lang.en®ion=US (downloaded Jun. 2018).
Sumitomo Seika Chemicals, Co., Ltd, "Certificate of Analysis," Product: Polyethylene Oxide; Grade: PEO-18NF; Feb. 2, 2016.
Sumitomo Seika Chemicals, Co., Ltd, "Certificate of Analysis," Product: Polyethylene Oxide: Grade: PEO-20NF; May 15, 2013.
Sumitomo Seika Chemicals, Co., Ltd, "Certificate of Analysis," Product: Polyethylene Oxide; Grade: PEO-20NF; Jan. 23, 2012.
Sumitomo Seika Chemicals, Co., Ltd, "Certificate of Analysis," Product: Polyethylene Oxide; Grade: PEO-20NF; Feb. 3 2016.
POLYOX Water-Soluble Resins in Pharmaceutical Applications. Dow Chemicals. Published 2004.
Houston, T.E., et al., "Bite Force and Bite Pressure: Comparison of Humans and Dogs," http://www.glapbta.com/BFBP.pdf, 2003, pp. 1-7.
Pintauro, Nicholas, D., Food Flavoring Processes, Table of Content, Park Ridge, NJ and London, UK, 1976.
European Pharmacopeia, 7th Ed. 2.2.8 and 2.2.10, 27ff, 2008.
Ely et al., "Lithium-Ammonia Reduction of Ephedrine to Methamphetamine: An Unusual Clandestine Synthesis," Technical Note, 1990, 720-723.
Jedinger, N., et al., Eur. J. Pharm: Biopharm 87 (2014), 217-226.
Kunalan et al., "Investigation of the Reaction Impurities Associated with Methylamphetamine Synthesized using the Nagai Method," Anal. Chem. 2012, 84, 5744-52.
Lee et al., "Analysis of the impurities in the metamphetamine synthesized by thee, different methods from ephedrine and pseudoephedrine," Forensic Science International 161 (2006), 209-215.
Person et al., Structural Determination of the Principal Byproduct of the Lithium-Ammonia Reduction Method of Methamphetamine Manufacture, J Forensic Sci, Jan. 2005, vol. 50, No. 1, 87-95.
Polyox, 2004, online retrieved on Oct. 15, 2018.
Salouros et al., Isolation and Identification of Three By-Products Found in Methylamphetarnine Synthesized by the Emde Route2010 605-615.
Skinner, Harry F., "Methamphetamine Synthesis via Hydriodic Acid/Red Phosphorus Reduction of Ephedrine," Forensic Science International, 48 (1990), 123-134.
Agarwal, G, et al, "Oral Sustained Release Tabets: An Overview with a Special Emphasis on Matrix Tablet," American Journal of Advanced Drug Delivery, 2017.
Brzeclo et al., "The Advent of a new Pseudoephedrine Product to Combat Methamoatarnine Abuse," Am J Drug Alcohol Abuse, 2013: 39(5): 284-290.
Extended European Search Report for Application No. EP 17173240.7, dated Nov. 28, 2017.
Jamini, M., et al, "Sustained Release Matrix Type Drug Delivery System: A Review," Journal of Drug Delivery & Therapeutics; 2012, 2(6), 142-148.
Kelly, C. et al, "Methamphetamine Synthesis Inhibition: Dissolving Metal Reductions," Johns Hopkins Univ. Applied Physics Lab,. 2015, 1-10.
"Low Substituted Hydroxypropyl Celluslose", Drugs.com, from https://www.drugs.com/inactive/low-susbstitute-hydroyprepyl-cellulose-581.html (2018).
Misal, R, et al., "Matrix Tablet: A Promising Technique for Controlled Drug Delivery," Indo American Journal of Pharmaceutical Research, 2013.
Patel, et al., "Poloxamers: A pharmaceutical excipient with therapeutic behaviors," PharmTech, vol. 1, No. 2, pp. 299-300 (Apr. 2009).
Patrick, K., et al., "Pharmacology of Methylphenidate, Amphetamine Enantiomers and Pemoline in Attention-Deficit Hyperactivity Disorder," Human Psychopharmacology, vol. 12, 527-546 (199).
Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis , 2018, 16-22.
Qi et al, "An Investigation into the Crystallisation Behavior of an Amorphous Cryomilled Pharmaceutical Material Above and Below the Glass Transition Temperature, " Journal of Pharmaceutical Sciences, 2009, 196-208.
Sprockel, et. al, "A melt-extrusion process for manufacturing matrix drug delivery systems," Int. Journal of Pharmaceutics 155 (1997) 191-199.
Targin(R) Product Monograph. Purdue Pharma. Revised Mar. 1, 2016.
Vezin, W. et al, "Adjustment of precompression force to reduce mixing-time dependence of tablet tensile strength," J. Pharm. Pharmacol. 1983, 35: 555-558 (Mar. 28, 1983).
BASF the chemical company, Kollicoat IR Technial information, Feb. 2013, p. 1-14 (2013).
Domino E.F. (1991) Nicotine: A Unique Psychoactive Drug. In: Adlkofer F., Thurau K. (eds.) Effects of Nicotine on Biological Systems. APS Advances in Pharmacological Sciences. Birkhaeuser Basel (1991).
Kolar et al., "Treatmen of adults with attention-deficit/hyperactivity disorder," Neuropsychiatric Disease and Treatment 2008:4(3):389-403.
Rasmussen, N. "America's First Amphetamine Epidemic 1929-1971," American Journal of Public Health 2008:98(6): 974-985.
Weinhold, et al. "Buprenorphine alnoe and in combination with naloxone in non-dependent humans." Drug & Alcohol Dependence 30.3 (1992): 263-274.
Befort et al., "The Conserved Asparatate Residue in the Third Putative Transmember Domain," Molecular Pharmacology 1996: 49:216-223 (1996).
Fitzpatrick, J., "The influence of Superdisintegrants on Immediate Release," By Pharmaceutical Technology Editions [online] retrieved from http://www.pharmatech.com/influence-superdisintegrants-immediate-release; vol. 21, issue 6 (Jun. 1, 2011).
Suzuki, T, "Blood-brain barrier transport of opioid analgesics," Abstract, Yakugaki Zasshi; 131(10): 1445-51 (2011).
Gaitondf, B. "General Principles of Drug Action", 1967, p. 48.
Evekeo, (Amphetame Sulfate) for treating patients with ADHD website ([online]https://www.evekeo.com.about-evekeo; 2019:5 pages), 2019.
Lurie et al., "Chiral Resolution of Cationic Drugs of Forensic Interest," (Analytical Chemistry 1994; 66(22): 4019-4026.
Evans, J.C, et. Al. "Optimal tocopherol concentrations to inhibit soybean oil oxidation," Journal of the American Oil Chemists' Society 79.1 (2002): 47-51.
Quinn, M.E. "Alpha Tocopherol" in Handbook of Pharmaceuical Excipients, Sixth Edition (2009), 31-33.
Romach et al. "Update on tamper-resistant drug formulations," Drug and Alcohol Dependence, 130 (2013), 13-23.
Claffey et al, "Amphetamine Adducts of Melanin Intermediates Demonstrated by Matrix-Assisted Laser Desorption Ionization Time-of-Flight Mass Spectrometry," Chem. Res, Toxicol. 2001, 14, 1339-1344.
Martin et al., Applications of Polyethylene Oxide (POLYOX) in Hydrophilic Matrices, Inc. Hydrophilic Matrix Tablets for Oral Controlled Release, Springer, New York, 2014, Chapter 5, pp. 123-141.
Thumma et al., "Influence of Plasticizers on the Stability of a Prodrug of D9-Tetrahydrocannabinol Incorporated in poly(Ethyelen Oxide) Matrices", Eur J. Pharm Biopharm. Oct. 2008 (70(2): 605-614.
Vosburg, et al., "A comparison among tapemadol tamper-resistant formulations(TRF) and OxyCotin® (non-TRF) in prescription opioid abusers," 2013; Society for the Study of Addiction; Addiction, vol. 108, pp. 1095-1106.

(56) References Cited

OTHER PUBLICATIONS

Heal et al. "Amphetamine, past and present—a pharmacological and clinical perspective," Journal of Psychology 2013:27(6):479-496 (2013).
Lefnaoui et al., Synthesis and evaluation of the structural and physiochemical properties of carboxymethyl pregelatinized starch as a pharmaceutical excipient, Saudi Pharmaceutical Jourani, Feb. 2015:23:698-711 (2015).
Lopez-Solis et al., Effect of disintegrants with different hygroscopicity on dissolution of Norfloxacin/Pharmatose DCL 11 tablets, International Journal of Pharmaceutics 2001:216:127-135 (2001).
Nagar et al, "Orally disintegrating tablets : formulation, preparation techniques and evaluation," Journal of Applied Pharmaceutical Science 2011: 01(04): 35-45 (2011).
Hedaya, M. et al. "The Need for Tamper-Resistant and Abuse-Deterrent Formulations," J. Pharma Care Health Systems, vol. 1, Issue 1 (2014).
Mastropietro, D. et al. "Current approaches in tamper-resistant and abuse-deterrent formulations." Drug Development and Industrial Pharmacy, vol. 39(5), pp. 611-624 (2013).
Wolff, K. et al. "Screening for Drugs of Abuse: Effect of Heat-Treating Urine for Safe Handling of Samples", Clinical Chemistry, vol. 36, No. 6, 1990.

\* cited by examiner

PROTECTING ORAL OVERDOSE WITH ABUSE DETERRENT IMMEDIATE RELEASE FORMULATIONS

This application claims priority of European patent application no. 15 184 634.2 that was filed on Sep. 10, 2015.

The invention relates to a pharmaceutical dosage form which is particularly useful for the prevention of an overdose of the pharmacologically active ingredient contained therein after accidental or intentional simultaneous administration of a plurality of the dosage forms containing an overall supratherapeutic dose of the pharmacologically active ingredient.

A large number of drugs have a potential for being abused or misused, i.e. they can be used to produce effects which are not consistent with their intended use. Examples of commonly abused drugs include psychoactive drugs, anxiolytics, sedative hypnotics, stimulants, depressants, and analgesics such as narcotic analgesics, among others. In particular, drugs which have a psychotropic effect, e.g. opioids, morphine derivatives, barbiturates, amphetamines, ketamine, and other drugs, are abused to induce euphoric states similar to being intoxicated, and can cause psychological or physical dependence.

Some common techniques for intentionally abusing a drug begin with an abuser obtaining a solid dosage form such as an orally administered tablet or capsule, and crushing the solid dosage form into a powder. The powder may be administered by an abuser by nasal insufflation (i.e., "snorting") to introduce the drug to the abuser's bloodstream intranasally. Alternately, the crushed dosage form may be combined with a solvent that is capable of dissolving the drug, and the solvent with the dissolved drug may be injected directly into an abuser's bloodstream. This type of administration results in an even faster diffusion of the drug compared to the oral abuse, with the result desired by the abuser, namely the kick.

Various concepts for the avoidance of drug abuse have been developed. It has been proposed to incorporate in dosage forms aversive agents and/or antagonists in a manner so that they only produce their aversive and/or antagonizing effects when the dosage forms are tampered with. However, the presence of such aversive agents, e.g. bitter substances, irritants, colorants, emetics, and the like is principally not desirable and there is a need to provide sufficient tamper-resistance without relying on aversive agents and/or antagonists.

Another concept to prevent abuse relies on the mechanical properties of the pharmaceutical dosage forms, particularly an increased breaking strength (resistance to crushing). The mechanical properties, particularly the high breaking strength of these pharmaceutical dosage forms renders them tamper-resistant. The major advantage of such pharmaceutical dosage forms is that comminuting, particularly pulverization, by conventional means, such as grinding in a mortar or fracturing by means of a hammer, is impossible or at least substantially impeded. Thus, the pulverization, necessary for abuse of the dosage forms, by the means that are usually available to a potential abuser is prevented or at least complicated. Such pharmaceutical dosage forms are useful for avoiding drug abuse of the drug contained therein, as they may not be powdered by conventional means and thus, cannot be administered in powdered form, e.g. nasally. In the context of such break resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, WO 2008/107149, WO 2009/092601, WO 2011/009603, WO 2011/009602, WO 2009/135680, WO 2011/095314, WO 2012/028317, WO 2012/028318, WO 2012/028319, WO 2011/009604, WO 2013/017242, WO 2013/017234, WO 2013/050539, WO 2013/127830, WO 2013/072395, WO 2013/127831, WO 2013/156453, WO 2013/167735, WO 2015/004245, WO 2014/191396, and WO 2014/191397.

Still another concept to prevent abuse relies on the presence of auxiliary substances that increase the viscosity of the resultant composition when the dosage forms are tampered with, e.g. when they are subjected to liquids in order to prepare formulations for parenteral administration, e.g. intravenous injection. Said auxiliary substances increase the viscosity of the resultant compositions to such an extent that the liquids cannot be drawn-up in syringes. While it may be possible to extract the drug from the dosage form at least to a certain extent, the extract is not useful for subsequent abuse.

WO 2015/103379 A1 discloses abuse-resistant, immediate-release liquid pharmaceutical compositions comprising a mixture of an effective amount at least one pharmaceutically active agent susceptible to abuse, an organic vehicle, a surfactant, a co-solvent, and optionally a viscosity-building polymer; wherein said organic vehicle, surfactant, and co-solvent co-elute with the pharmaceutically active agent when exposed to a solvent, and wherein the viscosity-building polymer is present in an amount that slows the release of the pharmaceutically active agent if multiple unit doses of the composition are administered. The compositions shall reduce the likelihood of improper administration of drugs that are susceptible to abuse. The compositions contain abuse deterrent agents that cause discomfort to the user when administered in an improper manner and make the extraction of an active ingredient more difficult.

Alternatively, with immediate release oral dosage forms, an abuser might simply ingest multiple units (e.g., tablets) of the dosage form together, e.g., simultaneously. Each one of the multiple dosage form units—immediately releases an amount of drug to produce a short-term concentration spike of the drug in the user's bloodstream and a desired "high" in the user.

WO 2008/107149 discloses a multiparticulate pharmaceutical form with impeded abuse including at least one active ingredient with the potential for abuse (A), at least one synthetic or natural polymer (C), optionally at least one natural, semi-synthetic, or synthetic wax (D), at least one disintegrant (E), and optionally one or more additional physiologically tolerable excipients (B), wherein the individual particles of the pharmaceutical form have a breaking strength of at least 500 N and an active ingredient release of at least 75% after 45 minutes, measured according to Pharm. Eur. in the paddle mixer with a sinker in a 600 ml aqueous buffer solution with a pH value of 1.2 at 37° C. and 75 revolutions per minute.

WO 2013/017242 and WO 2013/017234 relate to a tamper-resistant tablet comprising a matrix material in an amount of more than one third of the total weight of the tablet; and a plurality of particulates in an amount of less than two thirds of the total weight of the tablet; wherein said particulates comprise a pharmacologically active compound and a polyalkylene oxide; and form a discontinuous phase within the matrix material.

US 2015 0118300 A1 discloses oral dosage forms that contain abuse-deterrent features and that contain core-shell polymers that include an active pharmaceutical ingredient, with particular examples including immediate release dosage forms that contain a drug that is commonly susceptible to abuse.

US 2015 0118302 A1 and US 2015 0118303 A1 disclose immediate release oral dosage forms that contain abuse-deterrent features. In particular, the disclosed dosage forms provide deterrence of abuse by ingestion of multiple individual doses. In addition, the disclosed dosage forms provide protection from overdose in the event of accidental or intentional ingestion of multiple individual doses. The dosage forms have a relatively complex construction of a) core-shell particles comprising: a core; an active pharmaceutical layer surrounding the core; at least one layer surrounding the active pharmaceutical layer, the at least one layer comprising a pH-sensitive film comprising pH-sensitive polymer that is insoluble in water at a pH greater than 5 and is soluble in water at a pH below 5; and b) a matrix comprising a disintegrant and a gelling polymer.

The properties of conventional tamper-resistant dosage forms are not satisfactory in every respect. The requirements for tamper-resistant dosage forms that nowadays need to be satisfied are complex and sometimes are difficult to be combined and arranged with one another. While a certain measure may improve tamper-resistance in a certain aspect, the same measure may deteriorate tamper-resistance in another aspect or otherwise may have a detrimental effect on the properties of the dosage forms.

Although the pharmaceutical industry has identified a variety of abuse deterrent features useful with oral dosage forms, there is continuing need to improve and identify new abuse deterrent features to inhibit or prevent abuse or overdosing of active pharmaceutical ingredients.

It is an object of the invention to provide pharmaceutical dosage forms having advantages compared to the pharmaceutical dosage forms of the prior art. The pharmaceutical dosage forms should be particularly useful for avoiding or preventing of an overdose of the pharmacologically active ingredient contained therein after accidental or intentional simultaneous administration of a plurality of the dosage forms containing an overall supratherapeutic dose of the pharmacologically active ingredient.

This object has been achieved by the subject-matter of the patent claims.

A first aspect of the invention relates to a pharmaceutical dosage form comprising a pharmacologically active ingredient a and a polymer matrix which comprises a polyalkylene oxide having an average molecular weight of at least 200,000 g/mol; preferably of at least 500,000 g/mol;
wherein preferably a single dosage form provides under physiological conditions fast release, more preferably immediate release of the pharmacologically active ingredient a; and
wherein at least a portion of the pharmacologically active ingredient a is contained in one or more particles A which comprise the polymer matrix in which the pharmacologically active ingredient a is embedded;
for use in the prevention of an overdose of the pharmacologically active ingredient a after accidental or intentional simultaneous administration of a plurality of the dosage forms containing an overall supratherapeutic dose of the pharmacologically active ingredient a.

Preferably, the overdose that is to be prevented is the result of an accidental or intentional simultaneous oral administration of a plurality of not-manipulated dosage forms, i.e. the plurality of dosage forms is preferably intact and with respect to an individual dosage form present in prescribed form. Preferably, the only deviation from the prescribed mode of administration and prescribed route of administration is the number of the administered dosage forms, namely a plurality of the dosage forms containing an overall supratherapeutic dose of the pharmacologically active ingredient a.

It has been surprisingly found that the dosage forms according to the invention provide deterrence against abuse by multi-tablet dosing (multi-dosage-form-dosing). More specifically, in vitro testing of dosage forms was performed by conducting dissolution testing of one or more dosage forms (tablets) in various volumes of 0.1N HCL maintained at 37° C. using a 25 rpm and 50 rpm paddle speed. At 25 rpm the amount (percentage per tablet) of pharmacologically active ingredient a (opioid) and pharmacologically active ingredient b (acetaminophen) released in the media is reduced with an increase in the number of tablets, whereas at 50 rpm this effect was less pronounced or could not be observed. The mixing conditions at 25 rpm are still not comparable with the conditions in the gastrointestinal tract under in vivo conditions (J. L. Baxter et al., Int J Pharm 292 (2005) 17-28; M. Koziolek et al., Eur J Pharm Sci 57 (2014) 250-256). Under in vivo conditions in the stomach pharmaceutical dosage forms are not subject to rotational movement but to compression forces. The data suggest that the dosage forms according to the invention are effective to prevent increased levels of drug uptake in an individual who would accidentally or intentionally ingest multiple tablets, preventing or reducing the risk of an intentional or unintentional overdose of the drug.

Accordingly, the dosage forms according to the invention provide a method of preventing a short-term concentration spike of the drug in the bloodstream of a patient who is prescribed the drug, or in the bloodstream of an abuser who consumes the drug for recreational purposes, in the event that a patient or the abuser intentionally or unintentionally consumes a supratherapeutic dose of the drug. In addition, dosage forms as described herein provide a method whereby a drug overdose may be prevented in the event that a patient intentionally or unintentionally consumes a supratherapeutic dose of the drug. By "supratherapeutic" is meant a dose that exceeds what would normally be prescribed for therapy, for example a dose in excess of four, five, six, seven, eight, nine, ten, eleven or twelve individual dose units (e.g., tablets, capsules, etc.).

Thus, the dosage formas according to the invention are useful for the prevention of an overdose of the pharmacologically active ingredient a after accidental or intentional simultaneous preferably oral administration of a plurality of the dosage forms containing an overall supratherapeutic dose of the pharmacologically active ingredient a.

Unexpectedly, the advantages of the dosage form according to the invention do not only affect the pharmacologically active ingredient a that is embedded in the polyalkylene oxide in particle(s) A, but also the optionally present pharmacologically active ingredient b that may be present elsewhere in the dosage form.

It has been surprisingly found that these advantages can be achieved by dosage forms that additionally are crush resistant, i.e. have an increased breaking strength, at least with respect to particle(s) A comprising the pharmacologically active ingredient a.

Some tamper-resistant dosage forms of the prior art have also been used to avoid an overdose of the drug contained therein. Said overdose, however, is not the result of a simultaneous administration of a plurality of the dosage forms containing an overall supratherapeutic dose of the drug (multi-tablet dosing), but the result of an acceleration of the release profile and/or the result of the change of the route of administration. When accelerating the release profile, e.g. by pulverizing a dosage form, and/or extracting a drug therefrom and administering the extract, the dose of the drug that was originally contained in the dosage form is absorbed by the organism in a faster manner thereby leading to a transient increase of the plasma level. Once a certain plasma level has been exceeded, an euphoric state can be achieved and this is usually desired by potential abusers. No plurality of dosage forms is needed in order to achieve such overdose, as a single dosage form already contains a sufficient dose of the drug that—once absorbed in a sufficiently fast manner—reaches excessive plasma levels. This type of overdose, i.e. this excessive plasma level, is conventionally prevented by providing dosage forms having an increased breaking strength such that they cannot be easily pulverized. Therefore, the type of overdose that is to be conventionally prevented substantially differs from the type of overdose that is to be prevented according to the invention.

The dosage forms according to the invention can be preferably formulated to provide an immediate release profile of the pharmacologically active ingredient a as well as of the optionally present pharmacologically active ingredient b, and can also be prepared to include effective or advantageous abuse deterrent features that are effective to deter abuse of the same (e.g., one that is commonly susceptible to abuse) that exhibits the immediate release profile. Thus, the dosage forms according to the invention combine immediate release with broad abuse resistance for multiple abuse modalities including multi-tablet dosing. The dosage forms according to the invention can provide an immediate release profile, and can at the same time include abuse deterrent features that provide general abuse deterrence or abuse resistance.

The dosage forms can also be more specifically characterized as resistant to certain common methods of abuse, such as 1) abuse by injection, 2) abuse by nasal insufflation, and 3) abuse by multi-tablet dosing by oral consumption, meaning simultaneous oral ingestion of multiple or excessive quantities of orally administered dosage forms such as tablets or capsules. The third mode of abuse, multi-tablet dosing, is particularly common with immediate release dosage forms and is particularly difficult to defend against by design of a dosage form structure or by formulation. Accordingly, that the dosage forms according to the invention can be effective to prevent or deter abuse (or even accidental overdose) by the mode of multi-tablet dosing is a particularly useful feature of the dosage forms according to the invention.

The concept underlying the dosage forms according to the invention provides a high degree in flexibility concerning dosage, release profile, tamper-resistance, patient compliance, ease of manufacture and the like. The dosage forms according to the invention can be prepared from a variety of components that are separately prepared. Specific selection of specific components from said variety of components allows for tailoring dosage forms satisfying a large variety of different requirements. For example, it is possible to make available a variety of three different types of particle(s) A that differ e.g. in their content of pharmacologically active compound a. When manufacturing pharmaceutical dosage forms according to the invention having a predetermined total dosage of pharmacologically active ingredient a, one may select different combinations of particles $A_1$, $A_2$ and $A_3$ in order to achieve said total dosage of pharmacologically active ingredient a. For example, particles $A_1$ may contain a dosage of 0.25 mg, particles $A_2$ may contain a dosage of 1.50 mg, and particles $A_3$ may contain a dosage of 3.50 mg, such that a total dosage of e.g. 5.00 mg pharmacologically active ingredient a can be achieved by 20 particles $A_1$;
2 particles $A_1$ in combination with 3 particles $A_2$;
1 particle $A_2$ in combination with 1 particle $A_3$; or
6 particles $A_1$ in combination with 1 particle $A_3$.

Another advantage of the concept underlying the dosage forms according to the invention is that nearly every combination may be either filled into capsules or may be compressed into tablets. This flexibility has particular advantages when providing tamper-resistant products that need to satisfy the confidence requirements with respect to the marketing authorization for the initial non-tamper-resistant product. Thus, the present invention makes available at a high degree of flexibility tamper-resistant counterparts to existent non-tamper-resistant products. If in initial tests the confidence intervals are not met, the present invention provides easy and predictable measures for slightly altering the properties of the dosage form in order to meet the confidence requirements.

FIG. 3 shows the in vitro release profiles of exemplified dosage forms with respect to the release of hydrocodone (pharmacologically active ingredient a) when testing a single dosage form, a multitude of 5 dosage forms and a multitude of 10 dosage forms expressed in mg of hydrocodone release per tablet.

FIG. 4 shows the in vitro release profiles of exemplified dosage forms with respect to the release of acetaminophen (pharmacologically active ingredient b) when testing a single dosage form, a multitude of 5 dosage forms and a multitude of 10 dosage forms expressed in mg of hydrocodone release per tablet.

Figure 5:
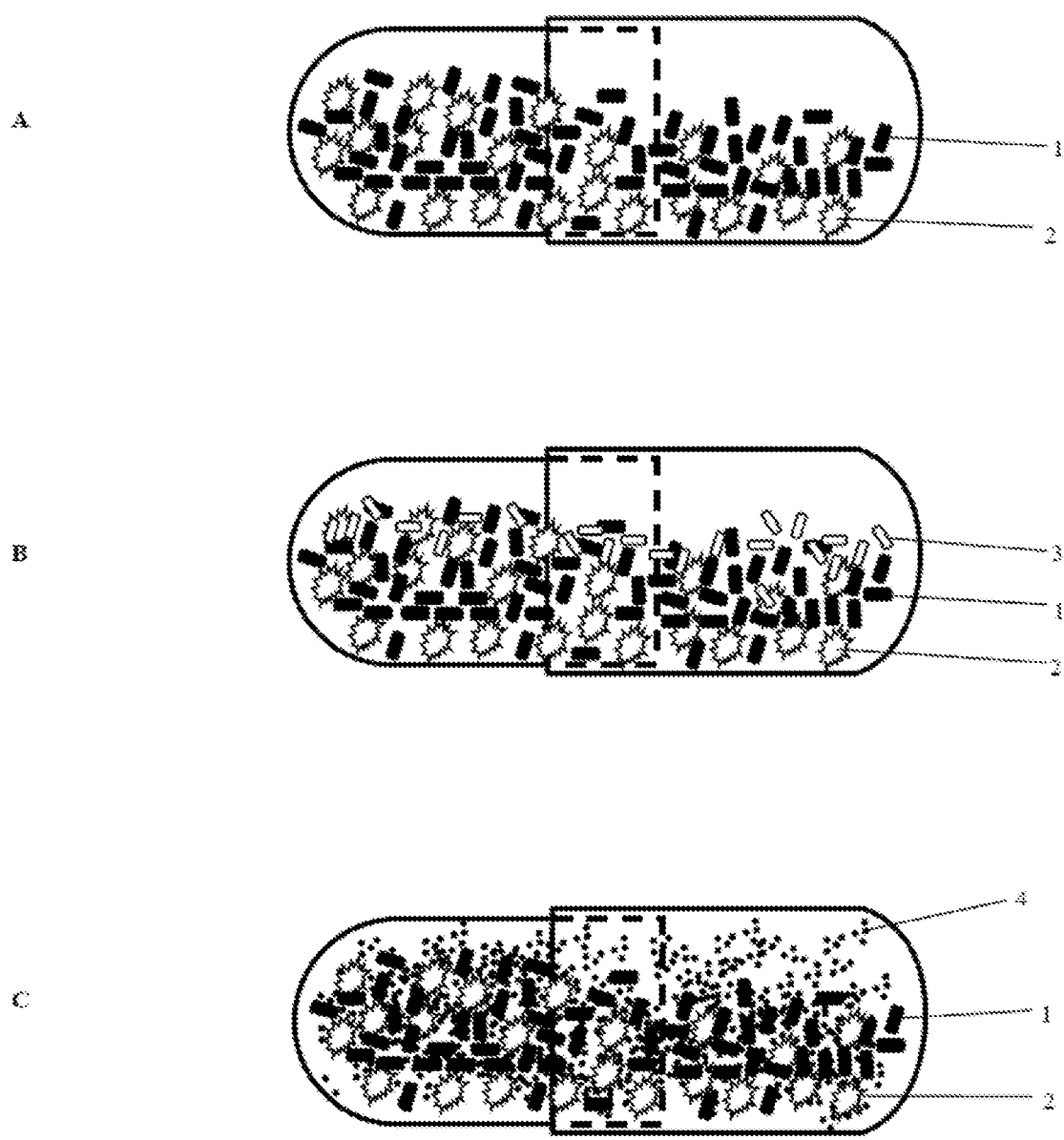
FIGS. 5 and 6 illustrate preferred embodiments of pharmaceutical dosage forms according to the invention that comprise two pharmacologically active ingredients a and b.

FIG. 5 illustrates preferred embodiments of pharmaceutical dosage forms according to the invention. FIG. 5A illustrates a capsule comprising a multitude of particles A (1) and pharmacologically active ingredient b that is contained outside the particles A in an outer matrix material, here shown in form of granules (2). Particles A (1) may additionally comprise a portion $b_A$ of pharmacologically active ingredient b and/or a coating comprising a portion $b_C$ of pharmacologically active ingredient b. The capsule according to FIG. 5B additionally comprises a portion $b_B$ of pharmacologically active ingredient b contained in particles B (3), whereas the capsule according to FIG. 5C additionally comprises a portion $b_P$ of pharmacologically active ingredient b in form of a powder (4); thus, according to this embodiment, the outer matrix material comprises granules (2) as well as powder (4).

Figure 6:
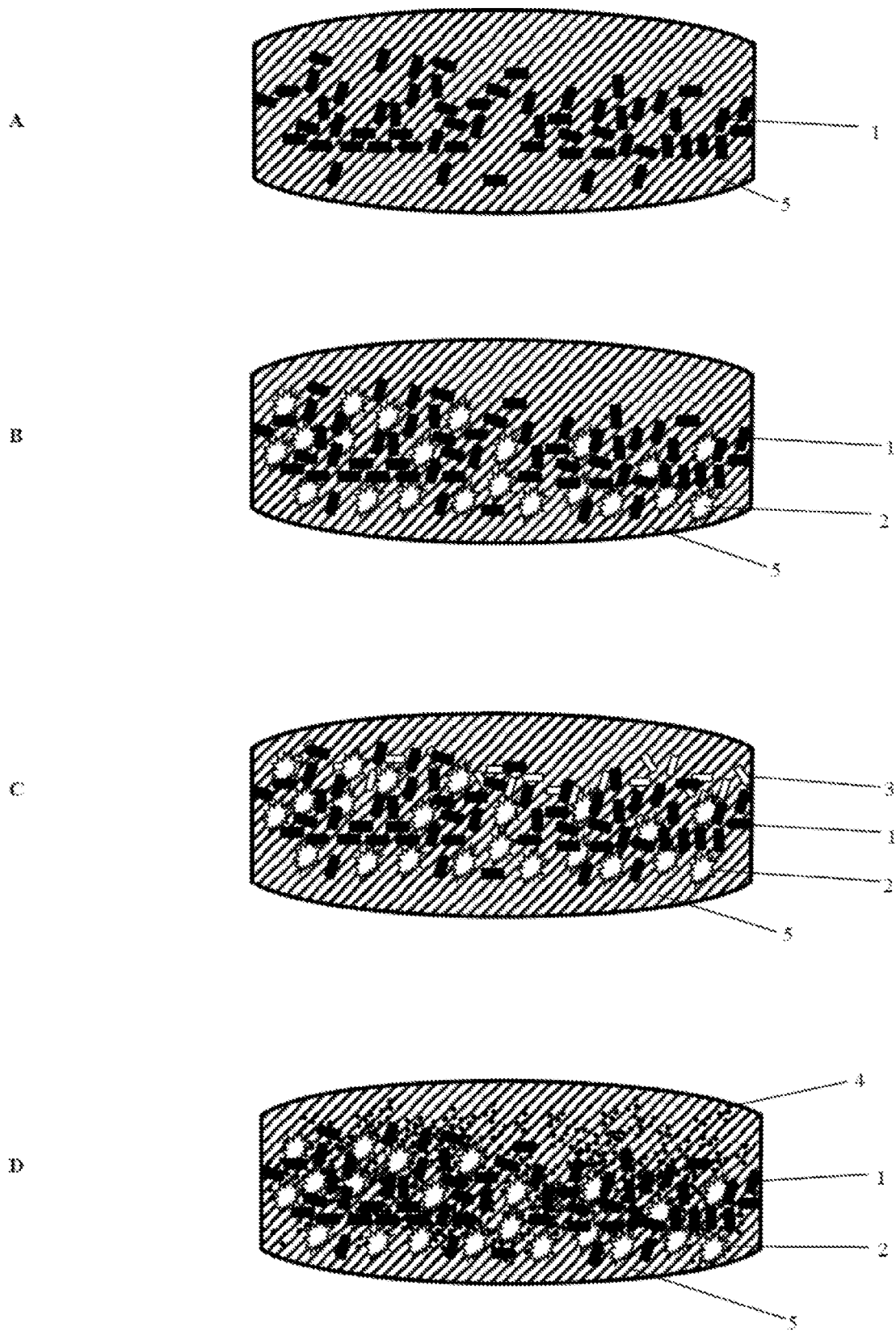

FIG. 6 illustrates the corresponding preferred embodiments of FIG. 5 where the dosage form is provided as a tablet comprising an outer matrix material (5) in which particles A (1), the optionally present granules (2), the optionally present particles B (3) and/or the optionally present powder are embedded. It is also possible that said outer matrix material (5) consists of granules (2), and the optionally present particles B (3) and/or the optionally present powder.

Figure 7:
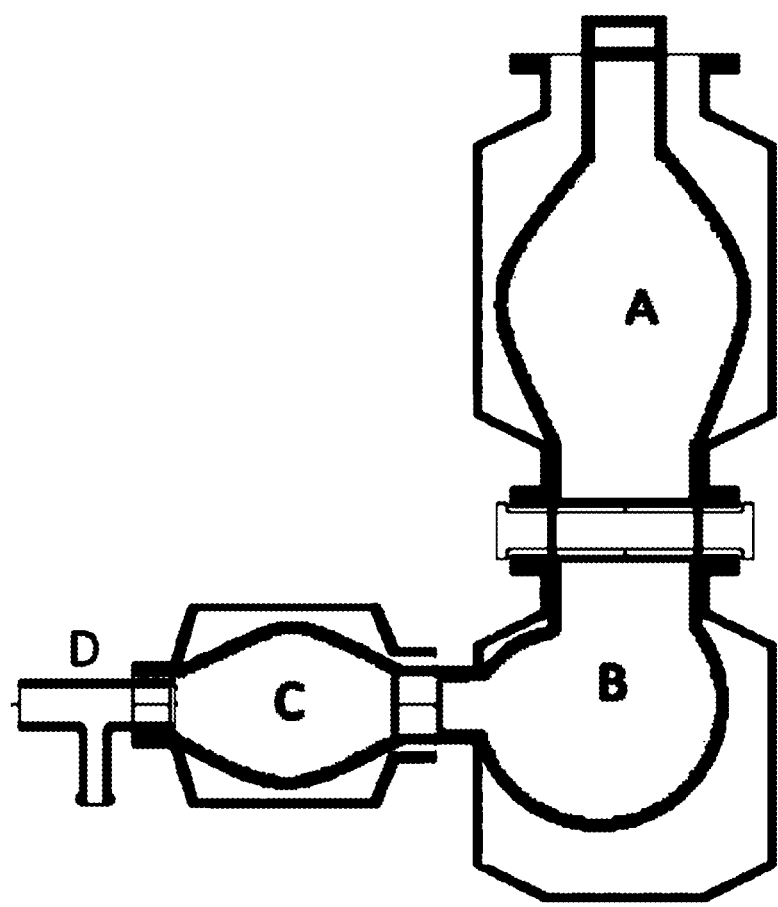

FIG. 7 schematically illustrates the TIMagc system that was used in Examples 2 and 3 (Inventive vs. Comparative).

Figure 8:
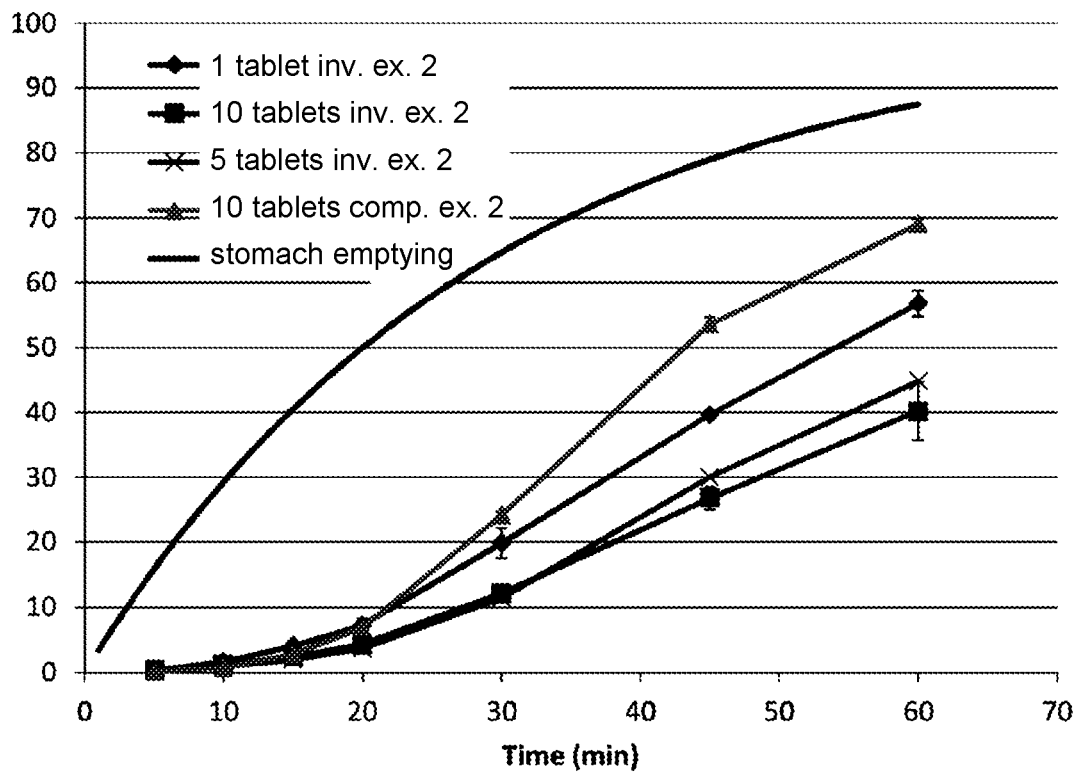

FIG. 8 illustrates a comparison of the fasted state experiments according to Example 2 for hydrocodone.

Figure 9:
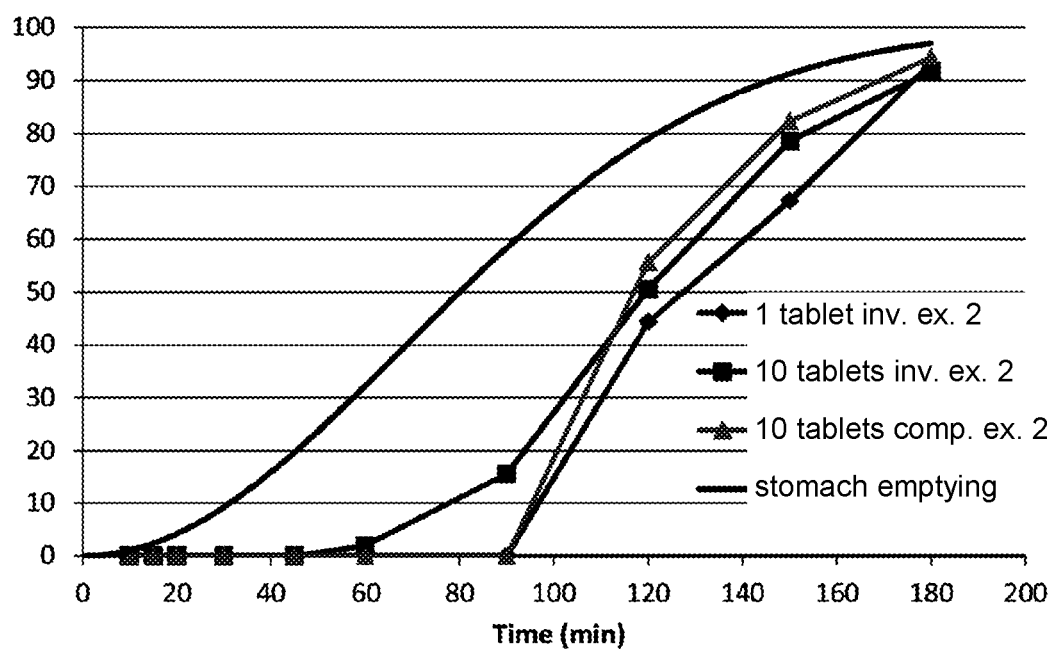

FIG. 9 illustrates a comparison of the fed state experiments according to Example 2 for hydrocodone.

Figure 10A:
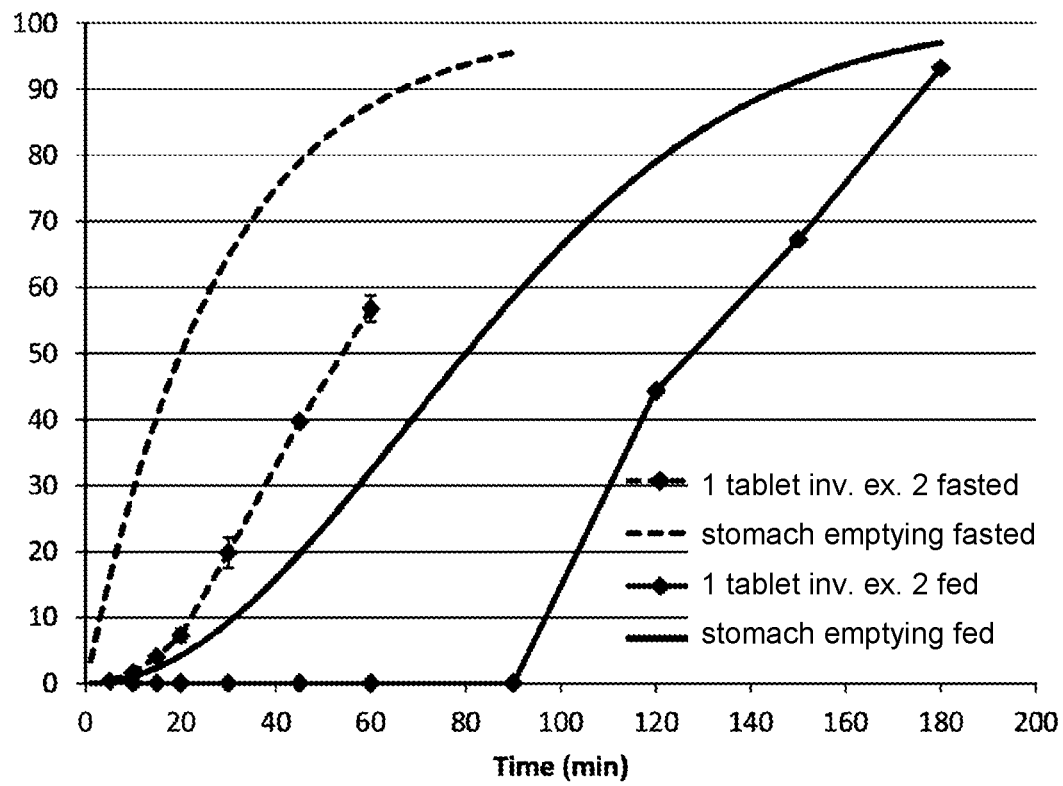
Figure 10B:
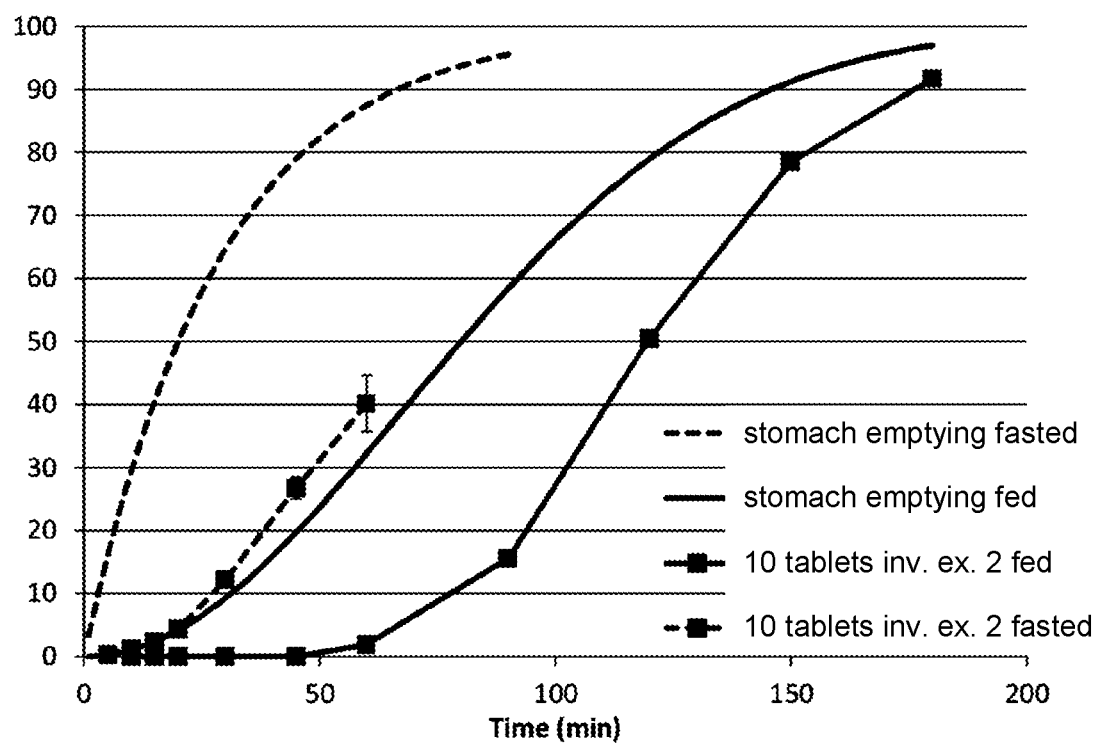
Figure 10C:
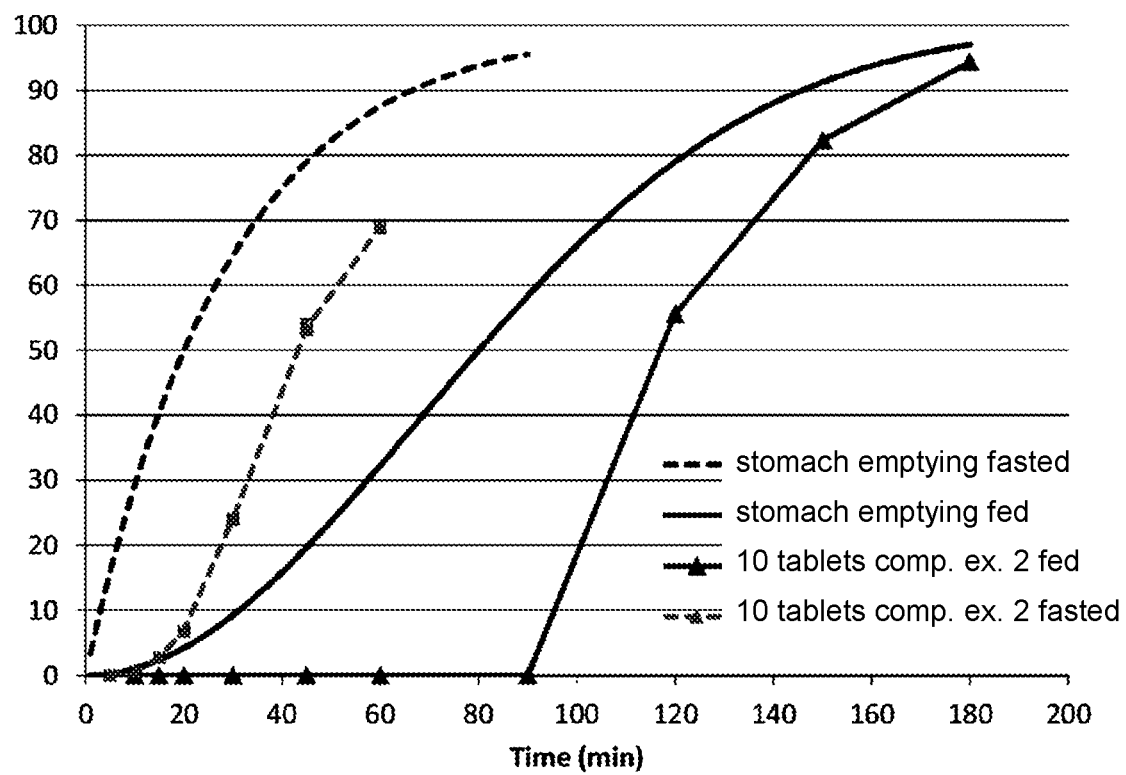

FIGS. 10A, 10B and 10C illustrate a comparison of fasted versus fed state experiments for hydrocodone according to Example 2.

Figure 11:
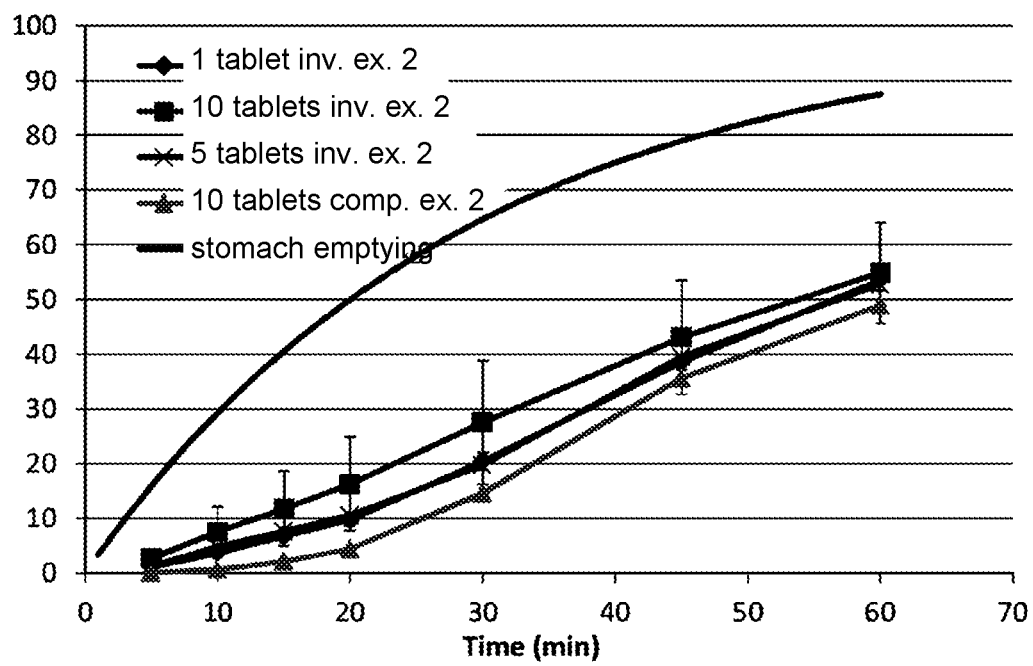

FIG. 11 illustrates a comparison of the fasted state experiments according to Example 2 for acetaminophen.

Figure 12:
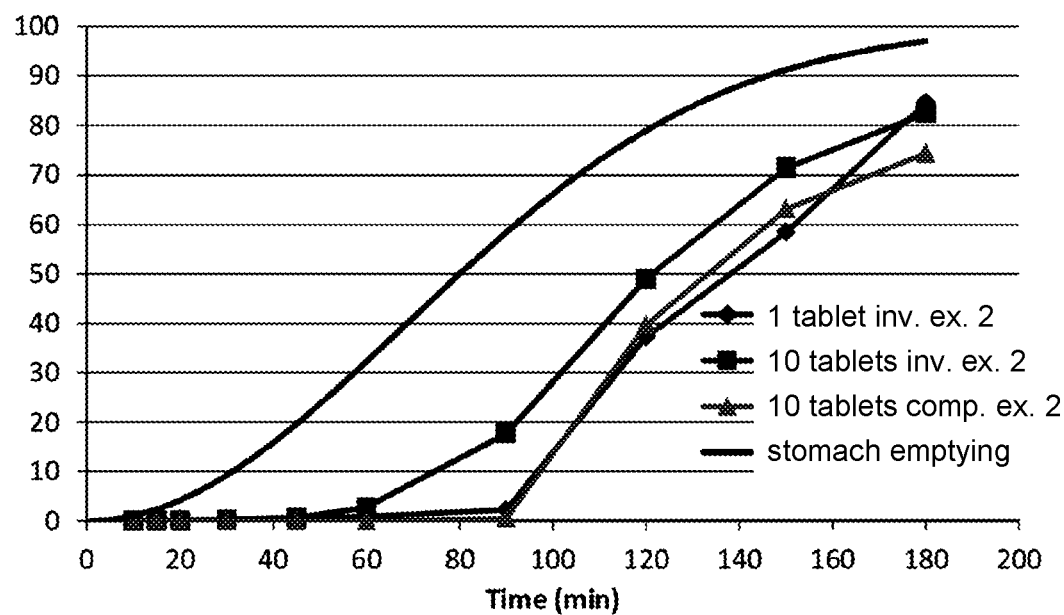

FIG. 12 illustrates a comparison of the fed state experiments according to Example 2 for acetaminophen.

Figure 13A:
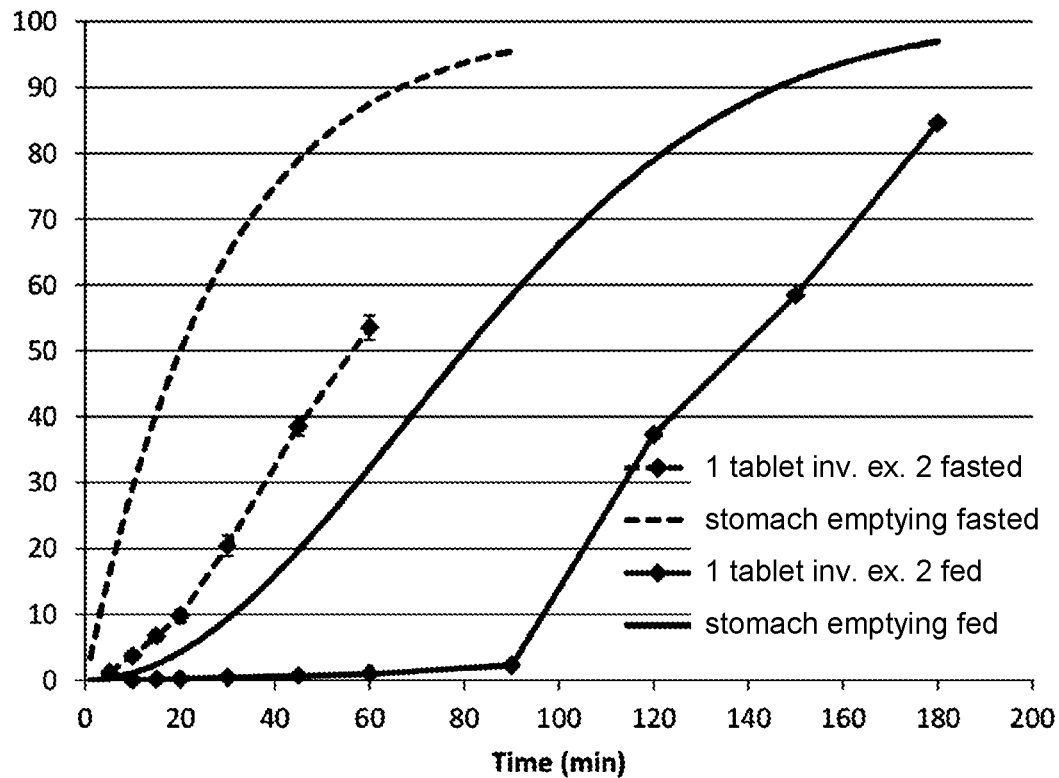
Figure 13B:
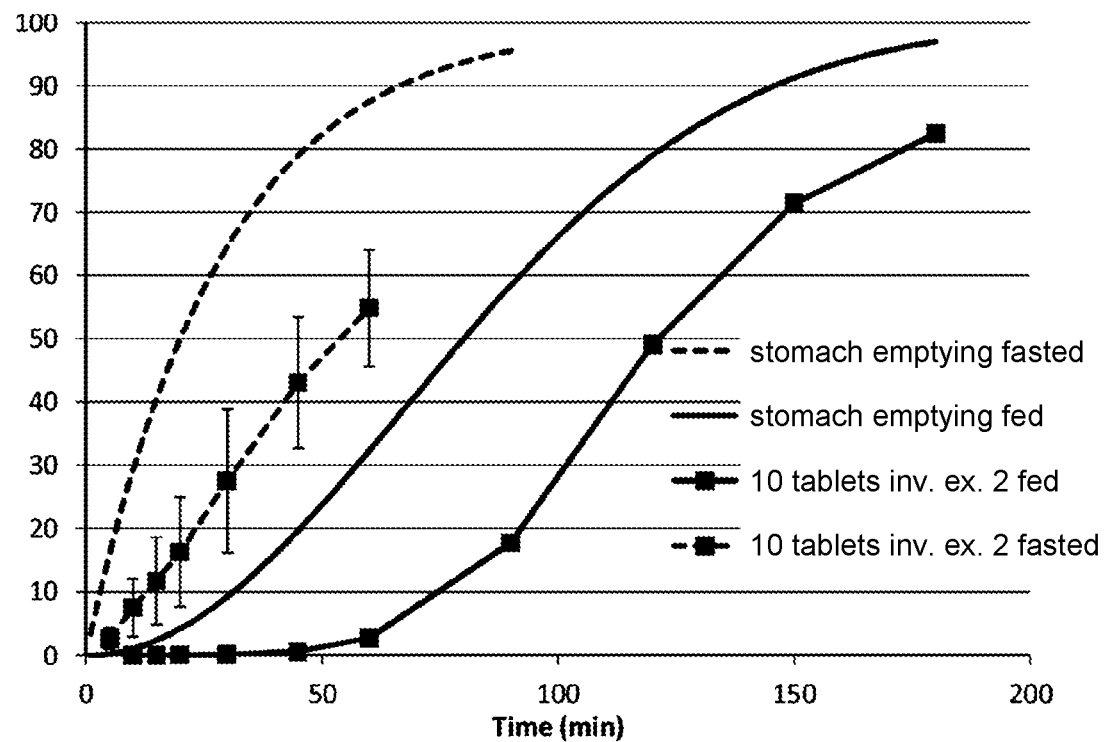
Figure 13C:
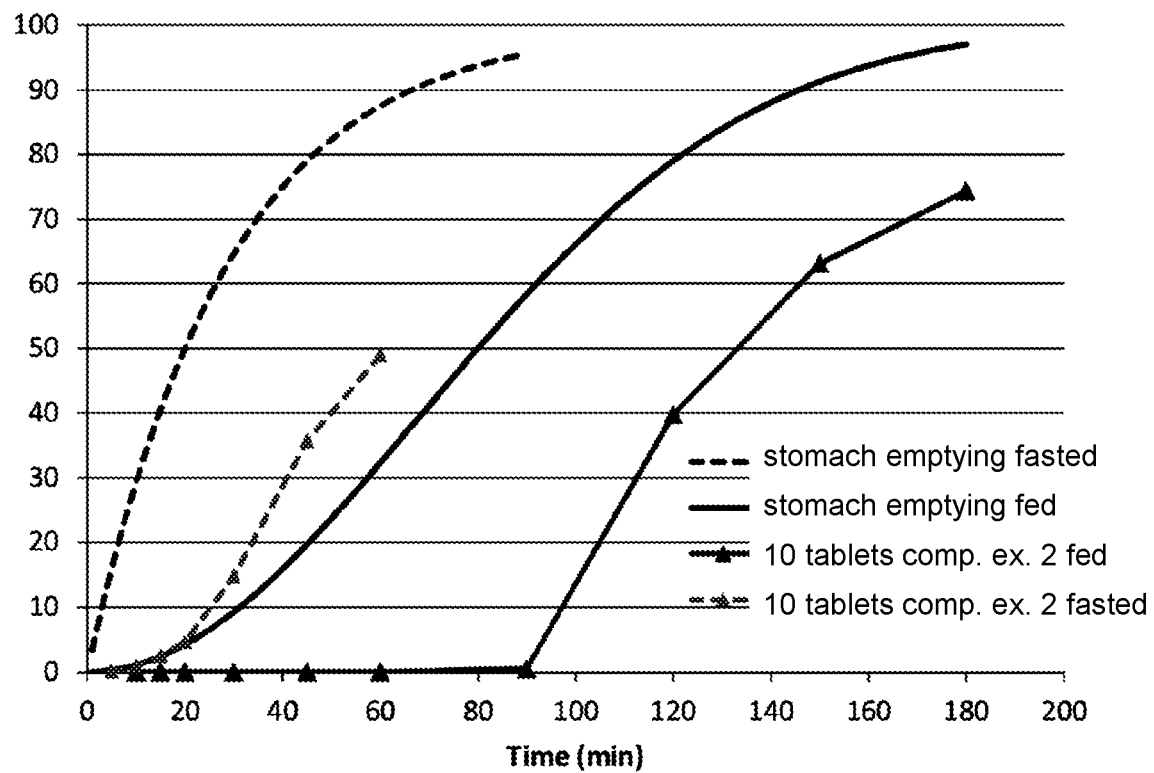

FIGS. 13A, 13B and 13C illustrate a comparison of fasted versus fed state experiments for acetaminophen according to Example 2.

Figure 14:
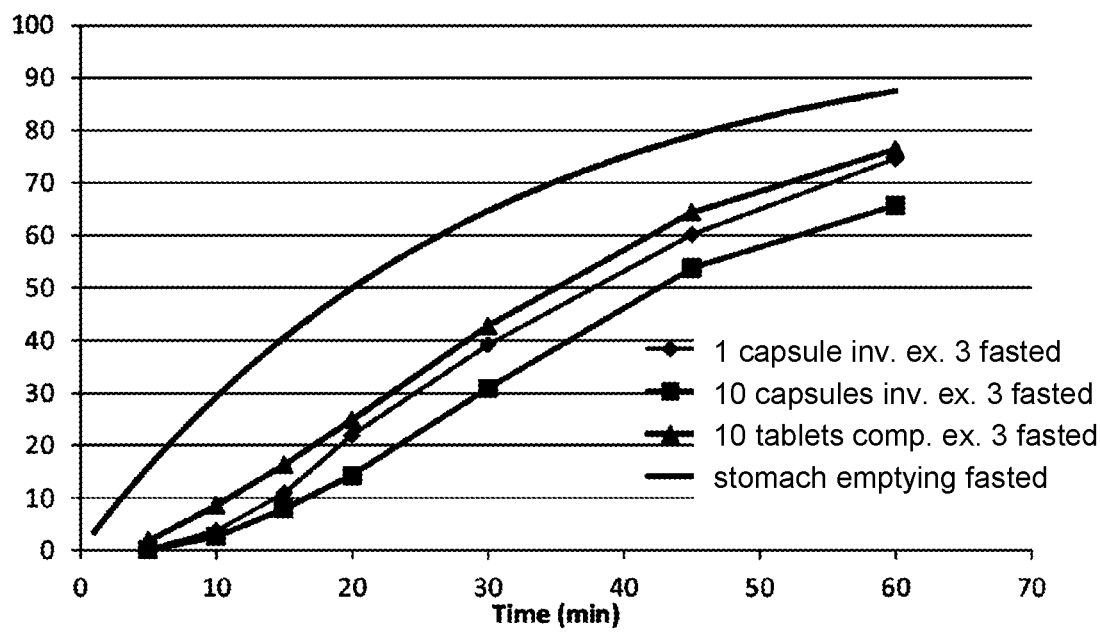

FIG. 14 illustrates a comparison of fasted state experiments for amphetamine (capsules and tablets) according to Example 3.

Figure 15:
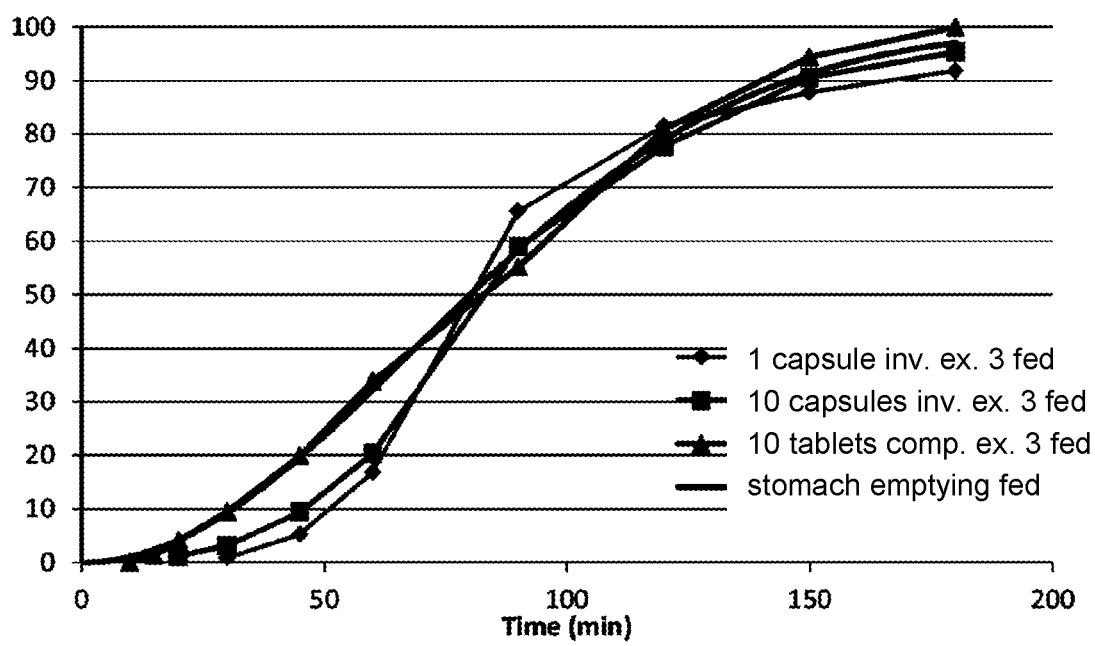

FIG. 15 illustrates a comparison of fed state experiments for amphetamine (capsules and tablets) according to Example 3.

Figure 16A:
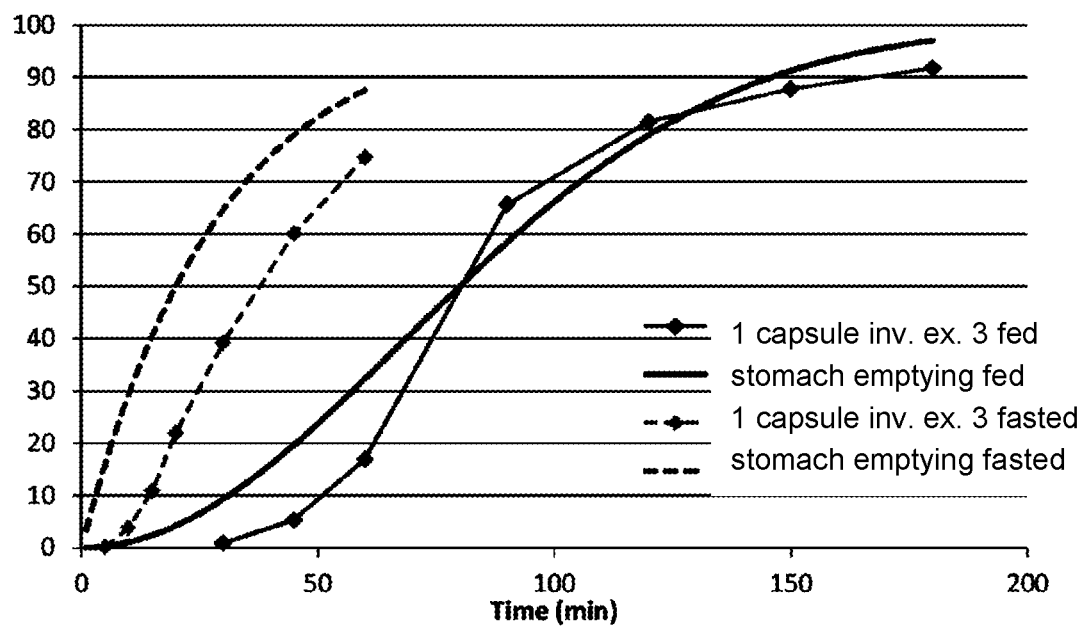
Figure 16B:
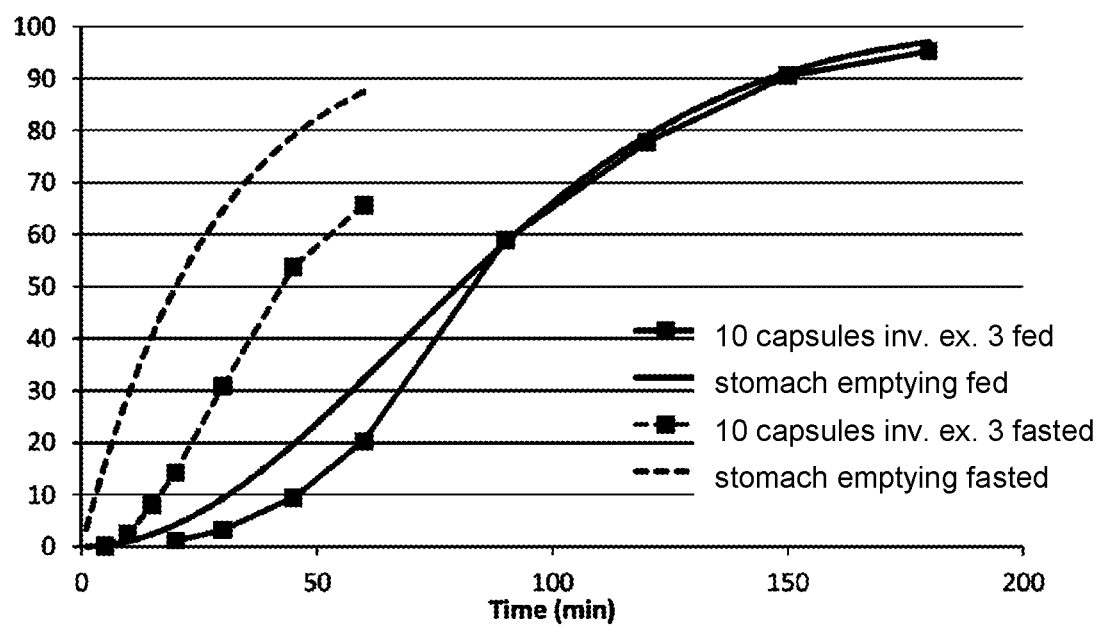
Figure 16C:
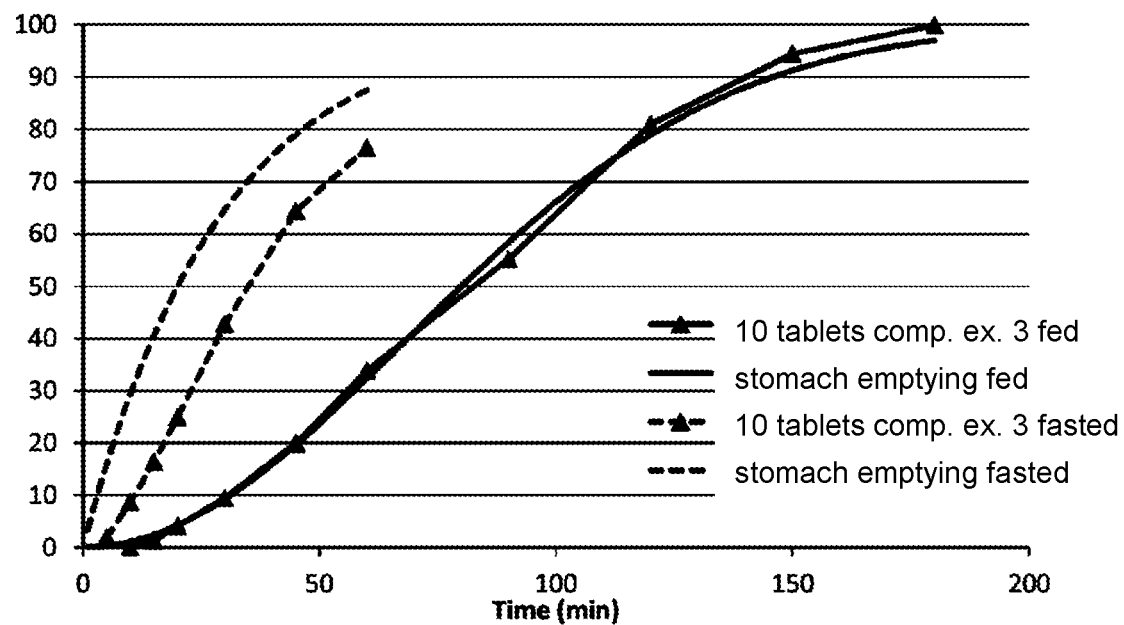

FIGS. 16A, 16B and 16C illustrate a comparison of fasted versus fed state experiments for amphetamine (capsules and tablets) according to Example 3.

Figure 17:
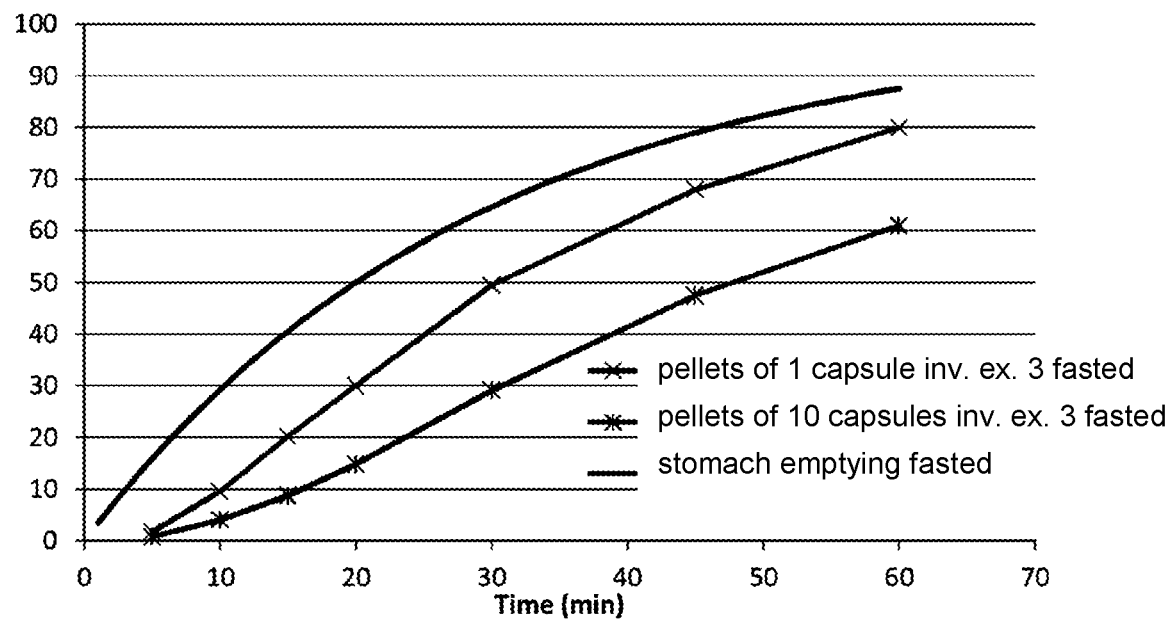

FIG. 17 illustrates a comparison of fasted state experiments for amphetamine (pellets) according to Example 3.

As used herein, the term "pharmaceutical dosage form" or "dosage form" refers to a pharmaceutical entity comprising a pharmacologically active ingredient a which is actually administered to, or taken by, a patient, preferably orally.

As used herein, expressions such as "tamper resistant", "abuse deterrent", "preventing", "avoiding", "deterring" or "inhibiting" associated with the abuse and overdose of drugs, relate to features of the dosage forms that provide significant physical and chemical impediments to these practices and processes. The objective in such deterrence includes both making abuse practices significantly more difficult to carry out, and making any product resulting from an attempt to carry out such abuse practices on the dosage forms significantly less desirable, less profitable, and less abusable to the potential abuser.

Preferably, the dosage form according to the invention is a capsule or a tablet.

In a preferred embodiment, when the dosage form is a capsule, it is preferably a sprinkle capsule or a multitude of sprinkle capsules. The capsule may comprise the particles and all excipients in form of a loose filling, i.e. an homogeneous mixture, or in form of layers (layered capsule filling).

In another preferred embodiment, when the dosage form is a tablet, the tablet may comprise the particle(s) A in an outer matrix material with homogeneous distribution or in form of a mantle tablet.

The dosage from comprises particle(s) of a first type, referred to as "particles(s) A" and optionally additional particle(s) of a second type, referred to as "particle(s) B". The particle(s) A, the optionally present particle(s) B, and/or the dosage form as such may be film-coated.

The dosage form according to the invention comprises one or more particles A and optionally, additionally one or more particles B. In the following, it is referred to "particles(s) A" and "particle(s) B" in order to express that the number of particles in each case may be independently one or more. When it is referred to "particle(s)", the respective embodiment independently applies to both, to particle(s) A and to optionally present particle(s) B.

The dosage form according to the invention may be compressed or molded in its manufacture, and it may be of almost any size, shape, weight, and color. Most dosage forms are intended to be swallowed as a whole and accordingly, preferred dosage forms according to the invention are designed for oral administration. However, alternatively dosage forms may be dissolved in the mouth, chewed, or dissolved or dispersed in liquid or meal before swallowing, and some may be placed in a body cavity. Thus, the dosage form according to the invention may alternatively be adapted for buccal, lingual, rectal or vaginal administration. Implants are also possible.

In a preferred embodiment, the dosage form according to the invention preferably can be regarded as a MUPS formulation (multiple unit pellet system). In a preferred embodiment, the dosage form according to the invention is monolithic. In another preferred embodiment, the dosage form according to the invention is not monolithic. In this regard, monolithic preferably means that the dosage form is formed or composed of material without joints or seams or consists of or constitutes a single unit.

In a preferred embodiment, the dosage form according to the invention contains all ingredients in a dense compact unit which in comparison to capsules has a comparatively high density. In another preferred embodiment, the dosage form according to the invention contains all ingredients in a capsule which in comparison to dense compact unit has a comparatively low density.

An advantage of the dosage forms according to the invention is that upon manufacture the particle(s) A may be mixed with excipients in different amounts to thereby produce dosage forms of different strengths. Another advantage of the dosage forms according to the invention is that upon manufacture the different particle(s) A, i.e. particles A having a different constitution, may be mixed with one another to thereby produce dosage forms of different properties, e.g. different release rates, different pharmacologically active ingredients a, and the like.

The dosage form according to the invention has preferably a total weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.3 g to 0.8 g.

In a preferred embodiment, the dosage form according to the invention is not film coated.

In another preferred embodiment, the dosage form according to the invention is provided, partially or completely, with a conventional coating. The dosage forms according to the invention are preferably film coated with conventional film coating compositions. Suitable coating materials are commercially available, e.g. under the trademarks Opadry®, Opaglos® and Eudragit®.

The coating can be resistant to gastric juices and dissolve as a function of the pH value of the release environment. By means of this coating, it is possible to ensure that the dosage form according to the invention passes through the stomach undissolved and the active compound is only released in the intestines. The coating which is resistant to gastric juices preferably dissolves at a pH value of between 5 and 7.5.

The subjects to which the dosage forms according to the invention can be administered are not particularly limited. Preferably, the subjects are animals, more preferably human beings.

The tamper-resistant dosage form according to the invention comprises particle(s) A which comprise the pharmacologically active ingredient a. Preferably, the particle(s) A contain the total amount of pharmacologically active ingredient a that is contained in the dosage form according to the invention, i.e. the dosage form according to the invention preferably does not contain pharmacologically active ingredient a outside particle(s) A.

The particle(s) A contain at least a pharmacologically active ingredient a and a polymer matrix that preferably comprises a polyalkylene oxide. Preferably, however, the particle(s) A contain additional pharmaceutical excipients such as disintegrants, antioxidants and plasticizers.

The pharmacologically active ingredient a is embedded, preferably dispersed in a polymer matrix preferably comprising a polyalkylene oxide. Preferably, the pharmacologically active ingredient a and the polyalkylene oxide are homogeneously distributed in the core of particle(s) A. Thus, the pharmacologically active ingredient a and the polyalkylene oxide are preferably homogeneously admixed with one another. Thus, the particle(s) A according to the invention are preferably not multilayered, but are preferably composed of a homogeneous core comprising the pharmacologically active ingredient a and the polyalkylene oxide, which homogenous core may optionally be coated with a film coating material that neither is pH sensitive nor contains the pharmacologically active ingredient a or the polyalkylene oxide.

The pharmacologically active ingredient a is not particularly limited.

In a preferred embodiment, the particle(s) A and the dosage form, respectively, contain only a single pharmacologically active ingredient a, optionally besides pharmacologically active ingredient b. In another preferred embodiment, the particle(s) A and the dosage form, respectively, contain a combination of two or more pharmacologically active ingredient a, optionally besides pharmacologically active ingredient b.

Preferably, pharmacologically active ingredient a is an active ingredient with potential for being abused. Active ingredients with potential for being abused are known to the person skilled in the art and comprise e.g. tranquilizers, stimulants, barbiturates, narcotics, opioids or opioid derivatives.

Preferably, the pharmacologically active ingredient a exhibits psychotropic action, i.e. has a psychotropic effect.

Preferably, the pharmacologically active ingredient a is selected from the group consisting of opiates, opioids, stimulants, tranquilizers, and other narcotics.

In a preferred embodiment, the pharmacologically active ingredient a is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

In another preferred embodiment, the pharmacologically active ingredient a is a stimulant. Stimulants are psychoactive drugs that induce temporary improvements in either mental or physical functions or both. Examples of these kinds of effects may include enhanced wakefulness, locomotion, and alertness. Preferred stimulants are phenylethylamine derivatives. According to the ATC index, stimulants are contained in different classes and groups, e.g. psychoanaleptics, especially psychostimulants, agents used for ADHD and nootropics, particularly centrally acting sympathomimetics; and e.g. nasal preparations, especially nasal decongestants for systemic use, particularly sympathomimetics.

The following opiates, opioids, stimulants, tranquilizers or other narcotics are substances with a psychotropic action, i.e. have a potential of abuse, and hence are preferably contained in the dosage form and the particle(s) A, respectively: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, cebranopadol, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dex-amphetamine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, methamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxyco done, oxymorphone, *Papaver somniferum*, papaveretum, pemoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, pseudoephedrine, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclo-hexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethyl amino-3(3-methoxyphenyl)-2-methyl-pentan-3-ol, (1RS,3RS,6RS)-6-dimethyl amino methyl-1-(3-methoxyphenyl)-cyclohexane-1,3-diol, preferably as racemate, 3-(2-dimethyl amino methyl-1-hydroxy-cyclohexyl)phenyl 2-(4-isobutyl-phenyl)propionate, 3-(2-dimethyl amino methyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)

propionate, (RR-SS)-2-acetoxy-4-trifluoromethyl-benzoic acid 3-(2-dimethyl amino methyl-1-hydroxy-cyclohexyl)-phenyl ester, (RR-SS)-2-hydroxy-4-trifluoromethyl-benzoic acid 3-(2-dimethyl amino methyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethyl aminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment, the pharmacologically active ingredient a is selected from the group consisting of DPI-125, M6G (CE-04-410), ADL-5859, CR-665, NRP290 and sebacoyl dinalbuphine ester.

In a preferred embodiment, the pharmacologically active ingredient a is an opioid selected from the group consisting of oxycodone, hydrocodone, oxymorphone, hydromorphone, morphine, tramadol, tapentadol, cebranopadol and the physiologically acceptable salts thereof.

In another preferred embodiment, the pharmacologically active ingredient a is a stimulant selected from the group consisting of amphetamine, dex-amphetamine, dex-methylphenidate, atomoxetine, caffeine, ephedrine, phenylpropanolamine, phenylephrine, fencamphamin, fenozolone, fenetylline, methylenedioxymethamphetamine (MDMA), methylenedioxypyrovalerone (MDPV), prolintane, lisdexamfetamine, mephedrone, methamphetamine, methylphenidate, modafinil, nicotine, pemoline, phenylpropanolamine, propylhexedrine, dimethylamylamine, and pseudoephedrine.

The pharmacologically active ingredient a may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

The pharmacologically active ingredient a is present in the dosage form in a therapeutically effective amount. The amount that constitutes a therapeutically effective amount varies according to the active ingredients being used, the condition being treated, the severity of said condition, the patient being treated, and the frequency of administration.

The content of the pharmacologically active ingredient a in the dosage form is not limited. The dose of the pharmacologically active ingredient a which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient a that is contained in the dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

The skilled person may readily determine an appropriate amount of pharmacologically active ingredient a to include in a dosage form. For instance, in the case of analgesics, the total amount of pharmacologically active ingredient a present in the dosage form is that sufficient to provide analgesia. The total amount of pharmacologically active ingredient a administered to a patient in a dose will vary depending on numerous factors including the nature of the pharmacologically active ingredient a, the weight of the patient, the severity of the pain, the nature of other therapeutic agents being administered etc.

In a particularly preferred embodiment, the pharmacologically active ingredient a is tapentadol, preferably its HCl salt, and the dosage form is adapted for administration once daily, twice daily, thrice daily or more frequently. In this embodiment, pharmacologically active ingredient a is preferably contained in the dosage form in an amount of from 25 to 100 mg.

In a particularly preferred embodiment, the pharmacologically active ingredient a is oxymorphone, preferably its HCl salt, and the dosage form is adapted for administration once daily, twice daily, thrice daily or more frequently. In this embodiment, the pharmacologically active ingredient a is preferably contained in the dosage form in an amount of from 5 to 40 mg. In another particularly preferred embodiment, the pharmacologically active ingredient a is oxymorphone, preferably its HCl salt, and the dosage form is adapted for administration once daily. In this embodiment, the pharmacologically active ingredient a is preferably contained in the dosage form in an amount of from 10 to 80 mg.

In another particularly preferred embodiment, the pharmacologically active ingredient a is oxycodone, preferably its HCl salt, and the dosage form is adapted for administration once daily, twice daily, thrice daily or more frequently. In this embodiment, the pharmacologically active ingredient a is preferably contained in the dosage form in an amount of from 5 to 80 mg. Oxycodone, preferably its HCl salt, is preferably combined with acetaminophen as optionally present pharmacologically active ingredient b.

In still another particularly preferred embodiment, the pharmacologically active ingredient a is hydromorphone, preferably its HCl, and the dosage form is adapted for administration once daily, twice daily, thrice daily or more frequently. In this embodiment, the pharmacologically active ingredient a is preferably contained in the dosage form in an amount of from 2 to 52 mg. In another particularly preferred embodiment, the pharmacologically active ingredient a is hydromorphone, preferably its HCl, and the dosage form is adapted for administration once daily, twice daily, thrice daily or more frequently. In this embodiment, the pharmacologically active ingredient a is preferably contained in the dosage form in an amount of from 4 to 104 mg.

In yet another particularly preferred embodiment, the pharmacologically active ingredient a is hydrocodone, preferably its bitartrate salt, and the dosage form is adapted for administration once daily, twice daily, thrice daily or more frequently. In this embodiment, the pharmacologically active ingredient a is preferably contained in the dosage form in an amount of from 2.5 to 10 mg. Hydrocodone, preferably its bitartrate salt, is preferably combined with acetaminophen as optionally present pharmacologically active ingredient b.

Preferably, the content of the pharmacologically active ingredient a is at least 0.5 wt.-%, based on the total weight of the dosage form and/or based on the total weight of the particle(s) A.

Preferably, the content of the pharmacologically active ingredient a is at least 2.5 wt.-%, more preferably at least 3.0 wt.-%, still more preferably at least 3.5 wt.-%, yet more preferably at least 4.0 wt.-%, most preferably at least 4.5 wt.-%, based on the total weight of the dosage form and/or based on the total weight of the particle(s) A.

In a preferred embodiment, the content of the pharmacologically active ingredient a is at most 70 wt.-%, more preferably at most 65 wt.-%, still more preferably at most 60 wt.-%, yet more preferably at most 55 wt.-%, most preferably at most 50 wt.-%, based on the total weight of the dosage form and/or based on the total weight of the particle(s) A.

In another preferred embodiment, the content of the pharmacologically active ingredient a is at most 20 wt.-%, more preferably at most 17.5 wt.-%, still more preferably at most 15 wt.-%, yet more preferably at most 12.5 wt.-%, most preferably at most 10 wt.-%, based on the total weight of the dosage form and/or based on the total weight of the particle(s) A.

Preferably, the content of the pharmacologically active ingredient a is within the range of from 0.01 to 80 wt.-%, more preferably 0.1 to 50 wt.-%, still more preferably 1 to 25 wt.-%, based on the total weight of the dosage form and/or based on the total weight of the particle(s) A.

The particle(s) A present in the dosage forms according to the invention preferably comprise 1 to 75 wt.-% of pharmacologically active ingredient a, more preferably 2 to 70 wt.-% of pharmacologically active ingredient a, still more preferably 3 to 65 wt.-% of pharmacologically active ingredient a, based on the total weight of the dosage form and/or based on the total weight of the particle(s) A.

A skilled person knows how to determine pharmacokinetic parameters such as $t_{1/2}$, $T_{max}$, $C_{max}$, AUC and bioavailability. For the purposes of the description, the pharmacokinetic parameters, which may be determined from the blood plasma concentrations of 3-(2-dimethylaminomethylcyclohexyl)phenol, are defined as follows:

$C_{max}$    maximum measured plasma concentration of the active ingredient after single administration (=average peak plasma level)
$t_{max}$    interval of time from administration of the active ingredient until $C_{max}$ is reached
AUC    total area of the plasma concentration/time curve including the subarea from the final measured value extrapolated to infinity
$t_{1/2}$    half-life The above parameters are in each case stated as mean values of the individual values for all investigated patients/test subjects.

A person skilled in the art knows how the pharmacokinetic parameters of the active ingredient may be calculated from the measured concentrations of the active ingredient in the blood plasma. In this connection, reference may be made, for example, to Willi Cawello (ed.) *Parameters for Compartment-free Pharmacokinetics*, Shaker Verlag Aachen (1999).

In a preferred embodiment, the pharmacologically active ingredient a is tapentadol or a physiologically acceptable salt thereof, e.g. the hydrochloride. Preferably, the dosage form according to the invention provides a mean absolute bioavailability of tapentadol of at least 22%, more preferably at least 24%, still more preferably at least 26%, yet more preferably at least 28%, most preferably at least 30%, and in particular at least 32%. $T_{max}$ of tapentadol is preferably within the range of 1.25±1.20 h, more preferably 1.25±1.00 h, still more preferably 1.25±0.80 h, yet more preferably 1.25±0.60 h, most preferably 1.25±0.40 h, and in particular 1.25±0.20 h. $t_{1/2}$ of tapentadol is preferably within the range of 4.0±2.8 h, more preferably 4.0±2.4 h, still more preferably 4.0±2.0 h, yet more preferably 4.0±1.6 h, most preferably 4.0±1.2 h, and in particular 4.0±0.8 h. Preferably, when normalized to a dose of 100 mg tapentadol, $C_{max}$ of tapentadol is preferably within the range of 90±85 ng/mL, more preferably 90±75 ng/mL, still more preferably 90±65 ng/mL, yet more preferably 90±55 ng/mL, most preferably 90±45 ng/mL, and in particular 90±35 ng/mL; and/or AUC of tapentadol is preferably within the range of 420±400 ng/mL·h, more preferably 420±350 ng/mL·h, still more preferably 420±300 ng/mL·h, yet more preferably 420±250 ng/mL·h, most preferably 420±200 ng/mL·h, and in particular 420±150 ng/mL·h.

In another preferred embodiment, the pharmacologically active ingredient a is oxycodone or a physiologically acceptable salt thereof, e.g. the hydrochloride. Preferably, the dosage form according to the invention provides a mean absolute bioavailability of oxycodone of at least 40%, more preferably at least 45%, still more preferably at least 50%, yet more preferably at least 55%, most preferably at least 60%, and in particular at least 70%. $T_{max}$ of oxycodone is preferably within the range of 2.6±2.5 h, more preferably 2.6±2.0 h, still more preferably 2.6±1.8 h, yet more preferably 2.6±0.1.6 h, most preferably 2.6±1.4 h, and in particular 2.6±1.2 h. $t_{1/2}$ of oxycodone is preferably within the range of 3.8±3.5 h, more preferably 3.8±3.0 h, still more preferably 3.8±2.5 h, yet more preferably 3.8±2.0 h, most preferably 3.8±1.5 h, and in particular 3.8±1.0 h. Preferably, when normalized to a dose of 30 mg oxycodone, $C_{max}$ of oxycodone is preferably within the range of 40±35 ng/mL, more preferably 40±30 ng/mL, still more preferably 40±25 ng/mL, yet more preferably 40±20 ng/mL, most preferably 40±15 ng/mL, and in particular 40±10 ng/mL; and/or AUC of oxycodone is preferably within the range of 270±250 ng/mL·h, more preferably 270±200 ng/mL·h, still more preferably 270±150 ng/mL·h, yet more preferably 270±100 ng/mL·h, most preferably 270±75 ng/mL·h, and in particular 270±50 ng/mL·h.

In still another preferred embodiment, the pharmacologically active ingredient a is hydrocodone or a physiologically acceptable salt thereof, e.g. the bitartrate. $T_{max}$ of hydrocodone is preferably within the range of 1.3±1.2 h, more preferably 1.3±1.0 h, still more preferably 1.3±0.8 h, yet more preferably 1.3±0.6 h, most preferably 1.3±0.4 h, and in particular 1.3±0.2 h. $t_{1/2}$ of hydrocodone is preferably within the range of 3.8±3.5 h, more preferably 3.8±3.0 h, still more preferably 3.8±2.5 h, yet more preferably 3.8±2.0 h, most preferably 3.8±1.5 h, and in particular 3.8±1.0 h.

In yet another preferred embodiment, the pharmacologically active ingredient a is morphine or a physiologically acceptable salt thereof, e.g. the sulfate. Preferably, the dosage form according to the invention provides a mean absolute bioavailability of morphine of at least 15%, more preferably at least 20%, still more preferably at least 25%, yet more preferably at least 30%, most preferably at least 35%, and in particular at least 40%. $T_{max}$ of morphine is preferably within the range of 0.625±0.60 h, more preferably 0.625±0.50 h, still more preferably 0.625±0.40 h, yet more preferably 0.625±0.30 h, most preferably 0.625±0.20 h, and in particular 0.625±0.15 h. Preferably, when normalized to a dose of 30 mg morphine sulfate, $C_{max}$ of morphine is preferably within the range of 25±20 ng/mL, more preferably 25±15 ng/mL, still more preferably 25±10 ng/mL, yet more preferably 25±5 ng/mL; and/or AUC of morphine is preferably within the range of 50±45 ng/mL·h, more preferably 50±40 ng/mL·h, still more preferably 50±35 ng/mL·h, yet more preferably 50±30 ng/mL·h, most preferably 50±25 ng/mL·h, and in particular 50±20 ng/mL·h.

In still another preferred embodiment, the pharmacologically active ingredient a is amphetamine or a physiologically acceptable salt thereof. $T_{max}$ of amphetamine is preferably within the range of 1.7±1.2 h, more preferably 1.7±1.0 h, still more preferably 1.7±0.8 h, yet more preferably 1.7±0.6 h, most preferably 1.7±0.4 h, and in particular 1.7±0.2 h.

In still another preferred embodiment, the pharmacologically active ingredient a is dex-amphetamine or a physiologically acceptable salt thereof, e.g. the sulfate. $T_{max}$ of dex-amphetamine is preferably within the range of 3.0±2.9 h, more preferably 3.0±2.5 h, still more preferably 3.0±2.1 h, yet more preferably 3.0±1.7 h, most preferably 3.0±1.3 h, and in particular 3.0±0.9 h. $t_{1/2}$ of dex-amphetamine is preferably within the range of 10±6.0 h, more preferably 10±5.0 h, still more preferably 10±4.0 h, yet more preferably 10±3.0 h, most preferably 10±2.0 h, and in particular 10±1.0 h.

In a preferred embodiment, the pharmaceutical dosage form additionally contains a second pharmacologically active ingredient (pharmacologically active ingredient b).

The optionally present pharmacologically active ingredient b is not particularly limited. The optionally present pharmacologically active ingredient b differs from the pharmacologically active ingredient a.

In a preferred embodiment, the optionally present pharmacologically active ingredient b exhibits no psychotropic action.

In another preferred embodiment, the optionally present pharmacologically active ingredient b is selected from ATC classes [M01A], [M01C], [N02B] and [N02C] according to the WHO.

In a particularly preferred embodiment,
(i) the pharmacologically active ingredient a has a psychotropic effect; and/or
(ii) the optionally present pharmacologically active ingredient b is selected from ATC classes [M01A], [M01C], [N02B] and [N02C] according to the WHO.

Preferably, the optionally present pharmacologically active ingredient b is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, acetaminophen (paracetamol), phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine, bucillamine, their physiologically acceptable salts, as well as mixtures thereof.

In a preferred embodiment, the optionally present pharmacologically active ingredient b is acetaminophen or ibuprofen, more preferably acetaminophen.

In a particularly preferred embodiment, the pharmacologically active ingredient a is hydrocodone or a physiologically acceptable salt thereof and the optionally present pharmacologically active ingredient b is acetaminophen.

The optionally present pharmacologically active ingredient b is present in the dosage form in a therapeutically effective amount. In general, the amount that constitutes a therapeutically effective amount varies according to the pharmacologically active ingredients being used, the condition being treated, the severity of said condition, the patient being treated, and whether the dosage form or the segment in which the pharmacologically active ingredient is contained is designed for an immediate or retarded release.

The total amount of the optionally present pharmacologically active ingredient b in the dosage form is not limited. The total amount of the optionally present pharmacologically active ingredient b which is adapted for administration preferably is in the range of 0.1 mg to 2,000 mg or 0.1 mg to 1,000 mg or 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the optionally present pharmacologically active ingredient b which is contained in the dosage form is within the range of from 10 to 1,000 mg, more preferably 50 to 900 mg, still more preferably 100 to 800 mg, yet more preferably 200 to 600 mg, most preferably 250 to 500 mg and in particular 300 to 400 mg. In another preferred embodiment, the total amount of the optionally present pharmacologically active ingredient b which is contained in the dosage form is within the range of from 10 to 500 mg, more preferably 12 to 450 mg, still more preferably 14 to 400 mg, yet more preferably 16 to 375 mg, most preferably 18 to 350 mg and in particular 20 to 325 mg.

The total content of the optionally present pharmacologically active ingredient b preferably ranges from about 0.01 wt.-% to about 95 wt.-%, more preferably from about 0.1 wt.-% to about 80 wt.-%, even more preferably from about 1.0 wt.-% to about 50 wt.-%, yet more preferably from about 1.5 wt.-% to about 30 wt.-%, and most preferably from about 2.0 wt.-% to 20 wt.-%, based on the total weight of the dosage form.

Preferably, the total content of the optionally present pharmacologically active ingredient b is within the range of from 0.01 to 80 wt.-%, more preferably 0.1 to 50 wt.-%, still more preferably 1 to 25 wt.-%, based on the total weight of the dosage form.

In a particularly preferred embodiment, the optionally present pharmacologically active ingredient b is acetaminophen. In this embodiment, the acetaminophen is preferably contained in the particle(s) B or the dosage form in an amount of from 100 to 600 mg, more preferably 150 to 550 mg, still more preferably 200 to 500 mg, most preferably 250 to 450 mg and in particular 275 to 400 mg.

In another particularly preferred embodiment, the optionally present pharmacologically active ingredient b is ibuprofen. In this embodiment, the ibuprofen is preferably contained in the particle(s) B or the dosage form in an amount of from 100 to 600 mg, more preferably 150 to 550 mg, still more preferably 200 to 500 mg, most preferably 250 to 450 mg and in particular 275 to 400 mg.

Preferred combinations $A^1$ to $A^{36}$ of the pharmacologically active ingredient a and the optionally present pharmacologically active ingredient b are summarized in the table here below, wherein the pharmacologically active ingredient a as well as the optionally present pharmacologically active ingredient b each also refer to the physiologically acceptable salts thereof, particularly to the hydrochlorides or bitartrates:

|  | a | b |
|---|---|---|
| $A^1$ | oxycodone | ibuprofen |
| $A^2$ | oxymorphone | ibuprofen |
| $A^3$ | hydrocodone | ibuprofen |
| $A^4$ | hydromorphone | ibuprofen |
| $A^5$ | morphine | ibuprofen |
| $A^6$ | tapentadol | ibuprofen |
| $A^7$ | tramadol | ibuprofen |
| $A^8$ | buprenorphine | ibuprofen |
| $A^9$ | pseudoephedrine | ibuprofen |
| $A^{10}$ | oxycodone | acetaminophen |
| $A^{11}$ | oxymorphone | acetaminophen |
| $A^{12}$ | hydrocodone | acetaminophen |
| $A^{13}$ | hydromorphone | acetaminophen |
| $A^{14}$ | morphine | acetaminophen |
| $A^{15}$ | tapentadol | acetaminophen |
| $A^{16}$ | tramadol | acetaminophen |
| $A^{17}$ | buprenorphine | acetaminophen |
| $A^{18}$ | pseudoephedrine | acetaminophen |
| $A^{19}$ | oxycodone | diclofenac |
| $A^{20}$ | oxymorphone | diclofenac |
| $A^{21}$ | hydrocodone | diclofenac |
| $A^{22}$ | hydromorphone | diclofenac |
| $A^{23}$ | morphine | diclofenac |
| $A^{24}$ | tapentadol | diclofenac |
| $A^{25}$ | tramadol | diclofenac |
| $A^{26}$ | buprenorphine | diclofenac |
| $A^{27}$ | pseudoephedrine | diclofenac |
| $A^{28}$ | oxycodone | acetylsalicylic acid |
| $A^{29}$ | oxymorphone | acetylsalicylic acid |
| $A^{30}$ | hydrocodone | acetylsalicylic acid |
| $A^{31}$ | hydromorphone | acetylsalicylic acid |
| $A^{32}$ | morphine | acetylsalicylic acid |
| $A^{33}$ | tapentadol | acetylsalicylic acid |
| $A^{34}$ | tramadol | acetylsalicylic acid |
| $A^{35}$ | buprenorphine | acetylsalicylic acid |
| $A^{36}$ | pseudoephedrine | acetylsalicylic acid |

In a preferred embodiment, the relative weight ratio of the total content of the pharmacologically active ingredient a to the total content of the optionally present pharmacologically active ingredient b [a:b] is within the range of (8±1):1, more preferably (7±1):1, still more preferably (6±1):1, yet more preferably (5±1):1, even more preferably (4±1):1, most preferably (3±1):1 and in particular (2±1):1.

In still another preferred embodiment, the relative weight ratio of the total content of the optionally present pharmacologically active ingredient b to the total content of the pharmacologically active ingredient a [b:a] is within the range of (8±1):1, more preferably (7±1):1, still more preferably (6±1):1, yet more preferably (5±1):1, even more preferably (4±1):1, most preferably (3±1):1 and in particular (2±1):1. Preferably, the relative weight ratio of the total content of the optionally present pharmacologically active ingredient b to the total content of the pharmacologically active ingredient a [b:a] is within the range of from 10:1 to 150:1, more preferably 10:1 to 50:1, or 30:1 to 140:1.

The dosage form according to the invention preferably provides fast release, more preferably immediate release under in vitro conditions of the pharmacologically active ingredient a, and independently of the optionally present pharmacologically active ingredient b in accordance with Ph. Eur.

The term "immediate release" as applied to dosage forms is understood by persons skilled in the art which has structural implications for the respective dosage forms. The term is defined, for example, in the current issue of the US Pharmacopoeia (USP), General Chapter 1092, "THE DISSOLUTION PROCEDURE: DEVELOPMENT AND VALIDATION", heading "STUDY DESIGN", "Time Points". For immediate-release dosage forms, the duration of the procedure is typically 30 to 60 minutes; in most cases, a single time point specification is adequate for Pharmacopeia purposes. Industrial and regulatory concepts of product comparability and performance may require additional time points, which may also be required for product registration or approval. A sufficient number of time points should be selected to adequately characterize the ascending and plateau phases of the dissolution curve. According to the Biopharmaceutics Classification System referred to in several FDA Guidances, highly soluble, highly permeable drugs formulated with rapidly dissolving products need not be subjected to a profile comparison if they can be shown to release 85% or more of the active drug substance within 15 minutes. For these types of products a one-point test will suffice. However, most products do not fall into this category. Dissolution profiles of immediate-release products typically show a gradual increase reaching 85% to 100% at 30 to 45 minutes. Thus, dissolution time points in the range of 15, 20, 30, 45, and 60 minutes are usual for most immediate-release products.

Preferably, the dosage form according to the invention provides an in vitro release profile of the pharmacologically active ingredient a such that after 30 min under in vitro conditions at 37° C. in 900 mL 0.1 M HCl at 25 rpm in accordance with Ph. Eur.

(i) a single dosage form has released at least 30 wt.-%, or at least 31 wt.-%, or at least 32 wt.-%, or at least 33 wt.-%, or at least 34 wt.-%, or at least 35 wt.-%, or at least 36 wt.-%, or at least 37 wt.-%, or at least 38 wt.-%, or at least 39 wt.-%, or at least 40 wt.-%, of the pharmacologically active ingredient a originally contained in the dosage form; and/or (ii) a multitude of ten dosage forms has released not more than 25 wt.-%, or not more than 24 wt.-%, or not more than 23 wt.-%, or not more than 22 wt.-%, or not more than 21 wt.-%, or not more than 20 wt.-%, or not more than 19 wt.-%, or not more than 18 wt.-%, or not more than 17 wt.-%, or not more than 16 wt.-%, or not more than 15 wt.-%, of the overall content of the pharmacologically active ingredient a originally contained in the multitude of ten dosage forms.

Preferably, the dosage form according to the invention provides an in vitro release profile of the pharmacologically active ingredient a such that after 30 min under in vitro conditions at 37° C. in 900 mL 0.1 M HCl at 25 rpm in accordance with Ph. Eur.

(i) a single dosage form has released X mg of the pharmacologically active ingredient a originally contained in the dosage form; and (ii) a multitude of n dosage forms has released Y mg of the pharmacologically active ingredient a originally contained in the a multitude of n dosage forms;
wherein Y/n is not more than 50% of X, preferably not more than 45% of X, still more preferably not more than 40% of X, yet more preferably not more than 35% of X, most preferably not more than 30% of X; and wherein n is an integer of from 2 to 10, preferably 5 or 10, more preferably 10.

For example, when a single dosage form has released after 30 minutes 4.65 mg of pharmacologically active ingredient a, X is 4.65. Under these circumstances, a multitude of 10 dosage forms (n=10) must not release more than a total of 23.25 mg of the pharmacologically active ingredient a.

Preferably, when the dosage form according to the invention comprises the optionally present pharmacologically active ingredient b, the dosage form provides an in vitro release profile of the pharmacologically active ingredient b such that after 30 min under in vitro conditions at 37° C. in 900 mL 0.1 M HCl at 25 rpm in accordance with Ph. Eur.
(i) a single dosage form has released V mg of the pharmacologically active ingredient b originally contained in the dosage form; and
(ii) a multitude of n dosage forms has released W mg of the pharmacologically active ingredient b originally contained in the a multitude of n dosage forms;
wherein W/n is not more than 50% of V, preferably not more than 45% of V, still more preferably not more than 40% of V, yet more preferably not more than 35% of V, most preferably not more than 30% of V; and wherein n is an integer of from 2 to 10, preferably 5 or 10, more preferably 10.

Suitable in vitro conditions are known to the skilled artisan. In this regard it can be referred to, e.g., the Eur. Ph. Preferably, the release profile is measured under the following conditions: Paddle apparatus equipped without sinker, 25 rpm, 37±5° C., 900 mL 0.1 N HCl.

Further preferred release profiles $B^1$ to $B^{10}$ that independently apply to the release of pharmacologically active ingredient a and optionally present pharmacologically active ingredient b are summarized in the table here below [all data in wt.-% of released pharmacologically active ingredient a/b]:

| time | $B^1$ | $B^2$ | $B^3$ | $B^4$ | $B^5$ | $B^6$ | $B^7$ | $B^8$ | $B^9$ | $B^{10}$ |
|---|---|---|---|---|---|---|---|---|---|---|
| 10 min | ≥30 | ≥35 | ≥40 | ≥45 | ≥50 | ≥60 | ≥70 | ≥80 | ≥80 | ≥80 |
| 20 min | ≥50 | ≥55 | ≥60 | ≥65 | ≥70 | ≥75 | ≥80 | ≥85 | ≥90 | ≥95 |
| 30 min | ≥55 | ≥60 | ≥65 | ≥70 | ≥75 | ≥85 | ≥90 | ≥95 | ≥95 | ≥95 |
| 40 min | ≥60 | ≥65 | ≥70 | ≥80 | ≥85 | ≥90 | ≥95 | ≥95 | ≥95 | ≥95 |
| 50 min | ≥65 | ≥70 | ≥80 | ≥85 | ≥88 | ≥92 | ≥95 | ≥95 | ≥95 | ≥95 |
| 60 min | ≥75 | ≥80 | ≥85 | ≥90 | ≥92 | ≥94 | ≥95 | ≥95 | ≥95 | ≥95 |

In a preferred embodiment, the dosage form according to the invention is adapted for administration once daily. In another preferred embodiment, the dosage form according to the invention is adapted for administration twice daily. In still another preferred embodiment, the dosage form according to the invention is adapted for administration thrice daily. In yet another preferred embodiment, the dosage form according to the invention is adapted for administration more frequently than thrice daily, for example 4 times daily, 5 times daily, 6 times daily, 7 times daily or 8 times daily.

Preferably, the dosage form according to the invention has under in vitro conditions a disintegration time measured in accordance with Ph. Eur. of at most 10 minutes, more preferably at most 8 minutes, or at most 6 minutes, or at most 5 minutes, more preferably at most 4 minutes, still more preferably at most 3 minutes, yet more preferably at most 2.5 minutes, most preferably at most 2 minutes and in particular at most 1.5 minutes.

The dosage form according to the invention comprises one or more particle(s) A, typically a multitude of particles A. The particle(s) A comprise a pharmacologically active ingredient a, which is embedded in a polymer matrix that preferably comprises a polyalkylene oxide and preferably further excipients.

For the purpose of the specification, the term "particle" refers to a discrete mass of material that is solid, e.g. at 20° C. or at room temperature or ambient temperature. Preferably a particle is solid at 20° C. Preferably, the individual particle(s) A are monoliths. The multitude of particles A, however, is not monolithic, but multiparticulate. Preferably, the pharmacologically active ingredient a and the constituents of the polymer matrix are intimately homogeneously distributed in the particle(s) A so that the particle(s) A do not contain any segments where either pharmacologically active ingredient a is present in the absence of polymer matrix or where polymer matrix is present in the absence of pharmacologically active ingredient a.

It is principally possible that the dosage form according to the invention comprises a single particle A.

In another preferred embodiment, the dosage form according to the invention comprises a plurality of particles A, more preferably a multitude of particles A.

In a preferred embodiment, the dosage form comprises at least 2, or at least 3, or at least 4, or at least 5 particles A. Preferably, the dosage form comprises not more than 10, or not more than 9, or not more than 8, or not more than 7 particles A.

In another preferred embodiment, the particles A amount to a total number within the range of from 20 to 600. More preferably, the dosage form comprises at least 30, or at least 60, or at least 90, or at least 120, or at least 150 particles A. Preferably, the dosage form comprises not more than 500, or not more than 400, or not more than 300, or not more than 200 particles A.

Preferably, when the dosage form contains more than a single particle A, the individual particles A may be of the same or of different size, shape and/or composition.

In a preferred embodiment, all particles A are made from the same mixture of ingredients and/or are substantially of the same size, shape, weight and composition.

In another preferred embodiment, particles A can be divided into at least 2 or at least 3 different types, e.g. particles $A_1$, particles $A_2$, and optionally particles $A_3$, that differ from one another in at least one property, preferably being selected from the group consisting of size, shape, weight, composition, release profile, breaking strength and resistance against solvent extraction.

The content of the particle(s) is not particularly limited and preferably amounts to a total content within the range of from 10 wt.-% to 80 wt.-%, based on the total weight of the dosage form. Preferably, the content of the particle(s) A in the dosage forms according to the invention is at most 99 wt.-%, or at most 98 wt.-%, or at most 96 wt.-%, or at most 94 wt.-%, more preferably at most 92 wt.-%, or at most 90 wt.-%, or at most 88 wt.-%, or at most 86 wt.-%, still more preferably at most 84 wt.-%, or at most 82 wt.-%, or at most 80 wt.-%, or at most 78 wt.-%, yet more preferably at most 76 wt.-%, or at most 74 wt.-%, or at most 72 wt.-%, or at most 70 wt.-%, most preferably at most 65 wt.-%, or at most 60 wt.-%, or at most 55 wt.-%, or at most 50 wt.-%, and in particular at most 45 wt.-%, or at most 40 wt.-%, or at most 35 wt.-%, or at most 30 wt.-%, based on the total weight of the dosage form.

Preferably, the content of the particle(s) A in the dosage forms according to the invention is at least 2.5 wt.-%, at least 3.0 wt.-%, at least 3.5 wt.-% or at least 4.0 wt.-%; more preferably at least 4.5 wt.-%, at least 5.0 wt.-%, at least 5.5 wt.-% or at least 6.0 wt.-%; still more preferably at least 6.5 wt.-%, at least 7.0 wt.-%, at least 7.5 wt.-% or at least 8.0 wt.-%; yet more preferably at least 8.5 wt.-%, at least 9.0 wt.-%, at least 9.5 wt.-% or at least 10 wt.-%; even more preferably at least 11 wt.-%, at least 12 wt.-%, at least 13 wt.-% or at least 14 wt.-%; most preferably at least 15 wt.-%, at least 17.5 wt.-%, at least 20 wt.-% or at least 22.5 wt.-%; and in particular at least 25 wt.-%, at least 27.5 wt.-%, at least 30 wt.-% or at least 35 wt.-%; based on the total weight of the dosage form.

In a preferred embodiment, the dosage form according to the invention comprises one or more particle(s) A comprising a pharmacologically active ingredient a as well as one or more particle(s) B comprising an optionally present pharmacologically active ingredient b. As besides the different pharmacologically active ingredient a and b, respectively, the particle(s) A and the particle(s) B have preferably, but independently of one another corresponding composition and properties, in the following it is referred to "particle(s)" meaning that these preferred embodiments independently apply to particle(s) A as well as to optionally present particle(s) B.

When the particle(s) are film coated, the polymer matrix is preferably homogeneously distributed in the core of the dosage form, i.e. the film coating preferably does not contain polymer matrix. Nonetheless, the film coating as such may of course contain one or more polymers, which however, preferably differ from the constituents of the polymer matrix contained in the core.

When the particle(s) are film coated, the pharmacologically active ingredient a/b is preferably homogeneously distributed in the core of the dosage form, i.e. the film coating preferably does not contain pharmacologically active ingredient a/b.

The shape of the particle(s) is not particularly limited. As the particle(s) are preferably manufactured by hot-melt extrusion, preferred particle(s) present in the dosage forms according to the invention are generally cylindrical in shape. The diameter of such particle(s) is therefore the diameter of their circular cross section. The cylindrical shape is caused by the extrusion process according to which the diameter of the circular cross section is a function of the extrusion die and the length of the cylinders is a function of the cutting length according to which the extruded strand of material is cut into pieces of preferably more or less predetermined length.

The suitability of cylindrical, i.e. a spherical particle(s) for the manufacture of the dosage forms according to the invention is unexpected. Typically, the aspect ratio is regarded as an important measure of the spherical shape. The aspect ratio is defined as the ratio of the maximal diameter ($d_{max}$) and its orthogonal Feret-diameter. For aspherical particle(s), the aspect ratio has values above 1. The smaller the value the more spherical is the particle(s). Aspect ratios below 1.1 are typically considered satisfactory, aspect ratios above 1.2, however, are typically considered not suitable for the manufacture of conventional dosage forms. The inventors have surprisingly found that when manufacturing the dosage forms according to the invention, even particle(s) having aspect ratios above 1.2 can be processed without difficulties and that it is not necessary to provide spherical particle(s). In a preferred embodiment, the aspect ratio of the particle(s) is at most 1.40, more preferably at most 1.35, still more preferably at most 1.30, yet more preferably at most 1.25, even more preferably at most 1.20, most preferably at most 1.15 and in particular at most 1.10. In another preferred embodiment, the aspect ratio of the particle(s) is at least 1.10, more preferably at least 1.15, still more preferably at least 1.20, yet more preferably at least 1.25, even more preferably at least 1.30, most preferably at least 1.35 and in particular at least 1.40.

The particle(s) are of macroscopic size, typically the average diameter is within the range of from 100 μm to 1500 μm, preferably 200 μm to 1500 μm, more preferably 300 μm to 1500 μm, still more preferably 400 μm to 1500 μm, most preferably 500 μm to 1500 μm, and in particular 600 μm to 1500 μm.

The particle(s) in the dosage forms according to the invention are of macroscopic size, i.e. typically have an average particle(s) size of at least 50 μm, more preferably at least 100 μm, still more preferably at least 150 μm or at least 200 μm, yet more preferably at least 250 μm or at least 300 μm, most preferably at least 400 μm or at least 500 μm, and in particular at least 550 μm or at least 600 μm.

Preferred particle(s) have an average length and average diameter of 1000 μm or less. When the particle(s) are manufactured by extrusion technology, the "length" of particle(s) is the dimension of the particle(s) that is parallel to the direction of extrusion. The "diameter" of particle(s) is the largest dimension that is perpendicular to the direction of extrusion.

Particularly preferred particle(s) have an average diameter of less than 1000 μm, more preferably less than 800 μm, still more preferably of less than 650 μm. Especially preferred particle(s) have an average diameter of less than 700 μm, particularly less than 600 μm, still more particularly less than 500 μm, e.g. less than 400 μm. Particularly preferred particle(s) have an average diameter in the range 200 to 1000 μm, more preferably 400 to 800 μm, still more preferably 450 to 700 μm, yet more preferably 500 to 650 μm, e.g. 500 to 600 μm. Further preferred particle(s) have an average diameter of between 300 μm and 400 μm, of between 400 μm and 500 μm, or of between 500 μm and 600 μm, or of between 600 μm and 700 μm or of between 700 μm and 800 μm.

Preferred particle(s) that are present in the dosage forms according to the invention have an average length of less than 1000 μm, preferably an average length of less than 800 μm, still more preferably an average length of less than 650 μm, e.g. a length of 800 μm, 700 μm 600 μm, 500 μm, 400 μm or 300 μm. Especially preferred particle(s) have an average length of less than 700 μm, particularly less than 650 μm, still more particularly less than 550 μm, e.g. less than 450 μm. Particularly preferred particle(s) therefore have an average length in the range 200-1000 μm, more preferably 400-800 μm, still more preferably 450-700 μm, yet more preferably 500-650 μm, e.g. 500-600 μm. The minimum average length of the microparticle(s) is determined by the cutting step and may be, e.g. 500 µm, 400 µm, 300 µm or 200 µm.

In a preferred embodiment, the particle(s) have (i) an average diameter of 1000±300 µm, more preferably 1000±250 µm, still more preferably 1000±200 µm, yet more preferably 1000±150 µm, most preferably 1000±100 µm, and in particular 1000±50 µm; and/or (ii) an average length of 1000±300 µm, more preferably 1000±250 µm, still more preferably 1000±200 µm, yet more preferably 1000±150 µm, most preferably 1000±100 µm, and in particular 1000±50 µm.

The size of particle(s) may be determined by any conventional procedure known in the art, e.g. laser light scattering, sieve analysis, light microscopy or image analysis.

Preferably, the individual particle(s) have a weight within the range of from 0.1 mg to 5.0 mg.

In preferred embodiments, the individual particle(s) preferably have a weight within the range of 1.0±0.9 mg, or 1.0±0.8 mg, or 1.0±0.7 mg, or 1.0±0.6 mg, or 1.0±0.5 mg, or 1.0±0.4 mg, or 1.0±0.3 mg; or 1.5±0.9 mg, or 1.5±0.8 mg, or 1.5±0.7 mg, or 1.5±0.6 mg, or 1.5±0.5 mg, or 1.5±0.4 mg, or 1.5±0.3 mg; or 2.0±0.9 mg, or 2.0±0.8 mg, or 2.0±0.7 mg, or 2.0±0.6 mg, or 2.0±0.5 mg, or 2.0±0.4 mg, or 2.0±0.3 mg; or 2.5±0.9 mg, or 2.5±0.8 mg, or 2.5±0.7 mg, or 2.5±0.6 mg, or 2.5±0.5 mg, or 2.5±0.4 mg, or 2.5±0.3 mg; or 3.0±0.9 mg, or 3.0±0.8 mg, or 3.0±0.7 mg, or 3.0±0.6 mg, or 3.0±0.5 mg, or 3.0±0.4 mg, or 3.0±0.3 mg.

Preferably, the particle(s) A have a total weight over all particles A within the range of from 10 mg to 500 mg. In preferred embodiments, the total weight of the particle(s) A is within the range of 180±170 mg, or 180±150 mg, or 180±130 mg, or 180±110 mg, or 180±90 mg, or 180±70 mg, or 180±50 mg, or 180±30 mg.

Preferably, the particle(s) that are contained in the dosage form according to the invention have an arithmetic average weight, in the following referred to as "aaw", wherein at least 70%, more preferably at least 75%, still more preferably at least 80%, yet more preferably at least 85%, most preferably at least 90% and in particular at least 95% of the individual particle(s) contained in said one or more particle(s) has an individual weight within the range of aaw±30%, more preferably aaw±25%, still more preferably aaw±20%, yet more preferably aaw±15%, most preferably aaw±10%, and in particular aaw±5%. For example, if the dosage form according to the invention contains a plurality of 100 particles and aaw of said plurality of particles is 1.00 mg, at least 75 individual particles (i.e. 75%) have an individual weight within the range of from 0.70 to 1.30 mg (1.00 mg±30%).

In a preferred embodiment, the particle(s) are not film coated. In another preferred embodiment, the particle(s) are film coated.

The particle(s) according to the invention can optionally be provided, partially or completely, with a conventional coating. The particle(s) according to the invention are preferably film coated with conventional film coating compositions. Suitable coating materials are commercially available, e.g. under the trademarks Opadry® and Eudragit®.

When the particle(s) are film coated, the content of the dried film coating is preferably at most 5 wt.-%, more preferably at most 4 wt.-%, still more preferably at most 3.5 wt.-%, yet more preferably at most 3 wt.-%, most preferably at most 2.5 wt.-%, and in particular at most 2 wt.-%, based on the total weight of the particle(s). In a particularly preferred embodiment, the weight increase based on the total weight of the dosage form and/or based on the total weight of the particle(s) (uncoated starting material) is within the range of from 3.0 to 4.7 wt.-%, more preferably 3.1 to 4.6 wt.-%, still more preferably 3.2 to 4.5 wt.-%, yet more preferably 3.3 to 4.4 wt.-%, most preferably 3.4 to 4.3 wt.-%, and in particular 3.5 to 4.2 wt.-%.

In a preferred embodiment of the invention, the film coating of the particle(s) A contains the total amount of the optionally present pharmacologically active ingredient b or a portion $b_C$ thereof.

The tamper-resistant dosage form according to the invention comprises one or more particle(s) A which comprise a polymer matrix, wherein the polymer matrix preferably comprises a polyalkylene oxide, preferably at a content of at least 25 wt.-%, based on the total weight of the dosage form and/or based on the total weight of the particle(s) A. The optionally present particle(s) B may also, independently of the particle(s) A, comprise a polymer matrix, wherein the polymer matrix preferably comprises a polyalkylene oxide, preferably at a content of at least 25 wt.-%, based on the total weight of the dosage form and/or based on the total weight of the particle(s) B.

Preferably, the polyalkylene oxide is selected from polymethylene oxide, polyethylene oxide and polypropylene oxide, or copolymers thereof. Polyethylene oxide is preferred.

Preferably, the polyalkylene oxide has a weight average molecular weight of at least 200,000 g/mol, more preferably at least 500,000 g/mol. In a preferred embodiment, the polyalkylene oxide has a weight average molecular weight ($M_W$) or viscosity average molecular weight ($M_\eta$) of at least 750,000 g/mol, preferably at least 1,000,000 g/mol or at least 2,500,000 g/mol, more preferably in the range of 1,000,000 g/mol to 15,000,000 g/mol, and most preferably in the range of 5,000,000 g/mol to 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Polyalkylene oxide may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the dosage form is at least 200,000 g/mol. Thus, polyalkylene glycols, if any, are preferably not taken into consideration when determining the weight average molecular weight of polyalkylene oxide.

The polyalkylene oxide may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof (e.g., Poloxamer®), and mixtures of at least two of the stated polymers, or other polymers with the above characteristics.

Preferably, the molecular weight dispersity $M_w/M_n$ of polyalkylene oxide is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt.-% aqueous solution using the stated viscosimeter (spindle no. 2/rotational speed 2 rpm).

Polyethylene oxide that is suitable for use in the dosage forms according to the invention is commercially available from Dow. For example, Polyox WSR N-12K, Polyox N-60K, Polyox WSR 301 NF or Polyox WSR 303NF may be used in the dosage forms according to the invention. For details concerning the properties of these products, it can be referred to e.g. the product specification.

Preferably, the content of the polyalkylene oxide is within the range of from 25 to 80 wt.-%, more preferably 25 to 75 wt.-%, still more preferably 25 to 70 wt.-%, yet more preferably 25 to 65 wt.-%, most preferably 30 to 65 wt.-% and in particular 35 to 65 wt.-%, based on the total weight of the dosage form and/or based on the total weight of the particle(s). In a preferred embodiment, the content of the polyalkylene oxide is at least 30 wt.-%, more preferably at least 35 wt.-%, still more preferably at least 40 wt.-%, yet more preferably at least 45 wt.-% and in particular at least 50 wt.-%, based on the total weight of the dosage form and/or based on the total weight of the particle(s).

In a preferred embodiment, the overall content of polyalkylene oxide is within the range of 35±8 wt.-%, more preferably 35±6 wt.-%, most preferably 35±4 wt.-%, and in particular 35±2 wt.-%, based on the total weight of the dosage form and/or based on the total weight of the particle(s). In another preferred embodiment, the overall content of polyalkylene oxide is within the range of 40±12 wt.-%, more preferably 40±10 wt.-%, most preferably 40±7 wt.-%, and in particular 40±3 wt.-%, based on the total weight of the dosage form and/or based on the total weight of the particle(s). In still another preferred embodiment, the overall content of polyalkylene oxide is within the range of 45±16 wt.-%, more preferably 45±12 wt.-%, most preferably 45±8 wt.-%, and in particular 45±4 wt.-%, based on the total weight of the dosage form and/or based on the total weight of the particle(s). In yet another preferred embodiment, the overall content of polyalkylene oxide is within the range of 50±20 wt.-%, more preferably 50±15 wt.-%, most preferably 50±10 wt.-%, and in particular 50±5 wt.-%, based on the total weight of the dosage form and/or based on the total weight of the particle(s). In a further preferred embodiment, the overall content of polyalkylene oxide is within the range of 55±20 wt.-%, more preferably 55±15 wt.-%, most preferably 55±10 wt.-%, and in particular 55±5 wt.-%, based on the total weight of the dosage form and/or based on the total weight of the particle(s). In still a further preferred embodiment, the overall content of polyalkylene oxide is within the range of 60±20 wt.-%, more preferably 60±15 wt.-%, most preferably 60±10 wt.-%, and in particular 60±5 wt.-%. In a still further a preferred embodiment, the overall content of polyalkylene oxide is within the range of 65±20 wt.-%, more preferably 65±15 wt.-%, and most preferably 65±10 wt.-%, and in particular 65±5 wt.-%, based on the total weight of the dosage form and/or based on the total weight of the particle(s).

Preferably, the relative weight ratio of the polyalkylene oxide to the pharmacologically active ingredient a is within the range of 30:1 to 1:10, more preferably 20:1 to 1:1, still more preferably 15:1 to 5:1, yet more preferably 14:1 to 6:1, most preferably 13:1 to 7:1, and in particular 12:1 to 8:1.

Preferably, the total content of the polyalkylene oxide in the pharmaceutical dosage form according to the invention amounts to at least 25 mg, or at least 30 mg, or at least 35 mg, or at least 40 mg, or at least 45 mg; more preferably at least 50 mg, or at least 55 mg, or at least 60 mg, or at least 65 mg, or at least 70 mg, or at least 75 mg; still more preferably at least 80 mg, or at least 85 mg, or at least 90 mg, or at least 95 mg; and most preferably at least 100 mg.

The dosage form according to the invention is preferably tamper-resistant.

As used herein, the term "tamper-resistant" refers to dosage forms that are preferably resistant to conversion into a form suitable for misuse or abuse, particular for nasal and/or intravenous administration, by conventional means such as grinding in a mortar or crushing by means of a hammer. In this regard, the dosage forms as such may be crushable by conventional means. However, the particle(s) A contained in the dosage forms according to the invention preferably exhibit mechanical properties such that they cannot be pulverized by conventional means any further. The same may independently apply to the optionally present particle(s) B. As the particle(s) A are of macroscopic size and contain the pharmacologically active ingredient a, and as the optionally present particle(s) B may independently be of macroscopic size and contain the optionally present pharmacologically active ingredient b, they cannot be administered nasally thereby rendering the dosage forms tamper-resistant.

Preferably, the particle(s) A have a breaking strength of at least 300 N. Preferably, the overall dosage form as such does not have a breaking strength of at least 300 N, i.e. typically the breaking strength of the dosage form as such, e.g. of the tablet or capsule, is below 300 N.

When the dosage form additionally contains particle(s) B, these particle(s) B may also have a breaking strength of at least 300 N. However, though being less preferred, the invention also includes embodiments where optionally present particle(s) B do not have a breaking strength of at least 300 N.

Preferably, the particle(s) are tamper-resistant as such so that they also provide tamper-resistance after they have been separated from the remaining constituents of the dosage form. Thus, preferably the particle(s) as such contain all ingredients that are necessary to render them tamper-resistant.

Preferably, when trying to tamper the dosage form in order to prepare a formulation suitable for abuse by intravenous administration, the liquid part of the formulation that can be separated from the remainder by means of a syringe is as less as possible, preferably it contains not more than 20 wt.-%, more preferably not more than 15 wt.-%, still more preferably not more than 10 wt.-%, and most preferably not more than 5 wt.-% of the originally contained pharmacologically active ingredient a.

The same may apply to optionally present pharmacologically active ingredient b. However, in a preferred embodiment pharmacologically active ingredient a is more prone to abuse than optionally present pharmacologically active ingredient b.

Preferably, this property is tested by (i) dispensing a dosage form that is either intact or has been manually comminuted by means of two spoons in 5 ml of purified water, (ii) heating the liquid up to its boiling point, (iii) boiling the liquid in a covered vessel for 5 min without the addition of further purified water, (iv) drawing up the hot liquid into a syringe (needle 21G equipped with a cigarette filter), (v) determining the amount of the pharmacologically active ingredient a and/or b contained in the liquid within the syringe.

Further, when trying to disrupt the dosage forms by means of a hammer or mortar, the particle(s) preferably tend to adhere to one another thereby forming aggregates and agglomerates, respectively, which are larger in size than the untreated particle(s).

Preferably, tamper-resistance is achieved based on the mechanical properties of the particle(s) so that comminution is avoided or at least substantially impeded. According to the invention, the term comminution means the pulverization of the particle(s) using conventional means usually available to an abuser, for example a pestle and mortar, a hammer, a mallet or other conventional means for pulverizing under the action of force. Thus, tamper-resistance preferably means that pulverization of the particle(s) using conventional means is avoided or at least substantially impeded.

Preferably, the mechanical properties of the particle(s) according to the invention, particularly their breaking strength and deformability, substantially rely on the presence and spatial distribution of a polymer matrix, preferably comprising polyalkylene oxide, although its mere presence does typically not suffice in order to achieve said properties. The advantageous mechanical properties of the particle(s) according to the invention may not automatically be achieved by simply processing pharmacologically active ingredient a/b, the components of the polymer matrix such as polyalkylene oxide, and optionally further excipients by means of conventional methods for the preparation of dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the particle(s) exhibiting the desired properties may be obtained only if, during preparation of the particle(s),
- suitable components
- in suitable amounts
- are exposed to
- a sufficient pressure
- at a sufficient temperature
- for a sufficient period of time.

Thus, regardless of the apparatus used, the process protocols must be adapted in order to meet the required criteria. Therefore, the breaking strength and deformability of the particle(s) is separable from the composition.

The particle(s) contained in the dosage form according to the invention preferably have a breaking strength of at least 300 N, at least 400 N, or at least 500 N, preferably at least 600 N, more preferably at least 700 N, still more preferably at least 800 N, yet more preferably at least 1000 N, most preferably at least 1250 N and in particular at least 1500 N.

In order to verify whether a particle(s) exhibits a particular breaking strength of e.g. 300 N or 500 N it is typically not necessary to subject said particle(s) to forces much higher than 300 N and 500 N, respectively. Thus, the breaking strength test can usually be terminated once the force corresponding to the desired breaking strength has been slightly exceeded, e.g. at forces of e.g. 330 N and 550 N, respectively.

The "breaking strength" (resistance to crushing) of a dosage form and of a particle(s) is known to the skilled person. In this regard it can be referred to, e.g., W. A. Ritschel, Die Tablette, 2. Auflage, Editio Cantor Verlag Aulendorf, 2002; H Liebermann et al., Dosage forms: Dosage forms, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the particle(s) (=breaking force). Therefore, for the purpose of the specification a particle does preferably not exhibit the desired breaking strength when it breaks, i.e., is fractured into at least two independent parts that are separated from one another.

In another preferred embodiment, however, the particle is regarded as being broken if the force decreases by 50% (threshold value) of the highest force measured during the measurement (see below).

The particle(s) according to the invention are distinguished from conventional particles that can be contained in dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles. Avoidance of pulverization virtually rules out oral or parenteral, in particular intravenous or nasal abuse.

Conventional particles typically have a breaking strength well below 200 N.

The breaking strength of conventional round dosage forms/particle may be estimated according to the following empirical formula: Breaking Strength [in N]=10× Diameter Of The Dosage form/Particle [in mm]. Thus, according to said empirical formula, a round dosage form/particle having a breaking strength of at least 300 N would require a diameter of at least 30 mm. Such a particles, however, could not be swallowed, let alone a dosage form containing a plurality of such particles. The above empirical formula preferably does not apply to the particle(s) according to the invention, which are not conventional but rather special.

Further, the actual mean chewing force is 220 N (cf., e.g., P. A. Proeschel et al., J Dent Res, 2002, 81(7), 464-468). This means that conventional particles having a breaking strength well below 200 N may be crushed upon spontaneous chewing, whereas the particle(s) according to the invention may preferably not.

Still further, when applying a gravitational acceleration of 9.81 m/s$^2$, 300 N correspond to a gravitational force of more than 30 kg, i.e. the particle(s) according to the invention can preferably withstand a weight of more than 30 kg without being pulverized.

Methods for measuring the breaking strength of a dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Dosage forms". The test is intended to determine, under defined conditions, the resistance to crushing of dosage forms and of the particle(s), respectively, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the dosage form and a single particle, respectively. The apparatus is calibrated using a system with a precision of 1 Newton. The dosage form and particle, respectively, is placed between the jaws, taking into account, where applicable, the shape, the break-mark and the inscription; for each measurement the dosage form and particle, respectively, is oriented in the same way with respect to the direction of application of the force (and the direction of extension in which the breaking strength is to be measured). The measurement is carried out on 10 dosage forms and particles, respectively, taking care that all fragments have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a dosage form and particle, respectively, to fail (i.e., break) in a specific plane. The dosage forms and particle, respectively, are generally placed between two platens, one of which moves to apply sufficient force to the dosage form and particle, respectively, to cause fracture. For conventional, round (circular cross-section) dosage forms and particles, respectively, loading occurs across their diameter (sometimes referred to as diametral loading), and fracture occurs in the plane. The breaking force of a dosage form and a particle, respectively, is commonly called hardness in the pharmaceutical literature; however, the use of this term is misleading. In material science, the term hardness refers to the resistance of a surface to penetration or indentation by a small probe. The term crushing strength is also frequently used to describe the resistance of dosage forms and particles, respectively, to the application of a compressive load. Although this term describes the true nature of the test more accurately than does hardness, it implies that dosage forms and particles, respectively, are actually crushed during the test, which is often not the case.

Alternatively, the breaking strength (resistance to crushing) can be measured in accordance with WO 2008/107149, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. A skilled person knows how to properly adjust the test speed, e.g. to 10 mm/min, 20 mm/min, or 40 mm/min, for example. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

When using the testControl software (testXpert V10.11), the following exemplified settings and parameters have revealed to be useful: LE-position: clamping length 150 mm. LE-speed: 500 mm/min, clamping length after pre-travel: 195 mm, pre-travel speed: 500 mm/min, no pre-force control—pre-force: pre-force 1N, pre-force speed 10 mm/min—sample data: no sample form, measuring length traverse distance 10 mm, no input required prior to testing—testing/end of test; test speed: position-controlled 10 mm/min, delay speed shift: 1, force shut down threshold 50% $F_{max}$, no force threshold for break-tests, no max length variation, upper force limit: 600N—expansion compensation: no correction of measuring length—actions after testing: LE to be set after test, no unload of sample—TRS: data memory: TRS distance interval until break 1 TRS time interval 0.1 s, TRS force interval 1N—machine; traverse distance controller: upper soft end 358 mm, lower soft end 192 mm—lower test space. Parallel arrangement of the upper plate and the ambos should be ensured—these parts must not touch during or after testing. After testing, a small gap (e.g. 0.1 or 0.2 mm) should still be present between the two brackets in intimated contact with the tested particle, representing the remaining thickness of the deformed particle.

In a preferred embodiment, the particle is regarded as being broken if it is fractured into at least two separate pieces of comparable morphology. Separated matter having a morphology different from that of the deformed particle, e.g. dust, is not considered as pieces qualifying for the definition of breaking.

The particle(s) according to the invention preferably exhibit mechanical strength over a wide temperature range, in addition to the breaking strength (resistance to crushing) optionally also sufficient hardness, yield strength, fatigue strength, impact resistance, impact elasticity, tensile strength, compressive strength and/or modulus of elasticity, optionally also at low temperatures (e.g. below −24° C., below −40° C. or possibly even in liquid nitrogen), for it to be virtually impossible to pulverize by spontaneous chewing, grinding in a mortar, pounding, etc. Thus, preferably, the comparatively high breaking strength of the particle(s) according to the invention is maintained even at low or very low temperatures, e.g., when the dosage form is initially chilled to increase its brittleness, for example to temperatures below −25° C., below −40° C. or even in liquid nitrogen.

The particle(s) according to the invention are preferably characterized by a certain degree of breaking strength. This does not mean that the particle(s) must also exhibit a certain degree of hardness. Hardness and breaking strength are different physical properties. Therefore, the tamper-resistance of the dosage form does not necessarily depend on the hardness of the particle(s). For instance, due to their breaking strength, impact strength, elasticity modulus and tensile strength, respectively, the particle(s) can preferably be deformed, e.g. plastically, when exerting an external force, for example using a hammer, but cannot be pulverized, i.e., crumbled into a high number of fragments. In other words, the particle(s) according to the invention are preferably characterized by a certain degree of breaking strength, but not necessarily also by a certain degree of form stability.

Therefore, in the meaning of the specification, a particle that is deformed when being exposed to a force in a particular direction of extension but that does not break (plastic deformation or plastic flow) is preferably to be regarded as having the desired breaking strength in said direction of extension.

Preferred particle(s) present in the dosage forms according to the invention are those having a suitable tensile strength as determined by a test method currently accepted in the art. Further preferred particle(s) are those having a Youngs Modulus as determined by a test method of the art. Still further preferred particle(s) are those having an acceptable elongation at break.

Irrespective of whether the particle(s) according to the invention have an increased breaking strength or nor, the particle(s) according to the invention preferably exhibit a certain degree of deformability. The particle(s) contained in the dosage form according to the invention preferably have a deformability such that they show an increase, preferably a substantially steady increase of the force at a corresponding decrease of the displacement in the force-displacement-diagram when being subjected to a breaking strength test as described above.

Figure 1:
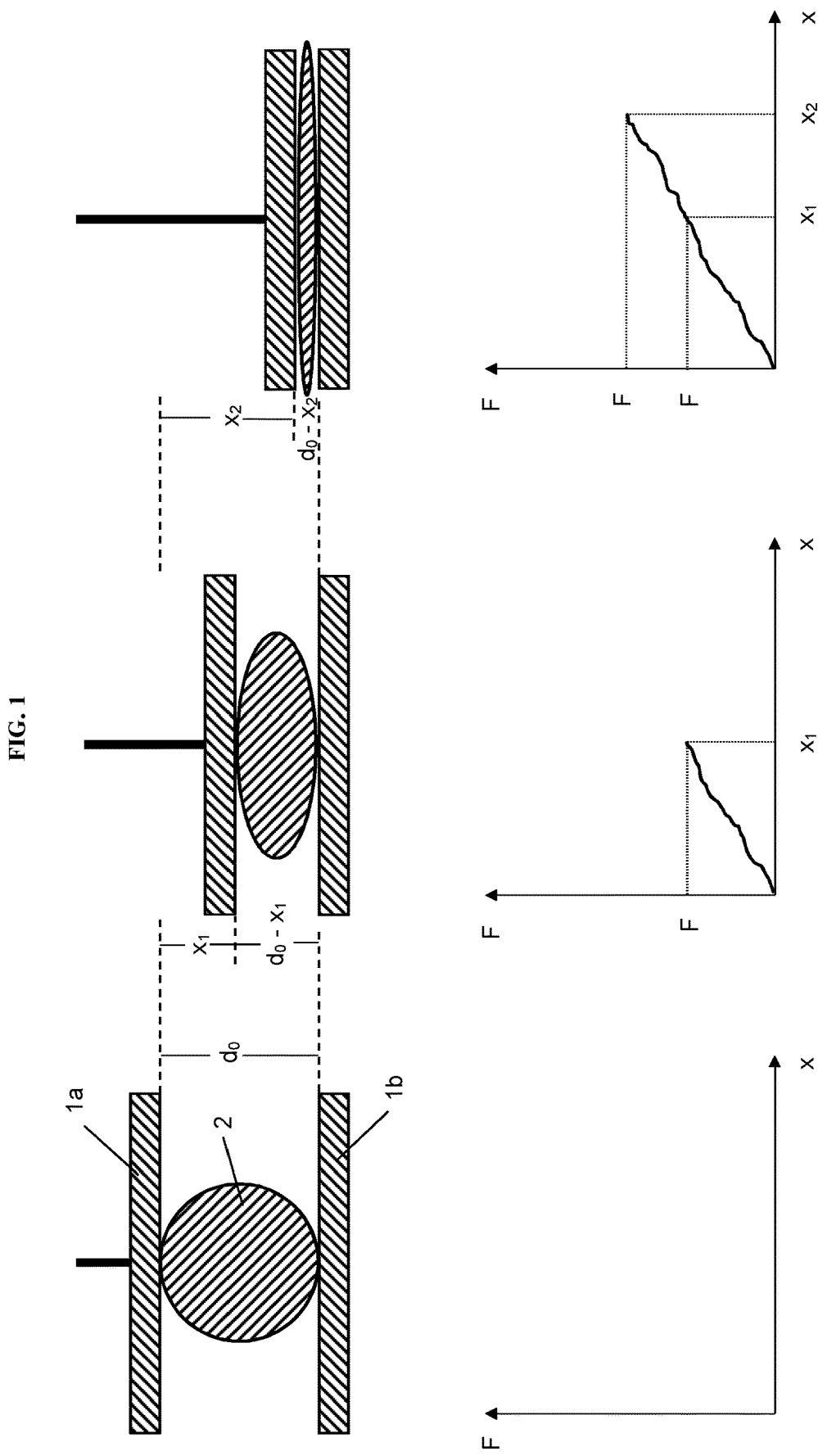
FIG. 1 illustrates the preferred behavior of the particle(s) contained in the dosage form according to the invention when being subjected to a breaking strength test, in particular their deformability.
Figure 2:
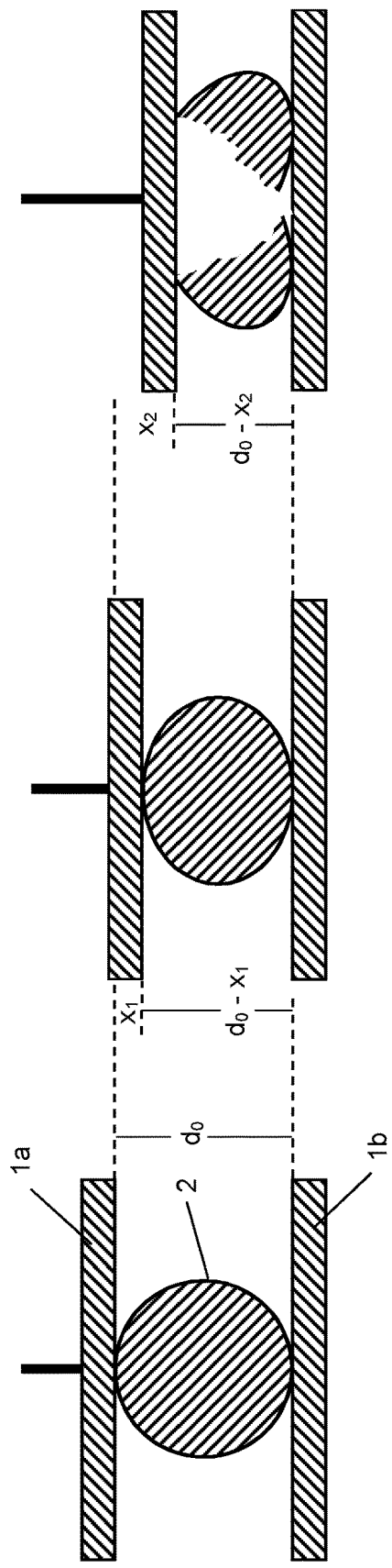
FIG. 2 illustrates the behavior of conventional particle(s) when being subjected to a breaking strength test.

This mechanical property, i.e. the deformability of the individual particle(s), is illustrated in FIGS. 1 and 2.

FIG. 1 schematically illustrates the measurement and the corresponding force-displacement-diagram. In particular, FIG. 1A shows the initial situation at the beginning of the measurement. The sample particle (2) is placed between upper jaw (1a) and lower jaw (1b) which each are in intimate contact with the surface of the particle (2). The initial displacement $d_0$ between upper jaw (1a) and lower jaw (1b) corresponds to the extension of the particle orthogonal to the surfaces of upper jaw (1a) and lower jaw (1b). At this time, no force is exerted at all and thus, no graph is displayed in the force-displacement-diagram below. When the measurement is commenced, the upper jaw is moved in direction of lower jaw (1b), preferably at a constant speed. FIG. 1B shows a situation where due to the movement of upper jaw (1a) towards lower jaw (1b) a force is exerted on particle (2). Because of its deformability, the particle (2) is flattened without being fractured. The force-displacement-diagram indicates that after a reduction of the displacement $d_0$ of upper jaw (1a) and lower jaw (1b) by distance $x_1$, i.e. at a displacement of $d_1=d_0-x_1$, a force $F_1$ is measured. FIG. 1C shows a situation where due to the continuous movement of upper jaw (1a) towards lower jaw (1b), the force that is exerted on particle (2) causes further deformation, although the particle (2) does not fracture. The force-displacement-diagram indicates that after a reduction of the displacement $d_0$ of upper jaw (1a) and lower jaw (1b) by distance $x_2$, i.e. at a displacement of $d_2=d_0-x_2$, a force $F_2$ is measured. Under these circumstances, the particle (2) has not been broken (fractured) and a substantially steady increase of the force in the force-displacement-diagram is measured.

In contrast, FIG. 2 schematically illustrates the measurement and the corresponding force-displacement-diagram of a conventional comparative particle not having the degree of deformability as the particle(s) according to the invention. FIG. 2A shows the initial situation at the beginning of the measurement. The comparative sample particle (2) is placed between upper jaw (1a) and lower jaw (1b) which each are in intimate contact with the surface of the comparative particle (2). The initial displacement $d_0$ between upper jaw (1a) and lower jaw (1b) corresponds to the extension of the comparative particle orthogonal to the surfaces of upper jaw (1a) and lower jaw (1b). At this time, no force is exerted at all and thus, no graph is displayed in the force-displacement-diagram below. When the measurement is commenced, the upper jaw is moved in direction of lower jaw (1b), preferably at a constant speed. FIG. 2B shows a situation where due to the movement of upper jaw (1a) towards lower jaw (1b) a force is exerted on comparative particle (2). Because of some deformability, the comparative particle (2) is slightly flattened without being fractured. The force-displacement-diagram indicates that after a reduction of the displacement $d_0$ of upper jaw (1a) and lower jaw (1b) by distance $x_1$, i.e. at a displacement of $d_1=d_0-x_1$, a force $F_1$ is measured. FIG. 2C shows a situation where due to the continuous movement of upper jaw (1a) towards lower jaw (1b), the force that is exerted on particle (2) causes sudden fracture of the comparative particle (2). The force-displacement-diagram indicates that after a reduction of the displacement $d_0$ of upper jaw (1a) and lower jaw (1b) by distance $x_2$, i.e. at a displacement of $d_2=d_0-x_2$, a force $F_2$ is measured that suddenly drops when the particle fractures. Under these circumstances, the particle (2) has been broken (fractured) and no steady increase of the force in the force-displacement-diagram is measured. The sudden drop (decrease) of the force can easily be recognized and does not need to be quantified for the measurement. The steady increase in the force-displacement-diagram ends at displacement $d_2=d_0-x_2$ when the particle breaks.

In a preferred embodiment, the particle(s) contained in the dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (1a) and lower jaw (1b) has been reduced to a value of 90% of the original displacement $d_0$ (i.e. $d=0.9 \cdot d_0$), preferably to a displacement d of 80% of the original displacement $d_0$, more preferably to a displacement d of 70% of the original displacement $d_0$, still more preferably to a displacement d of 60% of the original displacement $d_0$, yet more preferably to a displacement d of 50% of the original displacement $d_0$, even more preferably to a displacement d of 40% of the original displacement $d_0$, most preferably to a displacement d of 30% of the original displacement $d_0$, and in particular to a displacement d of 20% of the original displacement $d_0$, or to a displacement d of 15% of the original displacement $d_0$, to a displacement d of 10% of the original displacement $d_0$, or to a displacement d of 5% of the original displacement $d_0$.

In another preferred embodiment, the particle(s) contained in the dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), preferably at least until the displacement d of upper jaw (1a) and lower jaw (1b) has been reduced to 0.80 mm or 0.75 mm, preferably 0.70 mm or 0.65 mm, more preferably 0.60 mm or 0.55 mm, still more preferably 0.50 mm or 0.45 mm, yet more preferably 0.40 mm or 0.35 mm, even more preferably 0.30 mm or 0.25 mm, most preferably 0.20 mm or 0.15 mm and in particular 0.10 or 0.05 mm.

In still another preferred embodiment, the particle(s) contained in the dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (1a) and lower jaw (1b) has been reduced to 50% of the original displacement $d_0$ (i.e. $d=d_0/2$), whereas the force measured at said displacement ($d=d_0/2$) is at least 25 N or at least 50 N, preferably at least 75 N or at least 100 N, still more preferably at least 150 N or at least 200 N, yet more preferably at least 250 N or at least 300 N, even more preferably at least 350 N or at least 400 N, most preferably at least 450 N or at least 500 N, and in particular at least 625 N, or at least 750 N, or at least 875 N, or at least 1000 N, or at least 1250 N, or at least 1500 N.

In another preferred embodiment, the particle(s) contained in the dosage form according to the invention have a deformability such that they show an increase, preferably a substantially steady increase of the force at a corresponding decrease of the displacement in the force-displacement-diagram when being subjected to a breaking strength test as described above ("Zwick Z 2.5" materials tester, constant speed), at least until the displacement d of upper jaw (1a) and lower jaw (1b) has been reduced by at least 0.1 mm, more preferably at least 0.2 mm, still more preferably at least 0.3 mm, yet more preferably at least 0.4 mm, even more preferably at least 0.5 mm, most preferably at least 0.6 mm, and in particular at least 0.7 mm, whereas the force measured at said displacement is within the range of from 5.0 N to 250 N, more preferably from 7.5 N to 225 N, still more preferably from 10 N to 200 N, yet more preferably from 15 N to 175 N, even more preferably from 20 N to 150 N, most preferably from 25 N to 125 N, and in particular from 30 N to 100 N.

In yet another embodiment, the particle(s) contained in the dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at most 90% of the original displacement $d_0$ (i.e. $d \leq 0.9 \cdot d_0$), preferably at most 80% of the original displacement $d_0$ (i.e. $d \leq 0.8 \cdot d_0$), more preferably at most 70% of the original displacement $d_0$ (i.e. $d \leq 0.7 \cdot d_0$), still more preferably at most 60% of the original displacement $d_0$ (i.e. $d \leq 0.6 \cdot d_0$), yet more preferably at most 50% of the original displacement $d_0$ (i.e. $d \leq 0.5 \cdot d_0$), even more preferably at most 40% of the original displacement $d_0$ (i.e. $d \leq 0.4 \cdot d_0$), most preferably at most 30% of the original displacement $d_0$ (i.e. $d \leq 0.3 \cdot d_0$), and in particular at most 20% of the original displacement $d_0$ (i.e. $d \leq 0.2 \cdot d_0$), or at most 15% of the original displacement $d_0$ (i.e. $d \leq 0.15 \cdot d_0$), at most 10% of the original displacement $d_0$ (i.e. $d \leq 0.1 \cdot d_0$), or at most 5% of the original displacement $d_0$ (i.e. $d \leq 0.05 \cdot d_0$).

Preferably, the particle(s) contained in the dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at most 0.80 mm or at most 0.75 mm, preferably at most 0.70 mm or at most 0.65 mm, more preferably at most 0.60 mm or at most 0.55 mm, still more preferably at most 0.50 mm or at most 0.45 mm, yet more preferably at most 0.40 mm or at most 0.35 mm, even more preferably at most 0.30 mm or at most 0.25 mm, most preferably at most 0.20 mm or at most 0.15 mm and in particular at most 0.10 or at most 0.05 mm.

In another embodiment, the particle(s) contained in the dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at least 5% of the original displacement $d_0$ (i.e. $d \geq 0.05 \cdot d_0$), preferably at least 10% of the original displacement $d_0$ (i.e. $d \geq 0.1 \cdot d_0$), more preferably at least 15% of the original displacement $d_0$ (i.e. $d \geq 0.15 \cdot d_0$), still more preferably at least 20% of the original displacement $d_0$ (i.e. $d \geq 0.2 \cdot d_0$), yet more preferably at least 30% of the original displacement $d_0$ (i.e. $d \geq 0.3 \cdot d_0$), even more preferably at least 40% of the original displacement $d_0$ (i.e. $d \geq 0.4 \cdot d_0$), most preferably at least 50% of the original displacement $d_0$ (i.e. $d \geq 0.5 \cdot d_0$), and in particular at least 60% of the original displacement $d_0$ (i.e. $d \geq 0.6 \cdot d_0$), or at least 70% of the original displacement $d_0$ (i.e. $d \geq 0.7 \cdot d_0$), at least 80% of the original displacement $d_0$ (i.e. $d \geq 0.8 \cdot d_0$), or at least 90% of the original displacement $d_0$ (i.e. $d \geq 0.9 \cdot d_0$).

Preferably, the particle(s) contained in the dosage form according to the invention have a deformability such that they are deformed without being fractured when subjected to a constant force of e.g. 50 N, 100 N, 200 N, 300 N, 400 N, 500 N or 600 N in a breaking strength test as described above ("Zwick Z 2.5" materials tester, constant force), until the displacement d of upper jaw (1a) and lower jaw (1b) is reduced so that no further deformation takes place at said constant force, whereas at this equilibrated state the displacement d of upper jaw (1a) and lower jaw (1b) is at least 0.05 mm or at least 0.10 mm, preferably at least 0.15 mm or at least 0.20 mm, more preferably at least 0.25 mm or at least 0.30 mm, still more preferably at least 0.35 mm or at least 0.40 mm, yet more preferably at least 0.45 mm or at least 0.50 mm, even more preferably at least 0.55 mm or at least 0.60 mm, most preferably at least 0.65 mm or at least 0.70 mm and in particular at least 0.75 or at least 0.80 mm.

In particularly preferred embodiments, the dosage form according to the invention comprises a multitude of particles A which

- amount to a total number within the range of from 20 to 600; and/or
- are made from substantially the same mixture of ingredients; and/or
- have substantially of the same size, shape, weight and composition; and/or
- have cylindrical shape; and/or
- have substantially the same breaking strength;
- have a breaking strength of at least 300 N; and/or
- have an average individual weight within the range of from 0.1 mg to 5 mg; and/or
- have a total weight within the range of from 10 mg to 500 mg; and/or amount to a total content within the range of from 10 wt.-% to 80 wt.-%, based on the total weight of the dosage form; and/or are tamper-resistant as such so that they also provide tamper-resistance after they have been separated from the remaining constituents of the dosage form; and/or contain the total amount of the pharmacologically active ingredient a that is contained in the dosage form; and/or have substantially the same content of pharmacologically active ingredient a; and/or show substantially the same in vitro release profile; and/or after 30 min under in vitro conditions have released at least 80 wt.-% of the pharmacologically active ingredient a that was originally contained in the dosage form; and/or are thermoformed by hot-melt extrusion.

In preferred embodiments, the dosage form according to the invention comprises at least a portion of the optionally present pharmacologically active ingredient b outside the particle(s) A in an outer matrix material, which preferably comprises granules comprising optionally present pharmacologically active ingredient b and excipients selected from binders, fillers, disintegrants, lubricants, and the like. The outer matrix material may also comprise the optionally present granule(s) B and the optionally present portion $b_P$ of the optionally present pharmacologically active ingredient b that is present in form of a powder outside particle(s) A and B.

In a preferred embodiment, the total amount of the optionally present pharmacologically active ingredient b that is contained in the dosage form according to the invention is contained outside the particle(s) A in the outer matrix material, preferably in the granules that are part of said outer matrix material.

In another preferred embodiment, a portion $b_G$ of the total amount of the optionally present pharmacologically active ingredient b that is contained in the dosage form according to the invention is contained in the outer matrix material, preferably in the granules that are part of said outer matrix material, whereas the remainder of the optionally present pharmacologically active ingredient b is contained elsewhere in the dosage form according to the invention.

When a portion of the optionally present pharmacologically active ingredient b is present in the one or more particle(s) A, said portion is referred to as "portion $b_A$". Said portion $b_A$ is neither contained in particle(s) B, nor is it contained in a coating of particle(s) A, nor is it present in form of a powder, nor is it present in form of granules.

When a portion of the optionally present pharmacologically active ingredient b is present outside the particle(s) A in one or more particle(s) B, said portion is referred to as "portion $b_B$". Said portion $b_B$ is neither contained in particle(s) A, nor is it contained in a coating of particle(s) A, nor is it present in form of a powder, nor is it present in form of granules.

When a portion of the optionally present pharmacologically active ingredient b is present outside the particle(s) A in a coating of particle(s) A, said portion is referred to as "portion $b_C$". Said portion $b_C$ is neither contained in particle(s) A, nor is it contained in particle(s) A, nor is it present in form of a powder, nor is it present in form of granules.

When a portion of the optionally present pharmacologically active ingredient b is present outside the particle(s) A in the outer matrix material, preferably in the granules that are part of said outer matrix material, said portion is referred to as "portion $b_G$". Said portion $b_G$ is neither contained in particle(s) A, nor is it contained in a coating of particle(s) A, nor is it contained in particle(s) B, nor is it present in form of a powder.

When a portion of the optionally present pharmacologically active ingredient b is present outside the particle(s) A in form of a powder, said portion is referred to as "portion $b_P$". Said portion $b_P$ is neither contained in particle(s) A, nor is it contained in a coating of particle(s) A, nor is it contained in particle(s) B, nor is it present in form of granules.

Preferably, when the total amount of the optionally present pharmacologically active ingredient b is divided into portions that are present at different locations of the dosage form, the total amount of the optionally present pharmacologically active ingredient b is preferably divided in not more than three portions, more preferably not more than two portions.

Thus, when the total amount of the optionally present pharmacologically active ingredient b is divided into two portions, portion $b_G$ is present the outer matrix material, preferably in the granules that are part of said outer matrix material, whereas preferably the entire remainder amount of the optionally present pharmacologically active ingredient b, which is not present in the granules that are part of said outer matrix material, is present either as portion $b_A$ in the particle(s) A, or as portion $b_B$ in particle(s) B, or as portion $b_C$ in a coating of particle(s) A, or as portion $b_P$ outside particle(s) A in form of a powder.

Preferably, the relative weight ratio of portion $b_G$ to portion $b_A$, or the relative weight ratio of portion $b_G$ to portion $b_B$, or the relative weight ratio of portion $b_G$ to portion $b_C$, or the relative weight ratio of portion $b_G$ to portion $b_P$, is within the range of from 100:1 to 1:100, more preferably 50:1 to 1:50, still more preferably 10:1 to 1:10, yet more preferably 5:1 to 1:5.

In a preferred embodiment, the weight of portion $b_G$ is greater than the weight of portion $b_A$, or the weight of portion $b_G$ is greater than the weight of portion $b_B$, or the weight of portion $b_G$ is greater than the weight of portion $b_C$, or the weight of portion $b_G$ is greater than the weight of portion $b_P$.

In another preferred embodiment, the weight of portion $b_A$ is greater than the weight of portion $b_G$, or the weight of portion $b_B$ is greater than the weight of portion $b_G$, or the weight of portion $b_C$ is greater than the weight of portion $b_G$, or the weight of portion $b_P$ is greater than the weight of portion $b_G$.

In a preferred embodiment, the dosage form according to the invention is a tablet, wherein the particle(s) A are contained in an outer matrix material. The "outer matrix material" is not to be confused with the "polymer matrix" of the particle(s) A and the optionally present particle(s) B. In the following, this preferred embodiment is referred to as the "preferred tablet according to the invention".

When the preferred tablet according to the invention comprises particle(s) B, the following preferred embodiments described for particles(s) A may also analogously and independently apply to particle(s) B. Thus, in the following it is generally referred to "the particle(s)" when no specific distinction between particle(s) A and the optionally present particle(s) B is necessary, nevertheless implying the quality and quantity of particle(s) A and particle(s) B are still independent of one another.

The preferred tablet according to the invention comprises subunits having different morphology and properties, namely particle(s) and outer matrix material, wherein the particle(s) form a discontinuous phase within the outer matrix material. The particle(s) typically have mechanical properties that differ from the mechanical properties of the outer matrix material. Preferably, the particle(s) have a higher mechanical strength than the outer matrix material. The particle(s) within the preferred tablet according to the invention can be visualized by conventional means such as x-ray, solid state nuclear magnetic resonance spectroscopy, raster electron microscopy, terahertz spectroscopy and the like.

In the preferred tablet according to the invention, the particle(s) are incorporated in an outer matrix material. From a macroscopic perspective, the outer matrix material preferably forms a continuous phase in which the particle(s) are embedded as discontinuous phase.

Preferably, the outer matrix material is a homogenous coherent mass, preferably a homogeneous mixture of solid constituents, in which the particle(s) are embedded thereby spatially separating the particle(s) from one another. While it is possible that the surfaces of particle(s) are in contact or at least in very close proximity with one another, the plurality of particle(s) preferably cannot be regarded as a single continuous coherent mass within the preferred tablet according to the invention.

In other words, the preferred tablet according to the invention comprises the particle(s) as volume element(s) of a first type in which the pharmacologically active ingredient a and the polymer matrix, which preferably comprises polyalkylene oxide, are contained, preferably homogeneously, and the outer matrix material as volume element of a second type differing from the material that forms the particle(s), preferably containing neither pharmacologically active ingredient a/b nor polymer matrix, polyalkylene oxide, but optionally polyethylene glycol which differs from polyethylene oxide in its molecular weight.

When portion $b_P$ of the pharmacologically active ingredient is present in form of a powder, said powder is a constituent of the outer matrix material of the preferred tablet according to the invention. When portion $b_G$ of the pharmacologically active ingredient is present in form of granules, said granules are a constituent of the outer matrix material of the preferred tablet according to the invention.

A purpose of the outer matrix material in the preferred tablet according to the invention is to ensure rapid disintegration and subsequent release of the pharmacologically active ingredients a and b from the disintegrated preferred tablet according to the invention, i.e. from the particle(s) A and optionally from particle(s) B, from the coating of particle(s) A, from the granules and from the powder, respectively. Thus, the outer matrix material preferably does not contain any excipient that might have a retardant effect on disintegration and drug release, respectively. Thus, the outer matrix material preferably does not contain any polymer that is typically employed as outer matrix material in prolonged release formulations.

The preferred tablet according to the invention preferably comprises the outer matrix material in an amount of more than one third of the total weight of the preferred tablet according to the invention. Thus, the polymer matrix which preferably comprises polyalkylene oxide and which is contained in the particle(s) A of the preferred tablet according to the invention is preferably not also contained in the outer matrix material.

Preferably, the pharmacologically active ingredient a which is contained in the particle(s) A of the preferred tablet according to the invention is preferably not also contained in the outer matrix material. Thus, in a preferred embodiment, the total amount of pharmacologically active ingredient a contained in the preferred tablet according to the invention is present in the particle(s) A which form a discontinuous phase within the outer matrix material; and the outer matrix material forming a continuous phase does not contain any pharmacologically active ingredient a.

Preferably, the optionally present pharmacologically active ingredient b, at least a portion of which is preferably present as a powder and/or in form of granules, is contained in the outer matrix material, whereas compaction of the preferred tablet according to the invention has typically caused compaction of said powder and/or granules, typically in admixture with the other constituents of the outer matrix material.

Preferably, the content of the outer matrix material is at least 35 wt.-%, at least 37.5 wt.-% or at least 40 wt.-%; more preferably at least 42.5 wt.-%, at least 45 wt.-%, at least 47.5 wt.-% or at least 50 wt.-%; still more preferably at least 52.5 wt.-%, at least 55 wt.-%, at least 57.5 wt.-% or at least 60 wt.-%; yet more preferably at least 62.5 wt.-%, at least 65 wt.-%, at least 67.5 wt.-% or at least 60 wt.-%; most preferably at least 72.5 wt.-%, at least 75 wt.-%, at least 77.5 wt.-% or at least 70 wt.-%; and in particular at least 82.5 wt.-%, at least 85 wt.-%, at least 87.5 wt.-% or at least 90 wt.-%; based on the total weight of the preferred tablet according to the invention.

Preferably, the content of the outer matrix material is at most 90 wt.-%, at most 87.5 wt.-%, at most 85 wt.-%, or at most 82.5 wt.-%; more preferably at most 80 wt.-%, at most 77.5 wt.-%, at most 75 wt.-% or at most 72.5 wt.-%; still more preferably at most 70 wt.-%, at most 67.5 wt.-%, at most 65 wt.-% or at most 62.5 wt.-%; yet more preferably at most 60 wt.-%, at most 57.5 wt.-%, at most 55 wt.-% or at most 52.5 wt.-%; most preferably at most 50 wt.-%, at most 47.5 wt.-%, at most 45 wt.-% or at most 42.5 wt.-%; and in particular at most 40 wt.-%, at most 37.5 wt.-%, or at most 35 wt.-%; based on the total weight of the preferred tablet according to the invention.

In a preferred embodiment, the content of the outer matrix material is within the range of 40±5 wt.-%, more preferably 40±2.5 wt.-%, based on the total weight of the preferred tablet according to the invention. In another preferred embodiment, the content of the outer matrix material is within the range of 45±10 wt.-%, more preferably 45±7.5 wt.-%, still more preferably 45±5 wt.-%, and most preferably 45±2.5 wt.-%, based on the total weight of the preferred tablet according to the invention. In still another preferred embodiment, the content of the outer matrix material is within the range of 50±10 wt.-%, more preferably 50±7.5 wt.-%, still more preferably 50±5 wt.-%, and most preferably 50±2.5 wt.-%, based on the total weight of the preferred tablet according to the invention. In yet another preferred embodiment, the content of the outer matrix material is within the range of 55±10 wt.-%, more preferably 55±7.5 wt.-%, still more preferably 55±5 wt.-%, and most preferably 55±2.5 wt.-%, based on the total weight of the preferred tablet according to the invention.

Preferably, the outer matrix material is a mixture, preferably a homogeneous mixture of at least two different constituents, more preferably of at least three different constituents. In a preferred embodiment, all constituents of the outer matrix material are homogeneously distributed in the continuous phase that is formed by the outer matrix material.

Preferably, the outer matrix material is a homogenous powdery or coherent mass, preferably a homogeneous mixture of solid constituents, in which the particle(s) A are embedded. According to this embodiment, the particle(s) A are preferably spatially separated from one another. While it is possible that the surfaces of particle(s) A are in contact or at least in very close proximity with one another, the plurality of particle(s) A preferably cannot be regarded as a single continuous coherent mass within the dosage form.

The dosage form according to the invention may contain additional pharmaceutical excipients conventionally contained in dosage forms in conventional amounts, such as fillers, binders, dispersing agents, wetting agents, disintegrants, gelling agents, antioxidants, preservatives, lubricants, plasticizer, fillers, binders, and the like.

Said excipients may independently of one another be present in the particle(s) A, the matrix material of the preferred tablet according to the invention, the optionally present particle(s) B, the optionally present coating of particle(s) A, and the optionally present granules, respectively.

The skilled person will readily be able to determine appropriate excipients as well as the quantities of each of these excipients. Specific examples of pharmaceutically acceptable carriers and excipients that may be used to formulate the dosage forms according to the invention are described in the Handbook of Pharmaceutical Excipients, American Pharmaceutical Association (1986).

Preferably, the particle(s), the coating, the outer matrix material, the capsule filling, and/or the granules independently comprise one or more fillers or binders. As many fillers can be regarded as binders and vice versa, for the purpose of the specification "filler/binder" refers to any excipient that is suitable as filler, binder or both. Thus, the particle(s), the coating, the outer matrix material, the capsule filling, and/or the granules independently preferably comprise a filler/binder.

Preferred fillers (=filler/binders) are selected from the group consisting of silicium dioxide (e.g. Aerosil®), microcrystalline cellulose (e.g. Avicel®, Elcema®, Emocel®, ExCel®, Vitacell®); cellulose ether (e.g. Natrosol®, Klucel®, Methocel®, Blanose®, Pharmacoat®, Viscontran®); mannitol; dextrines; dextrose; calciumhydrogen phosphate (e.g. Emcompress®); tricalcium phosphate, maltodextrine (e.g. Emdex®); lactose (e.g. Fast-Flow Lactose®; Ludipress®, Dosage Formtose®, Zeparox®); polyvinylpyrrolidone (PVP) (e.g. Kollidone®, Polyplasdone®, Polydone®); saccharose (e.g. Nu-Tab®, Sugar Tab®); magnesium salts (e.g. $MgCO_3$, MgO, $MgSiO_3$); starches and pretreated starches (e.g. Prejel®, Primotab® ET, Starch® 1500). Preferred binders are selected from the group consisting of alginates; chitosanes; and any of the fillers mentioned above (=fillers/binders).

Some fillers/binders may also serve other purposes. It is known, for example, that silicium dioxide exhibits excellent function as a glidant. Preferably, the particle(s), the coating, the outer matrix material, the capsule filling, and/or the granules independently comprise a glidant such as silicium dioxide.

In a preferred embodiment, the content of the filler/binder or mixture of fillers/binders in the particle(s), the coating, the outer matrix material, the capsule filling, and/or the granules independently is within the range of 50±25 wt.-%, more preferably 50±20 wt.-%, still more preferably 50±15 wt.-%, yet more preferably 50±10 wt.-%, most preferably 50±7.5 wt.-%, and in particular 50±5 wt.-%, based on the total weight of the particle(s), the coating, the outer matrix material, the capsule filling, and/or the granules, respectively. In another preferred embodiment, the content of the filler/binder or mixture of fillers/binders in the particle(s), the coating, the outer matrix material, the capsule filling, and/or the granules independently is within the range of 65±25 wt.-%, more preferably 65±20 wt.-%, still more preferably 65±15 wt.-%, yet more preferably 65±10 wt.-%, most preferably 65±7.5 wt.-%, and in particular 65±5 wt.-%, based on the total weight of the particle(s), the coating, the outer matrix material, the capsule filling, and/or the granules, respectively. In still another preferred embodiment, the content of the filler/binder or mixture of fillers/binders in the particle(s), the coating, the outer matrix material, the capsule filling, and/or the granules independently is within the range of 80±19 wt.-%, more preferably 80±17.5 wt.-%, still more preferably 80±15 wt.-%, yet more preferably 80±10 wt.-%, most preferably 80±7.5 wt.-%, and in particular 80±5 wt.-%, based on the total weight of the particle(s), the coating, the outer matrix material, the capsule filling, and/or the granules, respectively. In another preferred embodiment, the content of the filler/binder or mixture of fillers/binders in the particle(s), the coating, the outer matrix material, the capsule filling, and/or the granules independently is within the range of 90±9 wt.-%, more preferably 90±8 wt.-%, still more preferably 90±7 wt.-%, yet more preferably 90±6 wt.-%, most preferably 90±5 wt.-%, and in particular 90±4 wt.-%, based on the total weight of the particle(s), the coating, the outer matrix material, the capsule filling, and/or the granules, respectively.

In a preferred embodiment, the total content of the filler/binder or mixture of fillers/binders in the dosage form is within the range of 25±24 wt.-%, more preferably 25±20 wt.-%, still more preferably 25±16 wt.-%, yet more preferably 25±12 wt.-%, most preferably 25±8 wt.-%, and in particular 25±4 wt.-%, based on the total weight of dosage form. In another preferred embodiment, the total content of the filler/binder or mixture of fillers/binders in the dosage form is within the range of 30±29 wt.-%, more preferably 30±25 wt.-%, still more preferably 30±20 wt.-%, yet more preferably 30±15 wt.-%, most preferably 30±10 wt.-%, and in particular 30±5 wt.-%, based on the total weight of dosage form. In still another preferred embodiment, the total content of the filler/binder or mixture of fillers/binders in the dosage form is within the range of 35±34 wt.-%, more preferably 35±28 wt.-%, still more preferably 35±22 wt.-%, yet more preferably 35±16 wt.-%, most preferably 35±10 wt.-%, and in particular 35±4 wt.-%, based on the total weight of dosage form. In another preferred embodiment, the total content of the filler/binder or mixture of fillers/binders in the dosage form is within the range of 40±39 wt.-%, more preferably 40±32 wt.-%, still more preferably 40±25 wt.-%, yet more preferably 40±18 wt.-%, most preferably 40±11 wt.-%, and in particular 40±4 wt.-%, based on the total weight of dosage form.

In a preferred embodiment, particularly when the dosage form is a capsule, the capsule is preferably filled with particle(s) A, which are optionally coated comprising portion $b_C$ of the optionally present pharmacologically active ingredient b, and/or with the outer matrix material and/or with portion $b_P$ of the optionally present pharmacologically active ingredient b in form of a powder, and/or with optionally present particle(s) B, and/or with the optionally present granules comprising portion $b_G$ of the optionally present pharmacologically active ingredient b; and additionally with a filler/binder, preferably lactose or mannitol.

In a preferred embodiment, the total content of the filler/binder is preferably within the range of 25±20 wt.-%, more preferably 25±15 wt.-%, still more preferably 25±10 wt.-%, and most preferably 25±5 wt.-%, based on the total weight of the dosage form. In another preferred embodiment, the total content of the filler/binder is preferably within the range of 35±30 wt.-%, more preferably 35±25 wt.-%, still more preferably 35±20 wt.-%, yet more preferably 35±15 wt.-%, even more preferably 35±10 wt.-%, and most preferably 35±5 wt.-%, based on the total weight of the dosage form. In still another preferred embodiment, the total content of the filler/binder is preferably within the range of 45±40 wt.-%, more preferably 45±35 wt.-%, still more preferably 45±30 wt.-%, yet more preferably 45±25 wt.-%, even more preferably 45±20 wt.-%, and most preferably 45±15 wt.-%, and in particular 45±10 wt.-%, based on the total weight of the dosage form. In yet another preferred embodiment, the total content of the filler/binder is preferably within the range of 55±40 wt.-%, more preferably 55±35 wt.-%, still more preferably 55±30 wt.-%, yet more preferably 55±25 wt.-%, even more preferably 55±20 wt.-%, and most preferably 55±15 wt.-%, and in particular 55±10 wt.-%, based on the total weight of the dosage form. In another preferred embodiment, the total content of the filler/binder is preferably within the range of 65±30 wt.-%, more preferably 65±25 wt.-%, still more preferably 65±20 wt.-%, yet more preferably 65±15 wt.-%, even more preferably 65±10 wt.-%, and most preferably 65±5 wt.-%, based on the total weight of the dosage form.

It has been surprisingly found that the filler/binder in the capsule filling can accelerate in vitro release of the pharmacologically active ingredient a and/or of the optionally present pharmacologically active ingredient b from the dosage form according to the invention.

Preferably, the filler/binder is contained in the optionally present particle(s) B but not in the particle(s) A of the dosage form according to the invention.

Preferably, the particle(s), the coating, the outer matrix material, the capsule filling, and/or the granules independently comprise a disintegrant, wherein the content of the disintegrant is more than 5.0 wt.-%, based on the total weight of the dosage form and/or based on the total weight of the particle(s), the coating, the outer matrix material, the capsule filling, and/or the granules, respectively.

In a preferred embodiment, particularly when the dosage form is a capsule, the dosage form contains the entire amount of disintegrant within the particle(s), i.e. outside the particle(s) there is preferably no disintegrant. Furthermore, the disintegrant is preferably homogeneously distributed in the particle(s). Preferably, when the particle(s) are coated, the coating does not contain disintegrant.

In another preferred embodiment, particularly when the dosage form is a tablet, the dosage form contains the disintegrant within the particle(s) as well as outside the particle(s). In a preferred embodiment, the nature of disintegrant within the particle(s) is identical with the nature of disintegrant outside the particle(s). However, different disintegrants inside the particle(s) and outside the particle(s) are also possible in accordance with the invention. Furthermore, the disintegrant is preferably homogeneously distributed in the particle(s). Preferably, when the particle(s) are coated, the coating does not contain disintegrant.

In still another preferred embodiment, particularly when the dosage form is the preferred tablet according to the invention, the dosage form contains the disintegrant outside the particle(s), and optionally also within the particle.

Suitable disintegrants are known to the skilled person and are preferably selected from the group consisting of starches, starch derivatives, cellulose derivatives and gas releasing substances. Croscarmellose ist particularly preferred as disintegrant.

Preferred starches include but are not limited to "standard starch" (e.g. native maize starch) and pregelatinized starch (e.g. starch 1500).

Preferred starch derivatives include but are not limited to sodium starch glycolate (e.g. Vivastar®).

Preferred cellulose derivatives include but are not limited to croscarmellose sodium (=crosslinked sodium carboxymethylcellulose; e.g. Vivasol®).

Preferred gas releasing substances include but are not limited to sodium bicarbonate.

Preferred disintegrants include but are not limited to crosslinked sodium carboxymethylcellulose (Na-CMC) (e.g. Crosscarmellose, Vivasol®, Ac-Di-Sol®); crosslinked casein (e.g. Esma-Spreng®); polysaccharide mixtures obtained from soybeans (e.g. Emcosoy®); maize starch or pretreated maize starch (e.g. Amijel®); sodium alginate; polyvinylpyrrolidone (PVP) (e.g. Kollidone®, Polyplasdone®, Polydone®); crosslinked polyvinylpyrrolidone (PVP CI) (e.g. Polyplasdone® XL); starch and pretreated starch such as sodium carboxymethyl starch (=sodium starch glycolate, e.g. Explotab®, Prejel®, Primotab® ET, Starch® 1500, Ulmatryl®), and the mixtures thereof. Crosslinked polymers are particularly preferred disintegrants, especially crosslinked sodium carboxymethylcellulose (Na-CMC) or crosslinked polyvinylpyrrolidone (PVP CI).

Preferably, the content of the disintegrant is at least 6.0 wt.-%, at least 7.0 wt.-%, at least 8.0 wt.-%, at least 9.0 wt.-%, or at least 10 wt.-%, more preferably at least 12 wt.-%, still more preferably at least 14 wt.-%, yet more preferably at least 15 wt.-%, even more preferably at least 16 wt.-%, most preferably at least 18 wt.-%, and in particular at least 19 wt.-%, based on the total weight of the dosage form and/or based on the total weight of the particle(s), the coating, the outer matrix material, the capsule filling, and/or the granules, respectively.

In a preferred embodiment, the content of the disintegrant is within the range of 15±9.0 wt.-%, more preferably 15±8.5 wt.-%, still more preferably 15±8.0 wt.-%, yet more preferably 15±7.5 wt.-%, most preferably 15±7.0 wt.-%, and in particular 15±6.5 wt.-%, based on the total weight of the dosage form and/or based on the total weight of the particle(s), the coating, the outer matrix material, the capsule filling, and/or the granules, respectively. In still another preferred embodiment, the content of the disintegrant is within the range of 15±6.0 wt.-%, more preferably 15±5.5 wt.-%, still more preferably 15±5.0 wt.-%, yet more preferably 15±4.5 wt.-%, most preferably 15±4.0 wt.-%, and in particular 15±3.5 wt.-%, based on the total weight of the dosage form and/or based on the total weight of the particle(s), the coating, the outer matrix material, the capsule filling, and/or the granules, respectively. In another preferred embodiment, the content of the disintegrant is within the range of 15±3.0 wt.-%, more preferably 15±2.5 wt.-%, still more preferably 15±2.0 wt.-%, yet more preferably 15±1.5 wt.-%, most preferably 15±1.0 wt.-%, and in particular 15±0.5 wt.-%, based on the total weight of the dosage form and/or based on the total weight of the particle(s), the coating, the outer matrix material, the capsule filling, and/or the granules, respectively.

In another preferred embodiment, the content of the disintegrant is within the range of 20±15 wt.-% or 20±14 wt.-%, more preferably 20±13 wt.-%, still more preferably 20±12 wt.-%, yet more preferably 20±11 wt.-%, most preferably 20±10 wt.-%, and in particular 20±9.5 wt.-%, based on the total weight of the dosage form and/or based on the total weight of the particle(s), the coating, the outer matrix material, the capsule filling, and/or the granules, respectively. In another preferred embodiment, the content of the disintegrant is within the range of 20±9.0 wt.-%, more preferably 20±8.5 wt.-%, still more preferably 20±8.0 wt.-%, yet more preferably 20±7.5 wt.-%, most preferably 20±7.0 wt.-%, and in particular 20±6.5 wt.-%, based on the total weight of the dosage form and/or based on the total weight of the particle(s), the coating, the outer matrix material, the capsule filling, and/or the granules, respectively. In still another preferred embodiment, the content of the disintegrant is within the range of 20±6.0 wt.-%, more preferably 20±5.5 wt.-%, still more preferably 20±5.0 wt.-%, yet more preferably 20±4.5 wt.-%, most preferably 20±4.0 wt.-%, and in particular 20±3.5 wt.-%, based on the total weight of the dosage form and/or based on the total weight of the particle(s), the coating, the outer matrix material, the capsule filling, and/or the granules, respectively. In another preferred embodiment, the content of the disintegrant is within the range of 20±3.0 wt.-%, more preferably 20±2.5 wt.-%, still more preferably 20±2.0 wt.-%, yet more preferably 20±1.5 wt.-%, most preferably 20±1.0 wt.-%, and in particular 20±0.5 wt.-%, based on the total weight of the dosage form and/or based on the total weight of the particle(s), the coating, the outer matrix material, the capsule filling, and/or the granules, respectively.

In still another preferred embodiment, the content of the disintegrant is within the range of 25±9.0 wt.-%, more preferably 25±8.5 wt.-%, still more preferably 25±8.0 wt.-%, yet more preferably 25±7.5 wt.-%, most preferably 25±7.0 wt.-%, and in particular 25±6.5 wt.-%, based on the total weight of the dosage form and/or based on the total weight of the particle(s), the coating, the outer matrix material, the capsule filling, and/or the granules, respectively. In still another preferred embodiment, the content of the disintegrant is within the range of 25±6.0 wt.-%, more preferably 25±5.5 wt.-%, still more preferably 25±5.0 wt.-%, yet more preferably 25±4.5 wt.-%, most preferably 25±4.0 wt.-%, and in particular 25±3.5 wt.-%, based on the total weight of the dosage form and/or based on the total weight of the particle(s), the coating, the outer matrix material, the capsule filling, and/or the granules, respectively. In another preferred embodiment, the content of the disintegrant is within the range of 25±3.0 wt.-%, more preferably 25±2.5 wt.-%, still more preferably 25±2.0 wt.-%, yet more preferably 25±1.5 wt.-%, most preferably 25±1.0 wt.-%, and in particular 25±0.5 wt.-%, based on the total weight of the dosage form and/or based on the total weight of the particle(s), the coating, the outer matrix material, the capsule filling, and/or the granules respectively.

When the dosage form according to the invention contains more than a single disintegrant, e.g. a mixture of two different disintegrants, the above percentages preferably refer to the total content of disintegrants.

Preferably, the relative weight ratio of the polyalkylene oxide to the disintegrant is within the range of 8:1 to 1:5, more preferably 7:1 to 1:4, still more preferably 6:1 to 1:3, yet more preferably 5:1 to 1:2, most preferably 4:1 to 1:1, and in particular 3:1 to 2:1.

Preferably, the relative weight ratio of the pharmacologically active ingredient a to the disintegrant is within the range of 4:1 to 1:10, more preferably 3:1 to 1:9, still more preferably 2:1 to 1:8, yet more preferably 1:1 to 1:7, most preferably 1:2 to 1:6, and in particular 1:3 to 1:5.

The dosage form may contain a single disintegrant or a mixture of different disintegrants. Preferably, the dosage form contains a single disintegrant.

Preferably, the dosage form according to the invention and/or the particle(s), the coating, the outer matrix material, the capsule filling, and/or the granules independently further comprise an antioxidant. Suitable antioxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfate, particularly preferably butylhydroxytoluene or butylhydroxyanisole and α-tocopherol. The antioxidant is preferably present in quantities of 0.01 wt.-% to 10 wt.-%, more preferably of 0.03 wt.-% to 5 wt.-%, most preferably of 0.05 wt.-% to 2.5 wt.-%, based on the total weight of the dosage form and/or based on the total weight of the particle(s), the coating, the outer matrix material, the capsule filling, and/or the granules, respectively.

In a preferred embodiment, the dosage form according to the invention and/or the particle(s), the coating, the outer matrix material, the capsule filling, and/or the granules independently further comprise an acid, preferably citric acid. The amount of acid is preferably in the range of 0.01 wt.-% to 20 wt.-%, more preferably in the range of 0.02 wt.-% to 10 wt.-%, and still more preferably in the range of 0.05 wt.-% to 5 wt.-%, and most preferably in the range of 0.1 wt.-% to 1.0 wt.-%, based on the total weight of the dosage form and/or based on the total weight of the particle(s), the coating, the outer matrix material, the capsule filling, and/or the granules, respectively.

In a preferred embodiment, the dosage form according to the invention and/or the particle(s), the coating, the outer matrix material, the capsule filling, and/or the granules independently further comprise another polymer which is preferably selected from cellulose esters and cellulose ethers, in particular hydroxypropyl methylcellulose (HPMC).

The amount of the further polymer, preferably hydroxypropyl methylcellulose, preferably ranges from 0.1 wt.-% to 30 wt.-%, more preferably in the range of 1.0 wt.-% to 20 wt.-%, most preferably in the range of 2.0 wt.-% to 15 wt.-%, and in particular in the range of 3.5 wt.-% to 10.5 wt.-%, based on the total weight of the dosage form and/or based on the total weight of the particle(s), the coating, the outer matrix material, the capsule filling, and/or the granules, respectively.

When the polymer matrix of the particle(s) comprises polyalkylene oxide, in a preferred embodiment, the relative weight ratio of the polyalkylene oxide to the further polymer is within the range of 4.5±2:1, more preferably 4.5±1.5:1, still more preferably 4.5±1:1, yet more preferably 4.5±0.5:1, most preferably 4.5±0.2:1, and in particular 4.5±0.1:1. In another preferred embodiment, the relative weight ratio of the polyalkylene oxide to the further polymer is within the range of 8±7:1, more preferably 8±6:1, still more preferably 8±5:1, yet more preferably 8±4:1, most preferably 8±3:1, and in particular 8±2:1. In still another preferred embodiment, the relative weight ratio of the polyalkylene oxide to the further polymer is within the range of 11±8:1, more preferably 11±7:1, still more preferably 11±6:1, yet more preferably 11±5:1, most preferably 11±4:1, and in particular 11±3:1.

In another preferred embodiment, the dosage form and/or the particle(s) according to the invention do not contain any further polymer besides the polyalkylene oxide and optionally, polyethylene glycol.

In a preferred embodiment, the dosage form according to the invention contains at least one lubricant. Preferably, the lubricant is contained in the dosage form outside the particle(s), i.e. the particle(s) as such preferably do not contain lubricant. The lubricant can be independently contained in the coating, the outer matrix material, and/or the granules.

Especially preferred lubricants are selected from magnesium stearate and stearic acid;

glycerides of fatty acids, including monoglycerides, diglycerides, triglycerides, and mixtures thereof; preferably of $C_6$ to $C_{22}$ fatty acids; especially preferred are partial glycerides of the $C_{16}$ to $C_{22}$ fatty acids such as glycerol behenat, glycerol palmitostearate and glycerol monostearate;

polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;

polyglycolyzed glycerides, such as the one known and commercially available under the trade name "Labrasol";

fatty alcohols that may be linear or branched, such as cetylalcohol, stearylalcohol, cetylstearyl alcohol, 2-octyldodecane-1-ol and 2-hexyldecane-1-ol;

polyethylene glycols having a molecular weight between 10.000 and 60.000 g/mol; and natural semi-synthetic or synthetic waxes, preferably waxes with a softening point of at least 50° C., more preferably 60° C., and in particular carnauba wax and bees wax.

Preferably, the amount of the lubricant ranges from 0.01 wt.-% to 10 wt.-%, more preferably in the range of 0.05 wt.-% to 7.5 wt.-%, most preferably in the range of 0.1 wt.-% to 5 wt.-%, and in particular in the range of 0.1 wt.-% to 1 wt.-%, based on the total weight of the dosage form and/or based on the total weight of the particle(s), the coating, the outer matrix material, the capsule filling, and/or the granules, respectively.

In another preferred embodiment, the dosage form contains no lubricant.

Preferably, the dosage form according to the invention and/or the particle(s), the coating, the outer matrix material, the capsule filling, and/or the granules independently further comprise a plasticizer. The plasticizer improves the processability of the polymer matrix that preferably comprises polyalkylene oxide. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000 (Macrogol 6000).

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 6 to 20 wt.-% and in particular 7 wt.-% to 17.5 wt.-%, based on the total weight of the dosage form and/or based on the total weight of the particle(s), the coating, the outer matrix material, the capsule filling, and/or the granules, respectively.

In a preferred embodiment, the plasticizer is a polyalkylene glycol having a content within the range of 7±6 wt.-%, more preferably 7±5 wt.-%, still more preferably 7±4 wt.-%, yet more preferably 7±3 wt.-%, most preferably 7±2 wt.-%, and in particular 7±1 wt.-%, based on the total weight of the dosage form and/or based on the total weight of the particle(s), the coating, the outer matrix material, the capsule filling, and/or the granules, respectively. In another preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the dosage form and/or based on the total weight of the particle(s), the coating, the outer matrix material, the capsule filling, and/or the granules, respectively.

In a preferred embodiment, the relative weight ratio of the polyalkylene oxide to the polyalkylene glycol is within the range of 5.4±2:1, more preferably 5.4±1.5:1, still more preferably 5.4±1:1, yet more preferably 5.4±0.5:1, most preferably 5.4±0.2:1, and in particular 5.4±0.1:1. This ratio satisfies the requirements of relative high polyalkylene oxide content and good extrudability.

Plasticizers can sometimes act as a lubricant, and lubricants can sometimes act as a plasticizer.

In preferred compositions of the particle(s) A that are preferably hot-melt extruded and that are contained in the dosage form according to the invention, the polymer matrix comprises a polyalkylene oxide, preferably a polyethylene oxide with a weight average molecular weight within the range of from 0.5 to 15 million g/mol.

The particle(s) A comprise pharmacologically active ingredient a. Particularly preferred embodiments $C^1$ to $C^{12}$ are summarized in the tables here below:

| per particle A [wt.-%] | $C^1$ | $C^2$ | $C^3$ | $C^4$ |
| --- | --- | --- | --- | --- |
| pharmacologically active ingredient a | 5.50 ± 5.00 | 5.50 ± 4.00 | 5.50 ± 3.00 | 5.50 ± 2.00 |
| polyalkylene oxide | 60.00 ± 35.00 | 60.00 ± 30.00 | 60.00 ± 25.00 | 60.00 ± 15.00 |
| optionally acid, e.g. citric acid | 0.80 ± 0.75 | 0.80 ± 0.65 | 0.80 ± 0.50 | 0.80 ± 0.35 |
| optionally plasticizer, e.g. polyethylene glycol | 14.00 ± 13.50 | 14.00 ± 10.00 | 14.00 ± 7.50 | 14.00 ± 5.00 |
| optionally antioxidant, e.g. α-tocopherol | 0.20 ± 0.18 | 0.20 ± 0.14 | 0.20 ± 0.10 | 0.20 ± 0.06 |

| per particle A [wt.-%] | $C^5$ | $C^6$ | $C^7$ | $C^8$ |
| --- | --- | --- | --- | --- |
| pharmacologically active ingredient a | 15.00 ± 25.00 | 15.00 ± 20.00 | 15.00 ± 15.00 | 15.00 ± 10.00 |
| polyalkylene oxide | 60.00 ± 35.00 | 60.00 ± 30.00 | 60.00 ± 25.00 | 60.00 ± 15.00 |
| optionally acid, e.g. citric acid | 0.80 ± 0.75 | 0.80 ± 0.65 | 0.80 ± 0.50 | 0.80 ± 0.35 |
| optionally plasticizer, e.g. polyethylene glycol | 11.00 ± 8.00 | 11.00 ± 6.00 | 11.00 ± 5.00 | 11.00 ± 4.00 |
| optionally antioxidant, e.g. α-tocopherol | 0.20 ± 0.18 | 0.20 ± 0.14 | 0.20 ± 0.10 | 0.20 ± 0.06 |

-continued

| per particle A [wt.-%] | C⁹ | C¹⁰ | C¹¹ | C¹² |
|---|---|---|---|---|
| pharmacologically active ingredient a | 30.00 ± 25.00 | 30.00 ± 20.00 | 30.00 ± 15.00 | 30.00 ± 10.00 |
| polyalkylene oxide | 60.00 ± 35.00 | 60.00 ± 30.00 | 60.00 ± 25.00 | 60.00 ± 15.00 |
| optionally acid, e.g. citric acid | 0.80 ± 0.75 | 0.80 ± 0.65 | 0.80 ± 0.50 | 0.80 ± 0.35 |
| optionally plasticizer, e.g. polyethylene glycol | 9.00 ± 8.00 | 9.00 ± 6.00 | 9.00 ± 5.00 | 9.00 ± 4.00 |
| optionally antioxidant, e.g. α-tocopherol | 0.20 ± 0.18 | 0.20 ± 0.14 | 0.20 ± 0.10 | 0.20 ± 0.06 |

(all percentages relative to the total weight of the particle(s) A).

In a preferred embodiment of the dosage form according to the invention, the particle(s) A and/or the optionally present particle(s) B are hot melt-extruded. Thus, the particle(s) according to the invention are preferably prepared by melt-extrusion, although also other methods of thermoforming may be used in order to manufacture the particle(s) according to the invention such as press-molding at elevated temperature or heating of particle(s) that were manufactured by conventional compression in a first step and then heated above the softening temperature of the polyalkylene oxide in the particle(s) in a second step to form hard dosage forms. In this regards, thermoforming means the forming, or molding of a mass after the application of heat. In a preferred embodiment, the particle(s) are thermoformed by hot-melt extrusion.

In a preferred embodiment, the particle(s) are prepared by hot melt-extrusion, preferably by means of a twin-screw-extruder. Melt extrusion preferably provides a melt-extruded strand that is preferably cut into monoliths, which are then optionally compressed and formed into particle(s). Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air, at elevated temperature, e.g. when the extruded stand is still warm due to hot-melt extrusion, or at ambient temperature, i.e. after the extruded strand has been allowed to cool down. When the extruded strand is still warm, singulation of the extruded strand into extruded particle(s) is preferably performed by cutting the extruded strand immediately after it has exited the extrusion die. It is possible to subject the extruded strands to the compression step or to the cutting step when still warm, that is more or less immediately after the extrusion step. The extrusion is preferably carried out by means of a twin-screw extruder.

The particle(s) of the dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

In general, the process for the production of the particle(s) according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide up to its softening point;
(c) hardening the mixture by applying heat and force, it being possible to supply the heat during and/or before and/or after the application of force and the quantity of heat supplied being sufficient to heat the polyalkylene oxide at least up to its softening point; and thereafter allowing the material to cool and removing the force
(d) optionally singulating the hardened mixture; and
(e) optionally providing a film coating.

In a preferred embodiment, the mixture is compressed and subsequently heated. In another preferred embodiment, the mixture is heated and subsequently compressed. In still another preferred embodiment, the mixture is heated and compressed simultaneously. A skilled person recognizes that combinations of these embodiments according to the invention are also possible.

Heat may be supplied directly, e.g. by contact or by means of hot gas such as hot air, or with the assistance of ultrasound; or is indirectly supplied by friction and/or shear. Force may be applied and/or the particle(s) may be shaped for example by direct tabletting or with the assistance of a suitable extruder, particularly by means of a screw extruder equipped with one or two screws (single-screw-extruder and twin-screw-extruder, respectively) or by means of a planetary gear extruder.

The final shape of the particle(s) may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide. However, extrusion at lower temperatures, e.g. ambient temperature, is also possible and may be preferred.

A particularly preferred process for the manufacture of the particle(s) according to the invention involves hot-melt extrusion. In this process, the particle(s) according to the invention are produced by thermoforming with the assistance of an extruder, preferably without there being any observable consequent discoloration of the extrudate.

This process is characterized in that
a) all components are mixed,
b) the resultant mixture is heated in the extruder at least up to the softening point of the polyalkylene oxide and extruded through the outlet orifice of the extruder by application of force,
c) the still plastic extrudate is singulated and formed into the particle(s) or
d) the cooled and optionally reheated singulated extrudate is formed into the particle(s).

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of polyalkylene oxide is extruded from the extruder through a die with at least one bore, preferably a multitude of bores.

The process according to the invention requires the use of suitable extruders, preferably screw extruders. Screw extruders which are equipped with two screws (twin-screw-extruders) are particularly preferred.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide proceeding in the first zone, which is downstream from a feed zone and optionally mixing zone. The throughput of the mixture is preferably from 1.0 kg to 15 kg/hour. In a preferred embodiment, the throughput is from 0.5 kg/hour to 3.5 kg/hour. In another preferred embodiment, the throughput is from 4 to 15 kg/hour.

In a preferred embodiment, the die head pressure is within the range of from 25 to 200 bar. The die head pressure can be adjusted inter alia by die geometry, temperature profile, extrusion speed, number of bores in the dies, screw configuration, first feeding steps in the extruder, and the like.

The die geometry or the geometry of the bores is freely selectable. The die or the bores may accordingly exhibit a round, oblong or oval cross-section, wherein the round cross-section preferably has a diameter of 0.1 mm to 2 mm, preferably of 0.5 mm to 0.9 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide and does not rise above a temperature at which the pharmacologically active ingredient a to be processed may be damaged. Preferably, the temperature of the mixture to be extruded is adjusted to below 180° C., preferably below 150° C., but at least to the softening temperature of polyalkylene oxide. Typical extrusion temperatures are 120° C. and 150° C.

In a preferred embodiment, the extruder torque is within the range of from 30 to 95%. Extruder torque can be adjusted inter alia by die geometry, temperature profile, extrusion speed, number of bores in the dies, screw configuration, first feeding steps in the extruder, and the like.

After extrusion of the molten mixture and optional cooling of the extruded strand or extruded strands, the extrudates are preferably singulated. This singulation may preferably be performed by cutting up the extrudates by means of revolving or rotating knives, wires, blades or with the assistance of laser cutters.

Preferably, intermediate or final storage of the optionally singulated extrudate or the final shape of the particle(s) according to the invention is performed under oxygen-free atmosphere which may be achieved, e.g., by means of oxygen-scavengers.

The singulated extrudate may be press-formed into particle(s) in order to impart the final shape to the particle(s).

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a dosage form with desired mechanical properties, may be established by simple preliminary testing.

For example but not limiting, extrusion may be performed by means of a twin-screw-extruder type ZSE 18 or ZSE27 (Leistritz, Nurnberg, Germany), screw diameters of 18 or 27 mm. Screws having eccentric or blunt ends may be used. A heatable die with a round bore or with a multitude of bores each having a diameter of 0.2, 0.3, 0.4, 0.5, 0.6, 0.7, 0.8, 0.9 or 1.0 mm may be used. For a twin-screw-extruder type ZSE 18, the extrusion parameters may be adjusted e.g. to the following values: rotational speed of the screws: 120 Upm; delivery rate 2 kg/h for a ZSE 18 or 5 kg/h, 10 kg/h, or even 20 kg/h and more for a ZSE27; product temperature: in front of die 125° C. and behind die 135° C.; and jacket temperature: 110° C. The throughput can generally be increased by increasing the number of dies at the extruder outlet.

Preferably, extrusion is performed by means of twin-screw-extruders or planetary-gear-extruders, twin-screw extruders (co-rotating or contra-rotating) being particularly preferred.

The particle(s) according to the invention are preferably produced by thermoforming with the assistance of an extruder without any observable consequent discoloration of the extrudates. The particle(s) may be produced e.g. by means of a Micro Pelletizer (Leistritz, Nurnberg, Germany).

The process for the preparation of the particle(s) according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the particle(s) according to the invention can be regarded as "extruded pellets". The term "extruded pellets" has structural implications which are understood by persons skilled in the art. A person skilled in the art knows that pelletized dosage forms can be prepared by a number of techniques, including:

drug layering on nonpareil sugar or microcrystalline cellulose beads,
spray drying,
spray congealing,
rotogranulation,
hot-melt extrusion,
spheronization of low melting materials, or
extrusion-spheronization of a wet mass.

Accordingly, "extruded pellets" can be obtained either by hot-melt extrusion or by extrusion-spheronization.

"Extruded pellets" can be distinguished from other types of pellets, as extruded pellets typically have a different shape. The shape of the extruded pellets is typically more cut-rod-like than perfectly globated round.

"Extruded pellets" can be distinguished from other types of pellets because they are structurally different. For example, drug layering on nonpareils yields multilayered pellets having a core, whereas extrusion typically yields a monolithic mass comprising a homogeneous mixture of all ingredients. Similarly, spray drying and spray congealing typically yield spheres, whereas extrusion typically yields cylindrical extrudates which can be subsequently spheronized.

The structural differences between "extruded pellets" and "agglomerated pellets" are significant because they may affect the release of active substances from the pellets and consequently result in different pharmacological profiles. Therefore, a person skilled in the pharmaceutical formulation art would not consider "extruded pellets" to be equivalent to "agglomerated pellets".

The dosage forms according to the invention may be prepared by any conventional method. Suitable methods and apparatuses are known to the skilled person.

When the dosage form is a capsule, all components may be filled separately or as admixture into the capsules. Said components may include but are not limited to particle(s) A, which may optionally be provided with a coating comprising optionally present pharmacologically active ingredient b or portion $b_C$ thereof, the optionally present particle(s) B, the optionally present powder of optionally present pharmacologically active ingredient b, and the optionally present granules of optionally present pharmacologically active ingredient b, respectively.

When the dosage form is a tablet, the tablet is preferably prepared by compression. Thus, particle(s) are preferably mixed, e.g. blended and/or granulated (e.g. wet granulated), e.g. with matrix material of the preferred table according to the invention, the optionally present powder of optionally present pharmacologically active ingredient b and the optionally present granules of optionally present pharmacologically active ingredient b, respectively, and the resulting mix (e.g. blend or granulate) is then compressed, preferably in moulds, to form dosage forms. It is also envisaged that the particle(s) may be incorporated into a matrix using other processes, such as by melt granulation (e.g. using fatty alcohols and/or water-soluble waxes and/or water-insoluble waxes) or high shear granulation, followed by compression.

When the dosage forms according to the invention are manufactured by means of an eccentric press, the compression force is preferably within the range of from 5 to 30 kN, preferably from 15 to 25 kN. When the dosage forms according to the invention are manufactured by means of a rotating press, the compression force is preferably within the range of from 5 to 40 kN, in certain embodiments >25 kN, in other embodiments 13 kN.

The pharmaceutical dosage form according to the invention preferably comprises no wax ingredients. Wax ingredients include fatty acid esters, glycerol fatty acid esters, fatty glyceride derivatives, waxes, and fatty alcohols such as, for example, glycerol behenate, glycerol palmitostearate, glycerol monostearate, stearoyl macroglycerides. Other waxes more generally include insect and animal waxes, vegetable waxes, mineral waxes, petroleum waxes, and synthetic waxes; particularly examples include beeswax, carnauba wax, condelilla wax, montan wax, ouricury wax, rice-bran wax, jojoba wax, microcrystalline wax, cetyl ester wax, cetyl alcohol, anionic emulsifying wax, nonionic emulsifying wax and paraffin wax.

The pharmaceutical dosage form according to the invention comprises particle(s) A which preferably neither comprise an active pharmaceutical layer comprising a pharmacologically active ingredient nor a layer comprising a pH-sensitive film comprising a pH-sensitive polymer that is insoluble in water at a pH greater than 5 and is soluble in water at a pH below 5.

The particle(s) A and dosage forms according to the invention may be used in medicine, e.g. as an analgesic. The particle(s) A and dosage forms are therefore particularly suitable for the treatment or management of pain. In such dosage forms, the pharmacologically active ingredient a is preferably an analgesic.

A further aspect according to the invention relates to the dosage form as described above for use in the treatment of pain. A further aspect of the invention relates to the use of a pharmacologically active ingredient a and/or of an optionally present pharmacologically active ingredient b for the manufacture of a dosage form according to the invention for the treatment of pain. A further aspect of the invention relates to a method for the treatment of pain comprising the administration, preferably oral administration of a dosage form according to the invention to a subject in need thereof.

A further aspect according to the invention relates to the use of a dosage form according to the invention for avoiding or hindering the abuse of the pharmacologically active ingredient a and optionally also of the optionally present pharmacologically active ingredient b contained therein.

A further aspect according to the invention relates to the use of a dosage form according to the invention for avoiding or hindering the unintentional overdose of the pharmacologically active ingredient a contained therein.

In this regard, the invention also relates to the use of a pharmacologically active ingredient a and/or of an optionally present pharmacologically active ingredient b for the manufacture of the dosage form according to the invention for the prophylaxis and/or the treatment of a disorder, thereby preventing an overdose of the pharmacologically active ingredient a, particularly due to comminution of the dosage form by mechanical action.

Another aspect of the invention relates to the use of a pharmaceutical dosage form according to the invention as described above for the prevention of an overdose of pharmacologically active ingredient a after accidental or intentional simultaneous administration of a plurality of the dosage forms containing an overall supratherapeutic dose of the pharmacologically active ingredient a.

Another aspect of the invention relates to method for the prevention of an overdose of pharmacologically active ingredient a after accidental or intentional simultaneous administration of a plurality of dosage forms containing an overall supratherapeutic dose of the pharmacologically active ingredient a, the method comprising the provision of a pharmaceutical dosage form according to the invention as described above.

The following examples further illustrate the invention but are not to be construed as limiting its scope.

Inventive Example 1 and Comparative Example 1 both relate to a combination comprising 10 mg hydrocodone and 325 mg acetaminophen. Comparative Example 1 is based on a commercial product.

Inventive Example 2 and Comparative Example 2 both relate to a combination comprising 5 mg hydrocodone and acetaminophen. Inventive Example 2 relates to a dose of 325 mg acetaminophen, whereas Comparative Example 2 relates to a dose of 300 mg acetaminophen. This minor difference, however, is not significant for the effect as demonstrated by this comparative experimental setting. Comparative Example 2 is based on a commercial product.

Inventive Example 3 and Comparative Example 3 both relate to a composition containing 10 mg amphetamine as the only pharmacologically active ingredient. Comparative Example 3 is based on a commercial product.

Inventive Example 1

10 mg Hydrocodone+325 mg Acetaminophen

Tablets containing a combination of hydrocodone with acetaminophen were manufactured from
- hot melt extruded pellets comprising hydrocodone (particles A comprising pharmacologically avtive ingredient a);
- granules comprising acetaminophen (pharmacologically avtive ingredient b); and
- powder.

Powder mixtures of the various ingredients for the pellets were manufactured by weighing (10 kg balance), sieving (1.0 mm hand sieve) and blending. The thus obtained powder mixtures were then hot-melt extruded (twin-screw extruder, Leistritz ZSE 18, blunt ends of kneading elements, and extrusion diameter of 8×0.8 mm). The extrusion parameters are summarized in the table here below:

| Extrusion parameter set: | |
|---|---|
| Extrusion temperature [° C.] | 100-135° C. |
| nozzle [° C.] | 135 |
| speed screw [rpm] | 100 |
| die diameter [mm] | 0.8 |

The thus obtained cut extrudates were pelletized (LMP).

The granules comprising acetaminophen were separately prepared by conventional granulation. A powder mixture comprising acetaminophen was prepared and thoroughly blended by means of a rapid mixer/granulator (Diosna® P10-60, chopper switched off) for 5 min at 90 rpm. A granulation solution was prepared from purified water and hypromellose. The solution was stirred for 15 min at 550 rpm and 70° C. The powder mixture was granulated by adding the granulation solution over 1:30 min in the rapid mixer/granulator (Diosna® P10-60, chopper at 500 rpm) for 5 min at 135 rpm.

The pellets were then mixed with the granules and with powder and the thus obtained mixture was subsequently compressed to tablets (Korsch XL400). The tabletting parameters are summarized in the table here below:

| Tablet form: | tableting parameter set: | |
|---|---|---|
| Tablet weight = 708.2 mg | tablet weight [mg] | 708.2 |
| Punch form = oblong 7 × 17 mm WR 4.5 without engraving | breaking strength (tablet) [N] | 86 |

The compositions of the hot-melt extruded pellets, the granules and the powder as well as their relative contents in the overall tablets are summarized in the table here below:

| per tablet [mg] | form | per tablet [mg] | Substance | Amount [%] |
|---|---|---|---|---|
| 180.00 | Pellets | 10.00 | hydrocodone bitartrate | 25.42 |
| | | 1.44 | citric acid | |
| | | 24.70 | polyglycol 6000 | |
| | | 0.36 | α-tocopherole | |
| | | 9.00 | xanthan gum | |
| | | 98.50 | polyethylene oxide 7 mio. | |
| | | 36.00 | croscarmellose sodium | |
| 528.20 | Outer matrix | 325.00 | acetaminiophen | 57.23 |
| | | 30.00 | croscarmellose sodium | |
| | | 45.00 | microcrystalline cellulose, type 101 | |
| | | 5.29 | hypromellose | |
| | | 2.28 | magnesium stearate | 0.32 |
| | | 6.90 | silicondioxide | 0.97 |
| | | 113.73 | microcrystalline cellulose, type 101 | 16.06 |
| 708.20 | | | | 100.00 |

While a dose of 10 mg hydrocodone in combination with a dose of 325 mg acetaminophen is a therapeutic dose, a plurality of such dosage forms contains an overall supratherapeutic dose of hydrocodone and acetaminophen.

In order to simulate the situation after accidental or intentional simultaneous administration of a plurality of the dosage forms according to Inventive Example 1, the in vitro release profiles were measured under modified conditions. The testing conditions were varied, particularly with respect to the overall volume of the release medium (900 mL, 600 mL, and 250 mL). The in vitro release profiles of these dosage forms were measured at 37° C. by means of a paddle apparatus without sinker in 0.1 M HCl (in each case number of replicates n=3). Unless expressly stated otherwise, the paddle speed was adjusted to 25 rpm. The results of the in vitro release measurements are shown in the tables here below.

Condition a) 25 rpm, 900 mL:

Hydrocodone—Pharmacologically Avtive Ingredient a:

| mean | 1 tablet [mg] | 5 tablets [mg] per tablet | all 5 | 10 tablets [mg] per tablet | all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 3.33 | 1.61 | 8.05 | 0.89 | 8.93 | 33.29 | 16.08 | 8.89 |
| 30 min | 4.13 | 1.97 | 9.83 | 1.20 | 12.00 | 41.33 | 19.70 | 12.01 |
| 60 min | 4.87 | 2.43 | 12.17 | 1.46 | 14.63 | 48.69 | 24.35 | 14.64 |

It becomes clear from the above data that the dosage forms according to Inventive Example 1 are useful for avoiding overdose upon multiple dosing. For example, while a single dosage form has released 4.13 mg hydrocodone after 30 minutes, when a multitude of 5 dosage forms is tested thereby simulating 5-fold multiple dosing, one dosage form within the group of 5 dosage form has released only 1.97 mg hydrocodone after 30 minutes. When a multitude of 10 dosage forms is tested thereby simulating 10-fold multiple dosing, one dosage form within the group of 10 dosage forms has even only released 1.20 mg hydrocodone after 30 minutes.

Acetaminophen—Pharmacologically Avtive Ingredient b:

| mean | 1 tablet [mg] | 5 tablets [mg] per tablet | 5 tablets [mg] all 5 | 10 tablets [mg] per tablet | 10 tablets [mg] all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 101.16 | 50.91 | 254.53 | 31.36 | 313.57 | 31.12 | 15.67 | 9.65 |
| 30 min | 123.13 | 60.74 | 303.68 | 51.20 | 511.97 | 37.89 | 18.69 | 15.75 |
| 60 min | 141.62 | 72.39 | 361.97 | 45.53 | 455.27 | 43.58 | 22.28 | 14.01 |

It becomes clear from the above data that the dosage forms according to Inventive Example 1 are useful for avoiding overdose upon multiple dosing of both pharmacologically active ingredients. For example, while a single dosage form has released 123.13 mg acetaminophen after 30 minutes, when a multitude of 5 dosage forms is tested thereby simulating 5-fold multiple dosing, one dosage form within the group of 5 dosage form has released only 60.74 mg acetaminophen after 30 minutes. When a multitude of 10 dosage forms is tested thereby simulating 10-fold multiple dosing, one dosage form within the group of 10 dosage forms has even only released 51.20 mg acetaminophen after 30 minutes.

Thus, as demonstrated by the above data, the advantages of the dosage form according to the invention do not only affect the pharmacologically active ingredient a that is embedded in the polyalkylene oxide in particle(s) A, but also the optionally present pharmacologically active ingredient b that may be present elsewhere in the dosage form.

Figure 3:
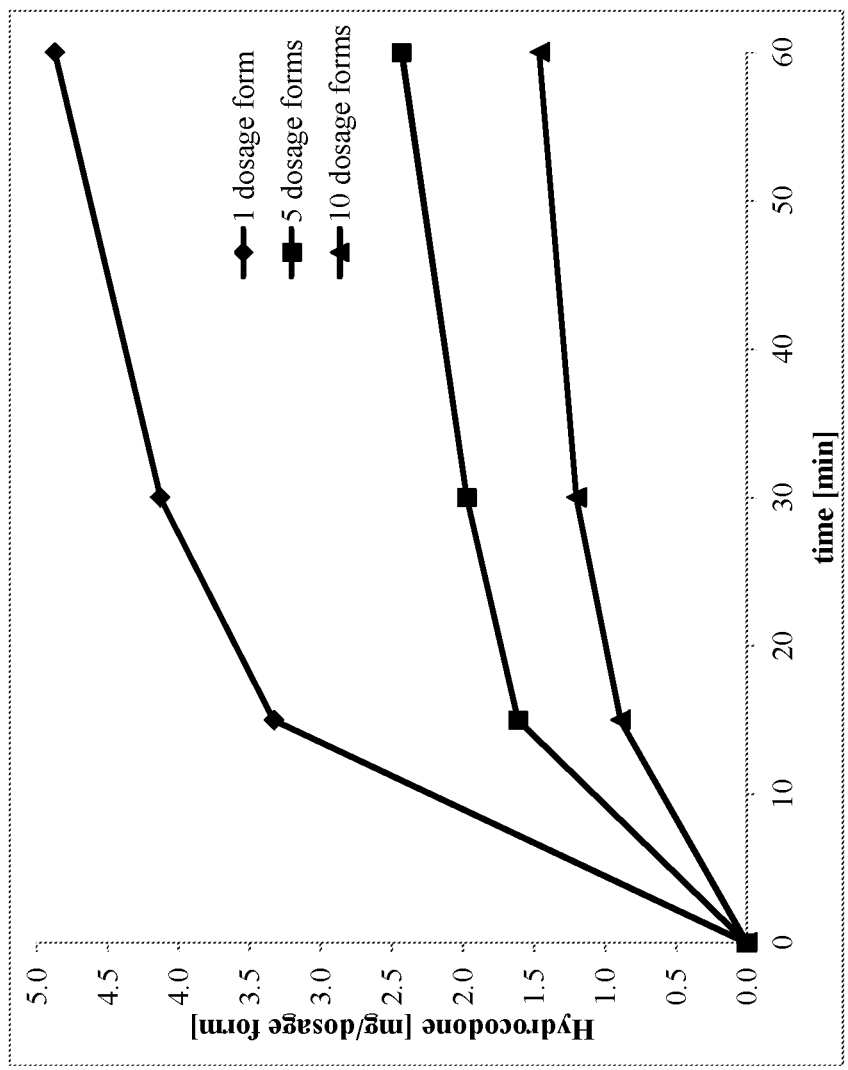
FIGS. 3 and 4 show the release profiles of exemplified dosage according to the invention that comprise two pharmacologically active ingredients, namely hydrocodone and acetaminophen.
Figure 4:
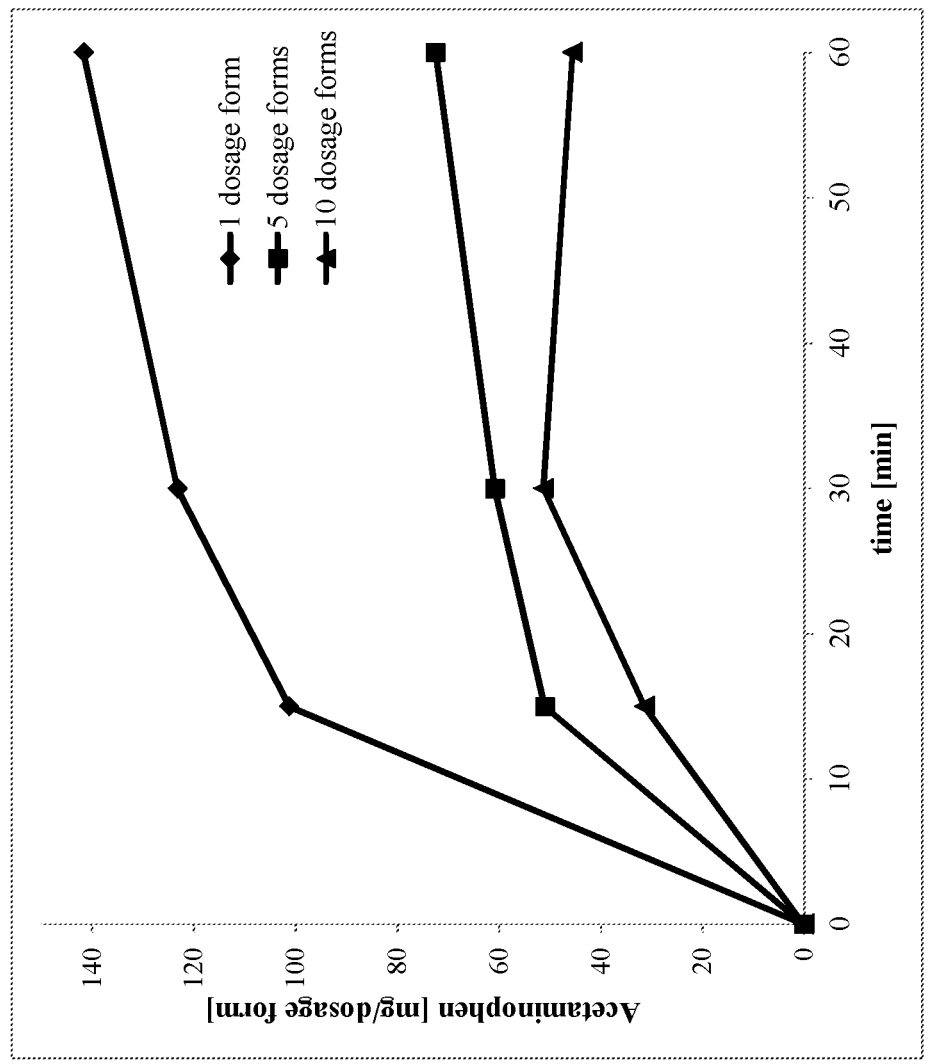

The in vitro release profiles with respect to the release of hydrocodone (pharmacologically active ingredient a) are shown in FIG. 3. The in vitro release profiles with respect to the release of acetaminophen (optionally present pharmacologically active ingredient b) are shown in FIG. 4.

Condition b) 25 rpm, 600 mL:
Hydrocodone—Pharmacologically Avtive Ingredient a:

| mean | 1 tablet [mg] | 5 tablets [mg] per tablet | 5 tablets [mg] all 5 | 10 tablets [mg] per tablet | 10 tablets [mg] all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 3.80 | 1.57 | 7.85 | 0.98 | 9.80 | 37.97 | 15.72 | 9.80 |
| 30 min | 4.65 | 1.94 | 9.68 | 1.32 | 13.23 | 46.45 | 19.36 | 13.23 |
| 60 min | 5.57 | 2.36 | 11.80 | 1.65 | 16.53 | 55.67 | 23.60 | 16.52 |

Acetaminophen—Pharmacologically Avtive Ingredient b:

| mean | 1 tablet [mg] | 5 tablets [mg] per tablet | 5 tablets [mg] all 5 | 10 tablets [mg] per tablet | 10 tablets [mg] all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 105.72 | 52.13 | 260.65 | 37.04 | 370.37 | 32.53 | 16.04 | 11.39 |
| 30 min | 128.05 | 64.27 | 321.35 | 45.64 | 456.40 | 39.40 | 19.78 | 14.04 |
| 60 min | 150.39 | 76.09 | 380.45 | 53.13 | 531.30 | 46.27 | 23.41 | 16.35 |

Condition c) 25 rpm, 250 mL:
Hydrocodone—Pharmacologically Avtive Ingredient a:

| mean | 1 tablet [mg] | 5 tablets [mg] per tablet | 5 tablets [mg] all 5 | 10 tablets [mg] per tablet | 10 tablets [mg] all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 2.96 | 1.34 | 6.68 | 1.22 | 12.23 | 29.63 | 13.39 | 12.24 |
| 30 min | 4.25 | 1.76 | 8.78 | 1.61 | 16.10 | 42.51 | 17.57 | 16.06 |
| 60 min | 5.14 | 2.28 | 11.38 | 1.97 | 19.73 | 51.39 | 22.78 | 19.73 |

Acetaminophen—Pharmacologically Avtive Ingredient b:

| mean | 1 tablet [mg] | 5 tablets [mg] per tablet | 5 tablets [mg] all 5 | 10 tablets [mg] per tablet | 10 tablets [mg] all 10 | 1 tablet [%] | 5 tablets [%] | 10 tablets [%] |
|---|---|---|---|---|---|---|---|---|
| 0 min | 0.00 | 0.00 | 0.00 | 0.00 | 0.00 | 0.00 | 0.00 | 0.00 |
| 15 min | 122.35 | 62.82 | 314.08 | 57.73 | 577.30 | 37.65 | 19.33 | 17.87 |
| 30 min | 157.45 | 76.26 | 381.28 | 68.26 | 682.63 | 48.45 | 23.46 | 21.01 |
| 60 min | 177.57 | 91.23 | 456.15 | 76.67 | 766.70 | 54.64 | 28.07 | 23.59 |

Comparative Example 1

10 mg Hydrocodone+325 mg Acetaminophen

Commercial tablets (Norco®, Watson Pharma) containing the same dose of hydrocodone and acetaminophen and having the following qualitative composition were tested for comparison:

| Substance |
|---|
| hydrocodone bitartrate |
| acetaminophen |
| croscarmellose sodium |
| crospovidone |
| magnesium stearate |
| cellulose, microcrystalline |
| povidone S |
| starch, corn |
| stearic acid |

The in vitro dissolution was tested in accordance with Example 1.
Condition 1: 50 rpm, 900 mL:
Hydrocodone—Pharmacologically Avtive Ingredient a:

| mean | 1 tablet [mg] | 10 tablets [mg] per tablet | 10 tablets [mg] all 10 | 1 tablet [%] | 10 tablets [%] |
|---|---|---|---|---|---|
| 0 min | 0.00 | 0.00 | 0.00 | 0.00 | 0.00 |
| 15 min | 9.52 | 8.80 | 88.03 | 95.17 | 88.03 |
| 30 min | 9.45 | 9.57 | 95.70 | 94.56 | 95.69 |
| 60 min | 9.52 | 9.41 | 94.13 | 95.14 | 94.13 |

Acetaminophen—Pharmacologically Avtive Ingredient b:

| mean | 1 tablet [mg] | 10 tablets [mg] per tablet | 10 tablets [mg] all 10 | 1 tablet [%] | 10 tablets [%] |
|---|---|---|---|---|---|
| 0 min | 0.00 | 0.00 | 0.00 | 0.00 | 0.00 |
| 15 min | 328.45 | 300.86 | 3008.63 | 101.06 | 92.57 |
| 30 min | 330.31 | 327.04 | 3270.37 | 101.63 | 100.63 |
| 60 min | 330.15 | 321.25 | 3212.50 | 101.59 | 98.85 |

Condition 2: 25 rpm, 250 mL:
Hydrocodone—Pharmacologically Avtive Ingredient a:

| mean | 1 tablet [mg] | 10 tablets [mg] per tablet | 10 tablets [mg] all 10 | 1 tablet [%] | 10 tablets [%] |
|---|---|---|---|---|---|
| 0 min | 0.00 | 0.00 | 0.00 | 0.00 | 0.00 |
| 15 min | 4.47 | 4.19 | 41.93 | 44.70 | 41.93 |
| 30 min | 5.36 | 5.30 | 53.03 | 53.55 | 53.05 |
| 60 min | 6.88 | 6.13 | 61.33 | 68.80 | 61.33 |

Acetaminophen—Pharmacologically Avtive Ingredient b:

| mean | 1 tablet [mg] | 10 tablets [mg] per tablet | 10 tablets [mg] all 10 | 1 tablet [%] | 10 tablets [%] |
|---|---|---|---|---|---|
| 0 min | 0.00 | 0.00 | 0.00 | 0.00 | 0.00 |
| 15 min | 142.07 | 133.69 | 1336.87 | 43.71 | 41.13 |
| 30 min | 178.55 | 177.74 | 1777.37 | 54.94 | 54.69 |
| 60 min | 221.90 | 207.28 | 2072.80 | 68.28 | 63.78 |

It becomes clear from the above data that the dosage forms according to Comparative Example 1 are not useful for avoiding overdose upon multiple dosing of both pharmacologically active ingredients. When a multitude of 10 dosage forms is tested thereby simulating 10-fold multiple dosing, the release is not significantly altered (10 dosage forms according to Comparative Example 1 vs. 1 dosage form according to Comparative Example 1).

Inventive Example 2

5 mg Hydrocodone+325 mg Acetaminophen

In accordance with Inventive Example 1, tablets were prepared comprising hot-melt extruded pellets, granules and powder as summarized in the table here below containing 5 mg hydrocodone+325 mg acetaminophen:

| per tablet [mg] | form | per tablet [mg] | Substance | Amount [%] |
|---|---|---|---|---|
| 180.00 | Pellets | 5.00 | hydrocodone bitartrate | 25.42 |
| | | 1.44 | citric acid | |
| | | 26.50 | macrogole 6000 | |
| | | 0.36 | α-tocopherole | |
| | | 9.00 | xanthan gum | |
| | | 101.70 | polyethylene oxide 7 mio. | |
| | | 36.00 | croscarmellose sodium | |
| 528.20 | Outer matrix | 325.00 | acetaminophen | 57.23 |
| | | 30.00 | croscarmellose sodium | |
| | | 45.00 | microcrystalline cellulose, type 101 | |
| | | 5.29 | hypromellose | |
| | | 2.28 | magnesium stearate | 0.32 |
| | | 6.90 | silicondioxide | 0.97 |
| | | 113.73 | microcrystalline cellulose, type 101 | 16.06 |
| 708.20 | | | | 100.00 |

Comparative Example 2

5 mg Hydrocodone+300 mg Acetaminophen

For comparative purposes, a commercial product (Vicodin®, AbbVie Inc.) containing the same dose of hydrocodone and 300 mg acetaminophen was tested.

In order to even more realistically simulate the situation in the gastrointestinal tract, the TIMagc system was used for testing release. The advanced gastric compartment of the TIMagc system realistically simulates gastric shape and motility and the consequent forces that are applied to dosage forms and food. This compartment can be used as standalone or as part of the TIM gastrointestinal systems to evaluate the bio-accessibility (availability for absorption) of nutrients. TIM is the dynamic in vitro gastro-intestinal model that simulates very closely the successive conditions of the stomach and small intestine. In the TIMagc the luminal conditions in the stomach are accurately simulated under computer-controlled conditions. The TIMagc system was designed and validated for the in vivo situation (see Bellmann et al., Development of an advanced in vitro model of the stomach for studying the gastric behaviour of compounds. Food Res. Internat. 2016).

The following experiments were performed for the following test products:

| hydrocodone/acetaminophen | |
|---|---|
| Fasted state | Fed state |
| 1 tablet of Inventive Example 2 | 1 tablet of Inventive Example 2 |
| 5 tablets of Inventive Example 2 | — |
| 10 tablets of Inventive Example 2 | 10 tablets of Inventive Example 2 |
| 10 tablets of Comparative Example 2 (Vicodin ®) | 10 tablets of Comparative Example 2 (Vicodin ®) |

The duration of each experiment in the fasted state was 60 minutes, in the fed state 180 minutes. Composition of the gastric intake (meal matrix) fasted or fed state conditions and simulated gastric parameters for each conditions are summarized in the table here below:

| TIMagc | Fed state | Fasted state |
|---|---|---|
| Intake (total) | 300 g | 270 g |
| High fat meal (HFM) | 150 g | — |
| Citrate buffer | — | 27 g |
| Water | 70 g | 213 g |
| Gastric start residue | 10 g | 30 g |
| Gastric electrolyte solution | 70 g | — |
| Gastric emptying T½ | 80 min | 20 min |
| Gastric pH | 6.5 to 1.7 in 180 min | 3.0 to 1.8 in 30 min |

The high fat meal (HFM) was used for fed state experiments as recommended by the FDA for clinical studies (FDA, CDER Guidance for Bioavailability and Fed Bioequivalence). This meal contained 50 energy % fat, 20 energy % protein and 30 energy % in the form of carbohydrates. The meal was composed of eggs, bacon, toast bread, potatoes, milk, butter and margarine. The meal was prepared as one batch, divided in portions (160 g) and stored below −18° C. Per TIMagc run one portion of the meal was used. Gastric secretions are composed of gastric enzymes, namely lipase, pepsin and ('swallowed') alpha-amylase, sodium acetate buffer, as well as gastric electrolyte solution (NaCl, KCl, $CaCl_2 \times 2H_2O$). Gastric starting fluid was composed of 15 g gastric electrolyte solution and 15 g HPMC (0.4%) plus bile (0.04%).

The in vitro gastrointestinal model TIM equipped with the advanced gastric compartment was used. The compartment consisted of a body part and the distal and proximal antrum.

FIG. 7 schematically illustrates the TIMagc representing A: gastric body; B: proximal antrum; C: distal (terminal) antrum; D: pyloric sphincter.

Removal and addition of warm water (37° C.) into the jacket results in peristaltic movements between the distal and proximal antrum. Gastric secretions, comprising gastric enzymes and gastric acid entered the TIMagc in the gastric body (FIG. 7, part A). The TIMagc emptied over time as a result of the pre-set gastric emptying curve according to the fed state or fasted state profile.

The gastric effluent was collected at the following time points: 5, 10, 15, 20, 30, 45 and 60 minutes in the fasted state and at 10, 15, 20, 30, 45, 60, 90, 120, 150, 180 minutes in the fed state. At the end of each experiment all residual material was collected by a pipet from the TIMagc and the compartment was rinsed once with 50 ml warm water. Withdrawn samples were directly treated for sample analysis by the sponsor.

The absolute amount of each pharmacologically active ingredient (hydrocodone and acetaminophen, respectively) recovered in the gastric effluent was calculated by multiplying the analyzed concentration in the sample with the collected volume (equation 1). Data are expressed as cumulative percentage of the intake of pharmacologically active ingredient:

$$A(\text{mg}) = C_{sample}(\mu g/ml) \cdot 10^{-3} \cdot V_{sample}(ml)$$

The results of the duplicate TIMagc runs are presented as mean±range.

The numerical results (cumulative values) for hydrocodone are summarized in the tables here below:

Hydrocodone cumulative amount [% LS]–fasted state:

| Time [min] | 1 tablet of inv. ex. 2 in 0.1M HCl | 10 tables of inv. ex. 2 in 0.1M HCl | 1 tablet of inv. ex. 2 in blank #1 | 1 tablet of inv. ex. 2 in blank #2 | 10 tablets of inv. ex. 2 in blank #1 | 10 tablets of inv. ex. 2 in blank #2 | 5 tablets of inv. ex. 2 in blank | 10 tablets of comp. ex. 2 in blank #1 | 10 tablets of comp. ex. 2 in blank #2 |
|---|---|---|---|---|---|---|---|---|---|
| 5 | 0.52 | 0.12 | 0.51 | 0.17 | 0.17 | 0.56 | 0.16 | 0.16 | 0.16 |
| 10 | 3.25 | 0.70 | 2.04 | 1.17 | 0.66 | 1.93 | 0.90 | 0.40 | 0.93 |
| 15 | 6.61 | 1.76 | 4.67 | 3.48 | 1.58 | 3.13 | 1.97 | 2.52 | 3.11 |
| 20 | 11.50 | 3.14 | 8.22 | 6.27 | 3.81 | 4.86 | 3.68 | 7.12 | 6.72 |
| 30 | 23.81 | 15.00 | 22.15 | 17.52 | 11.39 | 12.86 | 11.40 | 24.64 | 23.56 |

|  Time [min] | 1 tablet of inv. ex. 2 in 0.1M HCl | 10 tables of inv. ex. 2 in 0.1M HCl | 1 tablet of inv. ex. 2 in blank #1 | 1 tablet of inv. ex. 2 in blank #2 | 10 tablets of inv. ex. 2 in blank #1 | 10 tablets of inv. ex. 2 in blank #2 | 5 tablets of inv. ex. 2 in blank | 10 tablets of comp. ex. 2 in blank #1 | 10 tablets of comp. ex. 2 in blank #2 |
|---|---|---|---|---|---|---|---|---|---|
| 45 | 42.38 | 29.35 | 40.32 | 38.94 | 28.49 | 25.02 | 30.01 | 54.75 | 52.36 |
| 60 | 60.12 | 44.08 | 58.75 | 54.78 | 44.66 | 35.70 | 44.73 | 69.94 | 68.00 |
| Residue | 84.92 | 62.42 | 93.59 | 83.02 | 64.29 | 55.44 | 70.58 | 86.91 | 90.36 |
| Rinse | 89.32 | 70.68 | 95.36 | 83.83 | 70.21 | 60.45 | 75.89 | 90.48 | 93.06 |

Hydrocodone cumulative amount [% LS]–fed state:

| Time [min] | 1 tablet of inv. ex. 2 | 10 tablets of inv. ex. 2 | 10 tablets of comp. ex. 2 |
|---|---|---|---|
| 10 | 0.00 | 0.00 | 0.00 |
| 15 | 0.00 | 0.00 | 0.00 |
| 20 | 0.00 | 0.00 | 0.00 |
| 30 | 0.00 | 0.00 | 0.00 |
| 45 | 0.00 | 0.00 | 0.00 |
| 60 | 0.00 | 1.93 | 0.00 |
| 90 | 0.00 | 15.56 | 0.00 |
| 120 | 44.31 | 50.53 | 55.57 |
| 150 | 67.24 | 78.52 | 82.31 |
| 180 | 93.15 | 91.72 | 94.38 |
| Residue | 106.07 | 97.81 | 98.24 |
| Rinse | 106.78 | 98.20 | 99.26 |

The results for hydrocodone are also illustrated by FIGS. 8 to 10.

A comparison of the fasted state experiments for hydrocodone is shown in FIG. 8: Fasted state cumulative gastric effluent of hydrocodone as percentage (%) of intake of 1 tablet (♦), 10 tablets (■), 5 tablets (X) and Vicodin 10 tablets (▲), mean±range, n=2, hydrocodone 5 tablets: n=1, gastric emptying curve (black line).

A comparison of the fed state experiments for hydrocodone is shown in FIG. 9: Fed state cumulative gastric effluent of hydrocodone as percentage (%) of intake of 1 tablet (♦), 10 tablets (■) and Vicodin 10 tablets (▲) state, n=1, gastric emptying curve (black line).

A comparison of fasted versus fed state experiments for hydrocodone is shown in FIGS. 10A, 10B and 10C: Fasted versus fed state cumulative gastric effluent of hydrocodone as percentage (%) of intake of 1 tablet (A), 10 tablets (B) and Vicodin 10 tablets (C) state, n=1, dotted lines indicate fasted state, solid lines indicate fed state, gastric emptying curve (black lines).

The numerical results (cumulative values) for acetaminophen are summarized in the tables here below:

Acetaminophen cumulative amount [% LS] fasted state:

| Time [min] | 1 tablet of inv. ex. 2 in 0.1M HCl | 10 tables of inv. ex. 2 in 0.1M HCl | 1 tablet of inv. ex. 2 in blank #1 | 1 tablet of inv. ex. 2 in blank #2 | 10 tablets of inv. ex. 2 in blank #1 | 10 tablets of inv. ex. 2 in blank #2 | 5 tablets of inv. ex. 2 in blank | 10 tablets of comp. ex. 2 in blank #1 | 10 tablets of comp. ex. 2 in blank #2 |
|---|---|---|---|---|---|---|---|---|---|
| 5 | 2.67 | 0.60 | 1.40 | 0.84 | 1.05 | 4.29 | 1.27 | 0.13 | 0.14 |
| 10 | 9.10 | 2.20 | 4.37 | 3.02 | 2.98 | 12.09 | 4.82 | 0.35 | 0.90 |
| 15 | 13.88 | 3.80 | 7.51 | 5.89 | 4.84 | 18.66 | 7.68 | 1.76 | 2.45 |
| 20 | 19.16 | 5.33 | 10.80 | 8.65 | 7.67 | 24.84 | 10.54 | 4.28 | 4.58 |
| 30 | 29.74 | 18.39 | 22.00 | 18.86 | 16.19 | 38.85 | 19.72 | 14.45 | 14.78 |
| 45 | 44.95 | 32.43 | 37.11 | 39.96 | 32.66 | 53.40 | 39.54 | 35.63 | 35.65 |
| 60 | 59.71 | 45.76 | 51.72 | 55.40 | 45.64 | 64.09 | 52.77 | 48.90 | 48.91 |
| Residue | 77.60 | 59.35 | 76.86 | 79.54 | 59.47 | 79.01 | 73.00 | 68.20 | 72.53 |
| Rinse | 83.47 | 65.68 | 81.99 | 84.89 | 64.14 | 82.58 | 77.45 | 82.39 | 83.89 |

Acetaminophen cumulative amount [% LS]–fed state:

| Time [min] | 1 tablet of inv. ex. 2 | 10 tablets of inv. ex. 2 | 10 tablets of comp. ex. 2 |
|---|---|---|---|
| 10 | 0.03 | 0.01 | 0.00 |
| 15 | 0.12 | 0.04 | 0.00 |
| 20 | 0.20 | 0.08 | 0.00 |
| 30 | 0.35 | 0.15 | 0.00 |
| 45 | 0.63 | 0.63 | 0.00 |
| 60 | 0.94 | 2.75 | 0.01 |
| 90 | 2.22 | 17.71 | 0.48 |
| 120 | 37.27 | 49.09 | 39.72 |
| 150 | 58.46 | 71.41 | 63.09 |
| 180 | 84.56 | 82.47 | 74.34 |
| Residue | 97.72 | 87.71 | 78.34 |
| Rinse | 98.70 | 88.17 | 79.76 |

The results for acetaminophen are illustrated by FIGS. 11 to 13.

A comparison of fasted state experiments for acetaminophen is shown in FIG. 11: Fasted state cumulative gastric effluent of acetaminophen as percentage (%) of intake of 1 tablet (♦), 10 tablets (■), 5 tablets (X) and Vicodin 10 tablets (▲), mean±range, n=2, acetaminophen 5 tablets: n=1, gastric emptying curve (black line).

A comparison of fed state experiments for acetaminophen is shown in FIG. 12: Fed state cumulative gastric effluent of acetaminophen as percentage (%) of intake of 1 tablet (♦), 10 tablets (■) and Vicodin 10 tablets (▲) state, n=1, gastric emptying curve (black line).

A comparison of fasted versus fed state experiments for acetaminophen is shown in FIGS. 13A, 13B and 13C: Fasted versus fed state cumulative gastric effluent of acetaminophen as percentage (%) of intake of 1 tablet (A), 10 tablets (B) and Vicodin 10 tablets (C) state, n=1, dotted lines indicate fasted state, solid line indicate fed state, gastric emptying curve (black line).

It becomes clear from the above data that the dosage forms according to Inventive Example 2 are useful for avoiding overdose upon multiple dosing of both pharmacologically active ingredients, whereas the commercial dosage forms according to Comparative Example 2 are not useful for that purpose.

Inventive Example 3

10 mg Amphetamine

In accordance with Inventive Examples 1 and 2, pellets having the following composition were prepared and coated with a protective coating (Opadry®):

| per capsule | mg | wt.-% |
|---|---|---|
| amphetamine sulfate | 10.00 | 7.76 |
| polyethylene oxide $M_r$ 7 mio | 67.32 | 52.21 |
| macrogole 6000 | 16.03 | 12.43 |
| α-tocopherole | 0.24 | 0.19 |
| pregelatinized maize starch | 26.41 | 20.48 |
| Opadry ® clear 85F | 8.93 | 6.93 |
|  | 128.93 | 100.00 |

The pellets were filled into capsules (Capsugel® transparent, coni snap), size 2.

Comparative Example 3

10 mg Amphetamine

For comparative purposes, commercial tablets (Evekeo®, Arbor Pharmaceuticals) containing the same dose of amphetamine sulfate were tested.

In accordance with Inventive Example 2 and Comparative Example 2 (TIMagc system), the following experiments were performed for the following test products (the capsules/tablets were tested as such as well as the pellets contained in such capsules after removal of the capsule):

| amphetamine (capsules) | |
|---|---|
| Fasted state | Fed state |
| 1 capsule of Inventive Example 3 | 1 capsule of Inventive Example 3 |
| 10 capsules of Inventive Example 3 | 10 capsules of Inventive Example 3 |
| 10 tablets of Comparative Example 3 (Evekeo ®) | 10 tablets of Comparative Example 3 (Evekeo ®) |

| amphetamine (pellets) |
|---|
| Fasted state |
| 1 capsule content of Inventive Example 3 |
| 10 capsules content of Inventive Example 3 |

The numerical results (cumulative values) for amphetamine are summarized in the tables here below:

Amphetamine cumulative amount [% LS]–fasted state:

| Time [min] | 1 capsule of inv. ex. 3 in 0.1M HCl | 10 capsules of inv. ex. 3 in 0.1M HCl | 1 capsule of inv. ex. 3 in blank | 10 capsules of inv. ex. 3 in blank | 10 tablets of comp. ex. 3 in blank | pellets of 1 capsule of inv. ex. 3 in blank | pellets of 10 capsules of inv. ex. 3 in blank |
|---|---|---|---|---|---|---|---|
| 5 | 0.12 | n.d. | 0.14 | 0.13 | 1.84 | 1.75 | 0.76 |
| 10 | 4.07 | 1.36 | 3.79 | 2.62 | 8.63 | 9.55 | 4.08 |
| 15 | 14.61 | 3.71 | 10.88 | 7.88 | 16.38 | 20.27 | 8.72 |
| 20 | 25.63 | 7.91 | 21.94 | 14.31 | 24.89 | 30.05 | 14.79 |
| 30 | 42.17 | 26.51 | 39.17 | 30.87 | 42.76 | 49.49 | 29.13 |
| 45 | 61.58 | 48.91 | 60.09 | 53.78 | 64.39 | 67.98 | 47.49 |
| 60 | 73.24 | 65.15 | 74.63 | 65.70 | 76.41 | 79.94 | 61.01 |
| Residue | 84.57 | 84.52 | 93.41 | 85.38 | 93.76 | 95.90 | 79.82 |
| Rinse | 86.69 | 86.51 | 93.90 | 86.96 | 94.30 | 97.18 | 80.86 |

Amphetamine cumulative amount [% LS]–fed state:

| Time [min] | 1 capsule of inv. ex. 3 | 10 capsules of inv. ex. 3 | 10 tablets of comp. ex. 3 |
|---|---|---|---|
| 30 | 0.89 | 3.16 | 9.45 |
| 45 | 5.32 | 9.42 | 19.95 |
| 60 | 16.89 | 20.32 | 33.86 |
| 90 | 65.62 | 58.88 | 55.21 |
| 120 | 81.51 | 77.69 | 80.94 |
| 150 | 87.79 | 90.50 | 94.39 |
| 180 | 91.78 | 95.26 | 99.90 |
| Residue | 94.08 | 96.77 | 101.90 |
| Rinse | 94.08 | 97.29 | 102.33 |

The results for amphetamine capsules/tablets are also illustrated by FIGS. 14 to 16.

A comparison of fasted state experiments for amphetamine (capsules) is shown in FIG. 14: Fasted state cumulative gastric effluent of amphetamine as percentage (%) of intake of amphetamine of 1 capsule (♦), 10 capsules (■) and Evekeo 10 tablets (▲), n=1, gastric emptying curve (black line).

A comparison of fed state experiments for amphetamine (capsules) is shown in FIG. 15: Fed state cumulative gastric effluent of amphetamine as percentage (%) of intake of amphetamine of 1 capsule (♦), 10 capsules (■) and Evekeo 10 tablets (▲), n=1, gastric emptying curve (black line).

A comparison of fasted versus fed state experiments for amphetamine (capsules/tablets) is shown in FIGS. 16A, 16B and 16C: Fasted versus fed state cumulative gastric effluent of amphetamine as percentage (%) of intake of amphetamine of 1 capsule (A), 10 capsules (B) and Evekeo 10 tablets (C), n=1, dotted lines indicate fasted state, solid line indicate fed state, gastric emptying curve (black lines).

The results for the separated amphetamine pellets are illustrated by FIG. 17. A comparison of fasted state experiments for amphetamine (pellets) is shown in FIG. 17: Fasted state cumulative gastric effluent of amphetamine as percentage (%) of intake of amphetamine of pellets of 1 capsule (X) and pellets of 10 capsules (*), n=1, gastric emptying curve (black line).

It becomes clear from the above data that the dosage forms according to Inventive Example 3 are useful for avoiding overdose upon multiple dosing of the pharmacologically active ingredient, whereas the commercial dosage forms according to Comparative Example 3 are not useful for that purpose.

It can be concluded from a comparison of Inventive Example 2 with Comparative Example 2 and from a comparison of Inventive Example 3 with Comparative Example 3 that under simulated fed state in vitro conditions (filled stomach), the residence time of the dosage forms corresponds to the stomach emptying intervals independent of the number of dosage forms that are contained in the stomach, i.e. that are administered simultaneously. However, under such fed state conditions a potential abuser cannot achieve the desired kick anyway so that these conditions are not relevant for a potential abuser.

In contrast, under simulated fasted state in vitro conditions, which are relevant for a potential abuser, the number of dosage forms that are contained in the stomach, i.e. that are administered simultaneously, can be distinguished from one another (1 vs. 5 vs. 10). For avoiding overdosing, the residence time in the stomach is of clinical relevance. The longer the residence time in the stomach, the more difficult (less likely) it is to achieve the desired "kick" by simultaneously administering a plurality of dosage forms.

The experimental data demonstrate that the inventive formulations provide an extended residence time in the stomach when administered simultaneously as a plurality, whereas the comparative formulations do not show such an extended residence time in the stomach.

The invention claimed is:

1. A method for reducing the risk that a human subject will suffer an overdose of pharmacologically active ingredient a after accidental or intentional simultaneous administration of a plurality of intact dosage forms containing in combination an overall supratherapeutic dose of the pharmacologically active ingredient a, said method comprising (a) administering to said human subject said plurality of intact dosage forms containing in combination an overall supratherapeutic dose of the pharmacologically active ingredient a and (b) achieving as a result said administering of said plurality of intact dosage forms to said human subject does not cause said human subject to suffer an overdose of the pharmacologically active ingredient a, wherein each of said plurality of intact dosage forms comprises said pharmacologically active ingredient a being a stimulant, at least a portion of the pharmacologically active ingredient a being contained in one or more particles A, each of said one or more particles A comprising a homogeneous mixture of the pharmacologically active ingredient a, one or more disintegrants and a polymer matrix, the polymer matrix comprising a polyalkylene oxide having an average molecular weight of at least 200,000 g/mol, and wherein after 30 minutes under in vitro conditions at 37° C. in 900 mL 0.1 M HCl at 25 rpm in accordance with Ph. Eur.:
   (i) a single intact dosage form has released X mg of the pharmacologically active ingredient a originally contained in the dosage form; and
   (ii) a multitude of 10 intact dosage forms has released Y mg of the pharmacologically active ingredient a originally contained in said multitude of 10 dosage forms; wherein Y/10 is not more than 45% of X.

2. The method according to claim 1, wherein Y/10 is not more than 40% of X.

3. The method according to claim 1, wherein after 30 min under in vitro conditions at 37° C. in 900 mL 0.1 M HCl at 25 rpm in accordance with Ph. Eur.
   (i) a single dosage form has released at least 30 wt.-% of the pharmacologically active ingredient a originally contained in the dosage form; and/or
   (ii) a multitude of ten dosage forms has released not more than 25 wt.-% of the overall content of the pharmacologically active ingredient a originally contained in the multitude of ten dosage forms.

4. The method according to claim 1, wherein the content of the polyalkylene oxide in the dosage form amounts to at least 25 mg.

5. The method according to claim 4, wherein the content of the polyalkylene oxide in the dosage form amounts to at least 50 mg.

6. The method according to claim 1, wherein the polyalkylene oxide is a polyethylene oxide.

7. The method according to claim 1, wherein the polyalkylene oxide has an average molecular weight of at least 500,000 g/mol.

8. The method according to claim 7, wherein the polyalkylene oxide has an average molecular weight in the range of 1,000,000 g/mol to 15,000,000 g/mol.

9. The method according to claim 1, wherein the content of the polyalkylene oxide is at least 30 wt.-%, based on the total weight of the particle(s) A.

10. The method according to claim 1, wherein the one or more particles A have a breaking strength of at least 300 N.

11. The method according to claim 1, wherein the one or more particles A amount to a total number within the range of from 20 to 600.

12. The method according to claim 1, wherein the one or more particles A amount to a total content of at least 25 wt.-%, based on the total weight of the dosage form.

13. The method according to claim 1, wherein the one or more particles A are tamper-resistant as such so that they also provide tamper-resistance after they have been separated from the remaining constituents of the dosage form.

14. The method according to claim 1, wherein the one or more particles A contain the total amount of the pharmacologically active ingredient a that is contained in the dosage form.

15. The method according to claim 1, wherein the one or more particles A are thermoformed by hot-melt extrusion.

16. The method according to claim 1, wherein the pharmacologically active ingredient a is a stimulant selected from the group consisting of amphetamine, dex-amphetamine, dex-methylphenidate, atomoxetine, caffeine, ephedrine, phenylpropanolamine, phenylephrine, fencamphamin, fenozolone, fenetylline, methylenedioxymethamphetamine (MDMA), methylenedioxypyrovalerone (MDPV), prolintane, lisdexamfetamine, mephedrone, methamphetamine, methylphenidate, modafinil, nicotine, pemoline, phenylpropanolamine, propylhexedrine, dimethylamylamine, pseudoephedrine, and the physiologically acceptable salts thereof.

17. The method according to claim 1, wherein each of said intact dosage forms is a capsule.

18. The method according to claim 1, wherein each of said intact dosage forms is a tablet.

19. The method according to claim 1, wherein each of said intact dosage forms additionally contains a pharmacologically active ingredient b which differs from the pharmacologically active ingredient a.

20. The method according to claim 19, wherein the pharmacologically active ingredient b is selected from the group consisting of acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, phenazone, metamizole sodium, aminophenazone, propyphenazone, nifenazone, acetaminophen (paracetamol), phenacetin, bucetin, propacetamol, rimazolium, glafenine, floctafenine, viminol, nefopam, flupirtine, ziconotide, methoxyflurane, nabiximols, dihydroergotamine, ergotamine, methysergide, lisuride, flumedroxone, sumatriptan, naratriptan, zolmitriptan, rizatriptan, almotriptan, eletriptan, frovatriptan, pizotifen, clonidine, iprazochrome, dimetotiazine, oxetorone, phenylbutazone, mofebutazone, oxyphenbutazone, clofezone, kebuzone, indomethacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, piroxicam, tenoxicam, droxicam, lornoxicam, meloxicam, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, naproxcinod, mefenamic acid, tolfenamic acid, flufenamic acid, meclofenamic acid, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, oxycinchophen, sodium aurothiomalate, sodium aurotiosulfate, auranofin, aurothioglucose, aurotioprol, penicillamine, bucillamine, their physiologically acceptable salts, and mixtures thereof.

21. The method according to claim 1, wherein the particle(s) A comprise an antioxidant.

22. The method according to claim 16, wherein the pharmacologically active ingredient a is selected from the group consisting of amphetamine, amphetaminil, lisdexamfetamine dimesylate, and metamphetamine, and the physiologically acceptable salts thereof, and combinations thereof.

23. The method according to claim 22, wherein the pharmacologically active ingredient a is selected from the group consisting of amphetamine and the physiologically acceptable salts thereof.

24. The method according to claim 16, wherein the pharmacologically active ingredient a is selected from the group consisting of methylphenidate and the physiologically acceptable salts thereof.

25. The method according to claim 16, wherein the one or more disintegrants are selected from the group consisting of starches, starch derivatives, cellulose derivatives and gas releasing substances.

26. The method according to claim 25, wherein the one or more disintegrants are selected from the group consisting of maize starch, pregelatinized starch, sodium starch glycolate, croscarmellose sodium, and sodium bicarbonate.

27. A method for reducing the risk that a human subject will suffer an overdose of pharmacologically active ingredient a after accidental or intentional simultaneous administration of a plurality of intact dosage forms containing in combination an overall supratherapeutic dose of the pharmacologically active ingredient a, said method comprising (a) administering to said human subject said plurality of intact dosage forms containing in combination an overall supratherapeutic dose of the pharmacologically active ingredient a and (b) achieving as a result said administering of said plurality of intact dosage forms to said human subject does not cause said human subject to suffer an overdose of the pharmacologically active ingredient a, wherein each of said plurality of intact dosage forms comprises said pharmacologically active ingredient a being at least one member selected from the group consisting of amphetamine, methylphenidate, and physiologically acceptable salts thereof, at least a portion of the pharmacologically active ingredient a being contained in one or more particles A, each of said one or more particles A comprising an extruded mixture of the pharmacologically active ingredient a, one or more disintegrants and a polymer matrix, the polymer matrix comprising a polyalkylene oxide having an average molecular weight of at least 200,000 g/mol, the one or more disintegrants being selected from the group consisting of maize starch, pregelatinized starch, sodium starch glycolate, croscarmellose sodium, and sodium bicarbonate, wherein no polyalkylene oxide and no disintegrant is contained outside of the one or more particles A, wherein each of the one or more particles A exhibits a breaking strength of at least 500 N, and wherein after 30 minutes under in vitro conditions at 37° C. in 900 mL 0.1 M HCl at 25 rpm in accordance with Ph. Eur.:

(i) a single intact dosage form has released X mg of the pharmacologically active ingredient a originally contained in the dosage form; and (ii) a multitude of 10 intact dosage forms has released Y mg of the pharmacologically active ingredient a originally contained in said multitude of 10 dosage forms; wherein Y/10 is not more than 45% of X.

28. The method according to claim 27, wherein the one or more particles A cannot be comminuted with a hammer or with a mortar and pestle.

* * * * *